United States Patent [19]
Kim

[11] Patent Number: 5,810,884
[45] Date of Patent: Sep. 22, 1998

[54] APPARATUS AND METHOD FOR CLOSING A VASCULAR PERFORATION AFTER PERCUTANEOUS PUNCTURE OF A BLOOD VESSEL IN A LIVING SUBJECT

[75] Inventor: Ducksoo Kim, Dover, Mass.

[73] Assignee: Beth Israel Deaconess Medical Center, Boston, Mass.

[21] Appl. No.: 858,890

[22] Filed: May 19, 1997

Related U.S. Application Data

[60] Provisional application No. 60/026,555 Sep. 9, 1996.
[51] Int. Cl.⁶ ................................................. A61B 17/04
[52] U.S. Cl. ........................................... 606/213; 606/215
[58] Field of Search .................................. 606/213, 139, 606/215, 228, 230

[56] References Cited

U.S. PATENT DOCUMENTS

| | | | |
|---|---|---|---|
| 5,370,660 | 12/1994 | Weinstein et al. | 606/215 |
| 5,441,517 | 8/1995 | Kensey | 606/213 |
| 5,454,833 | 10/1995 | Boussignac et al. | 606/213 |
| 5,531,759 | 7/1996 | Kensey et al. | 606/213 |
| 5,540,715 | 7/1996 | Katsaros et al. | 606/213 |
| 5,545,178 | 8/1996 | Kensey et al. | 606/213 |
| 5,549,633 | 8/1996 | Evans et al. | 606/139 |
| 5,601,602 | 2/1997 | Fowler | 606/213 |

*Primary Examiner*—Gary Jackson
*Attorney, Agent, or Firm*—David Prashker

[57] ABSTRACT

The present invention provides unique apparatus, systems and methods for an aligned closing and stabilized sealing of a vascular perforation in a chosen blood vessel after percutaneous puncture and completion of a catheterization procedure. The invention is an adaptation of the conventionally known modified Seldinger technique in which the means for guidance, closing and stabilized sealing are deployed and positioned during the manipulations performed during the percutaneous puncture of the blood vessel itself.

4 Claims, 36 Drawing Sheets

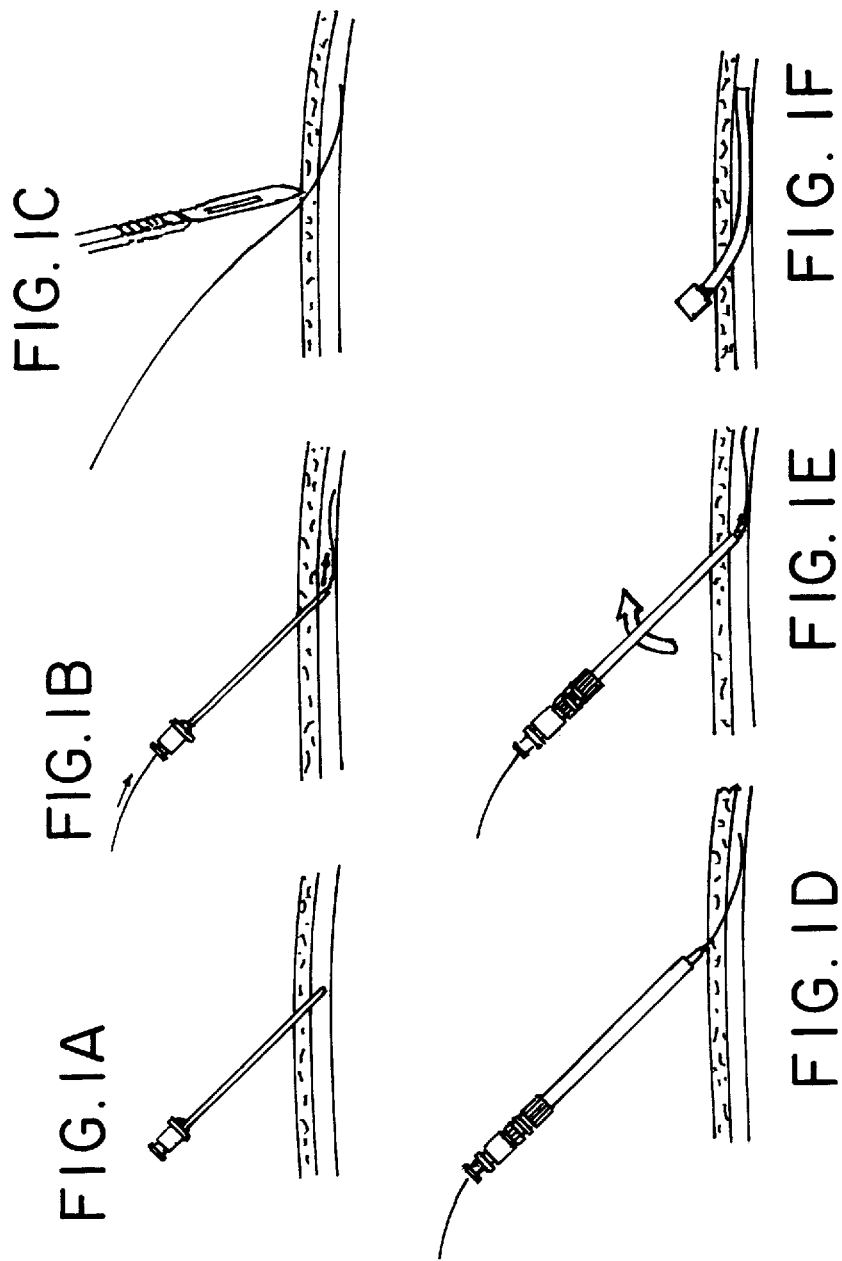

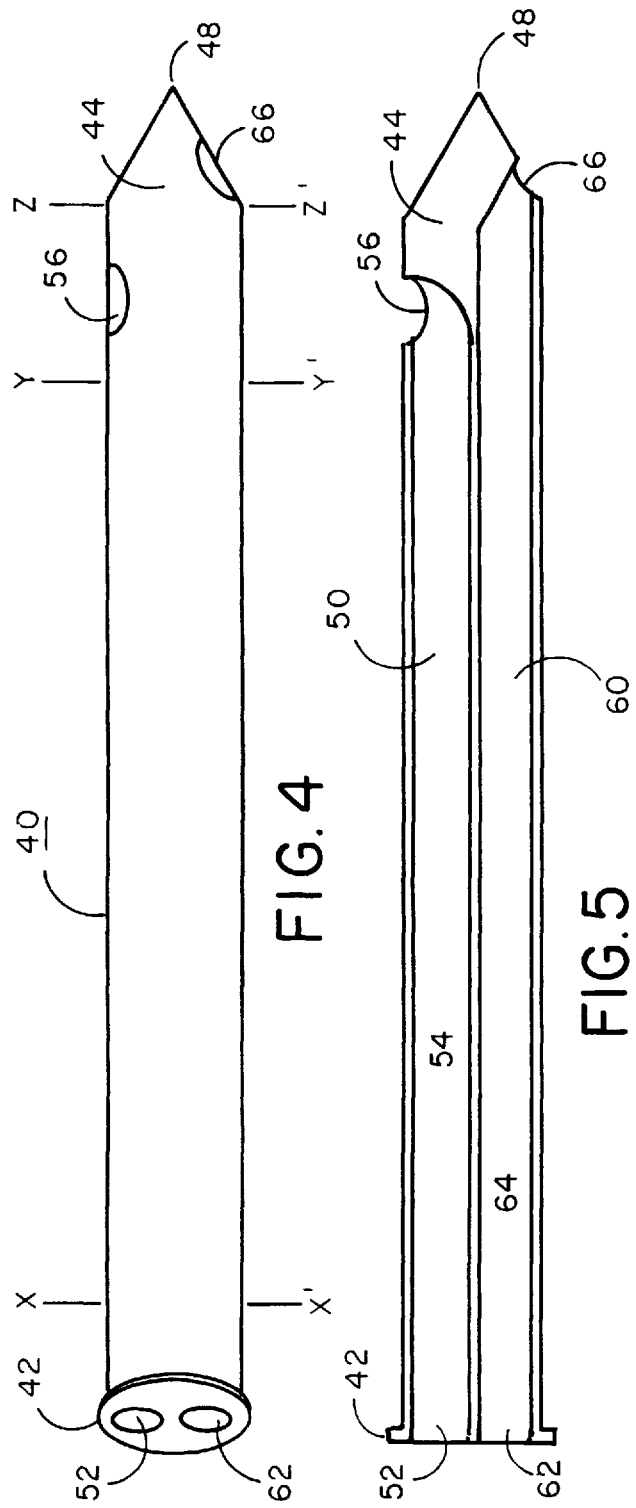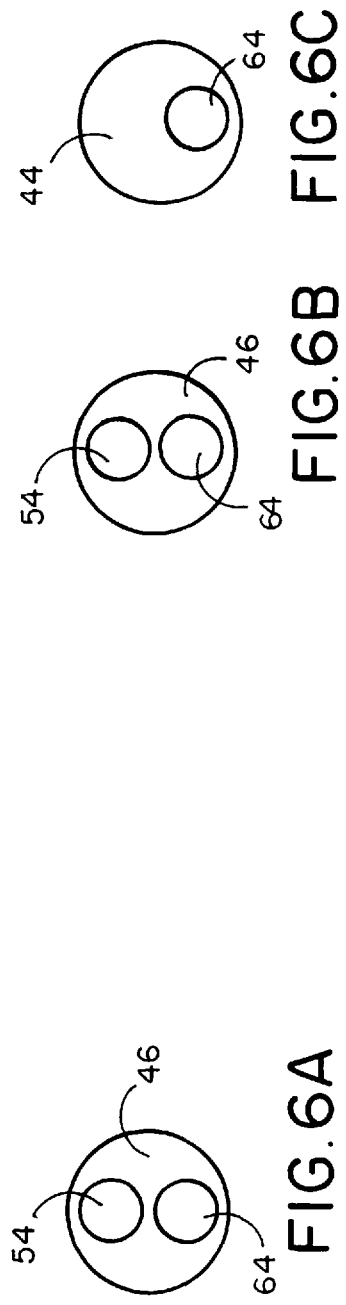

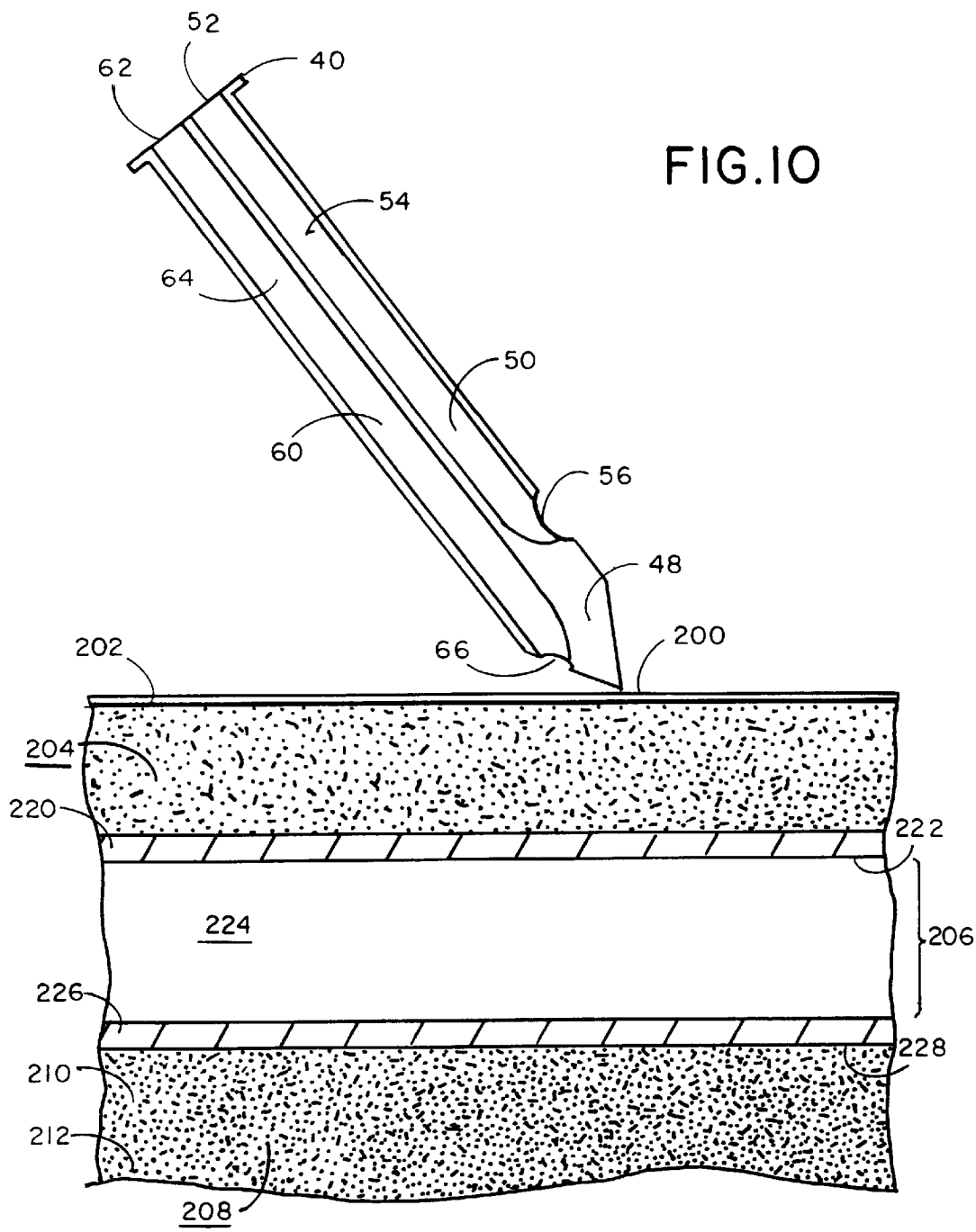

APPARATUS AND METHOD FOR CLOSING A VASCULAR PERFORATION AFTER PERCUTANEOUS PUNCTURE OF A BLOOD VESSEL IN A LIVING SUBJECT

PROVISIONAL APPLICATION

A Provisional Application for the present invention was filed on Sep. 9, 1996 as Application No. 60/026,555.

FIELD OF THE INVENTION

The present invention is concerned generally with closures and closure systems for vascular punctures; and is directed particularly to apparatus and methods for aligned closing and stabilized sealing of a vascular perforation after percutaneous puncture of a blood vessel.

BACKGROUND OF THE INVENTION

Catheterization is now and has been for many years an integral tool in the diagnosis of vascular diseases; and it also allows the physician to intervene and treat the vascular disease itself. Ongoing advances in the development of vascular catheterization techniques continue to improve the efficacy of these procedures, as well as expand their use.

Each year in the U.S., more than 1.2 million individuals undergo diagnostic catheterization procedures for evaluation of heart, coronary, peripheral, or cerebral arterial blockages causing heart attack, leg claudication, or stroke, respectively. The number of these procedures is increasing every year— especially in the field of interventional catheterization procedures such as percutaneous tranluminal angioplasty, atherectomy, and stent placement for opening up the arterial blockages. Last year alone, cardiologists performed approximately 400,000 therapeutic interventional catheterization procedures.

For such interventions, large diameter catheters up to 12 French (3.6 mm diameter) are typically used; which means an approximately 3.6 mm-in-diameter hole is made in the access blood vessel, such as a femoral, brachial or axillary artery. Often the femoral artery is used as a favored access site for these procedures because of its relatively superficial location in the groin and large size (6 to 8 mm in diameter) relative to the other arteries (the brachial artery being about 4 to 5 mm in diameter and the axillary artery being 5 to 6 mm in diameter).

Prior to 1953, however, obtaining access to a blood vessel for introduction of a catheter and performance of a catheterization procedure in-vivo depended on direct surgical isolation of the blood vessel of choice and used surgically placed catheters or percutaneously placed needle-cannulas. However, in 1953, Sven Seldinger developed a non-surgical technique for percutaneous catheterization of the femoral artery. His technique, in modified form, has become the most favored and the standard non-surgical procedure for percutaneous puncture of a blood vessel. The modified Seldinger technique is illustrated by prior art FIGS. 1A–1F respectively; and a summary recitation examplifying this procedure using the femoral artery as a target is presented below.

The modified Seldinger technique

Using sterile technique, 2% lidocaine is injected superficially to produce a wheal at the intended puncture site and which is more deeply lateral and medial to the arterial pulse. The femoral artery is stabilized by placing a finger above and below the puncture site. Alternatively, two fingers may be placed above the pulse. A needle is placed through the skin nick as shown by FIG. 1A; and then advanced at a 45–60 degree angle with a swift stabbing motion directed towards the finger(s) above the pulse until contact is made with the bony pelvis. The course of the needle should never be altered during advancement as this increases the risk of vessel injury.

In the presence of an adequate pulse, a vertical pulsation of the needle usually indicates that the needle tip has passed through the artery. The stylet is removed and the needle is partially withdrawn until pulsatile arterial flow is obtained. The needle should be withdrawn at the same angle applied during advancement in order to avoid injury to the artery wall. Once adequate arterial flow is obtained, the needle is gently tilted downward to facilitate wire advancement.

Once vigorous blood return occurs, a flexible guidewire is placed into the blood vessel via the needle as shown by FIG. 1B. The needle is then removed from the blood vessel, the guidewire is left in place, and the hole in the skin around the guidewire is enlarged with a scalpel as shown by FIG. 1C. Subsequently, a sheath and a dilator is placed over the guidewire as shown by FIG. 1D. Thereafter, the sheath and dilator is advanced over the guidewire and directly into the blood vessel as shown by FIG. 1E. Finally, the dilator and guidewire is removed while the sheath remains in the blood vessel as illustrated by FIG. 1F. The catheter is then inserted through the sheath and fed through the blood vessel to reach the desired location.

It will be noted that the purpose of the dilator is to form a tract to facilitate passage of the softer catheter for which it is subsequently exchanged. During all exchanges, the guidewire should be wiped with a gauze pad dampened with heparinized saline (HS), and manual pressure must be maintained upon the groin. Care should also be taken to avoid inadvertent withdrawal of the wire during exchanges. This is accomplished by simultaneous advancement of the guidewire into the blood vessel during catheter removal. Upon completion of the procedures, the catheter is removed and manual compression is applied over the puncture site for 10–15 minutes, depending upon the catheter diameter and risks for hemorrhage.

The problems resulting from a percutaneous catheterization procedure

The collective medical experiences of physicians and surgeons in over 40 years usage for the modified Seldinger technique has revealed the kinds and variety of complications which typically occur as a consequence of non-surgical percutaneous puncture of a blood vessel, especially around the locally-sited perforation and at the aperture void space of the puncture itself. To begin with, it is clear that serious bleeding can occur at the puncture site. The risk of bleeding increases with the use of larger interventional catheters typically used in therapeutic interventional procedures (although the degree of increase also depends on anticoagulation medication and puncture techniques) as well as in patients with impaired coagulation mechanisms. Unfortunately, in some instances it is not possible to completely correct underlying coagulation deficiencies or to stop the anticoagulation medications; percutaneous catheterization, even with fine catheters, has been considered previously and remains today a high-risk procedure for these patients.

Simply stated, the recurring medical problem is how to effectively close and seal the vascular perforation in an artery or vein after percutaneous puncture of the chosen blood vessel and completion of the desired diagnostic or interventional catheter procedure. The fluid-tight closing of a locally-sited puncture and the aperture void space of the catheter tract and vascular perforation is necessary to prevent uncontrolled bleeding and other complications.

It will be appreciated that when non-interventional diagnostic catheterization is performed using relatively small-diameter catheters (5 to 7 French, 1.5–2.1 mm diameter), the hemostasis at the puncture site after completion of the procedure is typically achieved by manual compression on the skin immediately over the puncture site. Such manual compression is usually uneventful and takes only 10 to 15 minutes to perform. The patient will then be on bed rest for the next 6 to 8 hours before ambulation. With this post-catheterization care, a complication at the puncture site associated with the diagnostic catheterization is unusual and infrequent. Most complications as do occur are hemotomas, transient subcutaneous (below skin) collections of blood that leaked from the puncture hole during the manual compression. The hematomas usually are small, minor, and self-limited without long-term sequele; and are treatable without need of transfusion or surgical closure of the puncture hole.

Sometimes, however, serious complications do take place and occur even with simple diagnostic catheterization procedures. The major complications include (1) formation of pseudoaneurysm (formation of a cavity of blood around the artery by continuous leakage of blood through the hole due to failure of spontaneous closure of the puncture hole); (2) a hematoma or pseudoaneurysm formation large enough to compress the adjacent nerves causes paralysis of the leg; and (3) continuous bleeding into the free body spaces (such as the pelvic cavity, abdominal cavity or retroperitoneal space) which can cause rapid loss of blood and subsequent hypotensive shock. Fortunately, these major complications from the diagnostic catheterization are rare (occurring in less than 0.5% of patients), and mortality from such complications is even much lower.

In comparison, interventional catheterization procedures, particularly those of a major artery, are far more likely to produce major complications. Interventional catheterization procedures require aggressive anticoagulation during and after the procedures. For example, 10,000 units of heparin are used for interventional coronary catheterization procedures vs. 5,000 units of heparin for diagnostic cardiac catheterization procedures. Concurrent antithrombotic treatment in addition to use of a larger catheter in the interventional catheterization procedures is another reason for more prevalent major complications with the interventional catheterization procedures. Also, as mentioned above, the interventional catheters are larger than the diagnostic catheters; and, in the interventional catheterization procedures, the puncture hole is often equal to or larger than 50% of the blood vessel diameter—a hole size which is too big for a major artery to accommodate and heal unaided after completion of the procedure.

It is also not unusual that the application of manual compression is not adequate to achieve hemostasis. Hemostasis of an arterial puncture site after removal of the interventional catheter requires a much longer duration of compression (10 to 60 minutes). This long manual compression is inconvenient for physicians and can be very painful to the patient. Frequently, however, manual compression is not sufficient to achieve reliable, efficient hemostasis at the arterial puncture hole.

Even the use of a mechanical compression device (such as the C-clamp device) has been largely ineffective and showed only marginal improvement over the manual compression method in terms of efficiency reducing complication rate. With either manual or mechanical compression method, bedrest is needed for 6 to 24 hours after completion of compression on the puncture site. Even with this, late bleeding complications are observed in approximately 5 to 9% of cases.

Thus, complications associated with manual compression often require vascular surgical repair. These range from 1–2% of cases after conventional balloon angioplasty, 3% of cases after atherectomy, and 11% of cases after coronary stent placement. These rates of complication are much higher than those arising in the diagnostic catheterization procedures because of the use of a larger sheath size and the need for greater anticoagulation. The requirement for large doses of heparin during and immediately after angioplasty in particular also delays sheath removal, which, in turn, requires more intensive nursing care and prolongs hospital stay.

The interventional catheterization procedure is also frequently complicated by other events such as hypotensive shock, pseudoaneurysm, formation of arteriovenous fistula (a pathological connection between the adjacent artery and vein) or nerve damage. These major complications associated with interventional catheterization procedures are more frequent (up to 11% of cases) and are more serious than those typically occurring after diagnostic catheterization procedures. These complications are usually treated by intensive medical care or surgery, which add medical expense and subject the patient to another potential medical and surgical morbidity risk in addition to prolonging the hospitalization.

Prior art solutions to the bleeding problems

To obtain hemostasis after percutaneous puncture of a major artery or vein, several technologies have been developed to achieve closure at the vascular puncture sites. These include the following.

Conventional compression techniques: Upon completion of a diagnostic or interventional procedure, the catheter or introducer sheath is removed and manual compression is applied over the puncture site for 10–15 minutes, depending upon the catheter diameter and risks for hemorrhage. Following compression, the puncture site should be observed for several minutes before moving the patient. If a hematoma is present, its borders should be marked on the skin so that expansion will be more easily detected. An appropriate pressure dressing may be applied for 1–2 hours if a hematoma has developed, or if the patient is hypertensive, or if anticoagulation was administered or if hemostasis was difficult to achieve. In some institutions, it is customary to use mechanical C clamps to aid in the hemostasis procedure after catheterization.

Closure devices and systems: In recent years a variety of different articles, apparatus, and methods by which to plug the puncture site and/or fill the aperture void space of the vascular perforation have been developed. There are merely represented and examplified by the following: a radiopaque rigid anchor, a compressed collagen plug, and a thin filament connecting the two in a pulley-like arrangement [U.S. Pat. Nos. 5,282,827 and 5,441,517]; an expandable closure to be located within the interior of the blood vessel where the closure forms an enlarged engagement surface [U.S. Pat. No. 4,744,364]; a closure device with an expandable balloon and atraumatic tip of the distal end [U.S. Pat. No. 5,383,896]; a closure sheet adapted to conform to the inner surface of a blood vessel and having a plurality of barbs on its surface [U.S. Pat. No. 5,383,897]; a foam plug adapted to engage the tissue adjacent to the vascular puncture and hold the foam plug in place [U.S. Pat. No. 4,890,612]; a syringe-like device for inserting collagen or other hemostatic materials into a puncture site [U.S. Pat. No. 5,437,631]; a syringe-like device for inserting hemostatic material through a tissue channel against the outside wall of a blood vessel [U.S. Pat. No. 5,391,183]; and an apparatus for suturing fascial tissue for deep punctures using a trocar sheath, a flexible membrane, and a pair of suture-carrying needles [U.S. Pat. No. 5,391,182].

In addition, a range of differing medical views and positions comparing the value and benefits of using percutaneous hemostasis devices with conventional manual compression have been reported in the scientific literature. Examples of these views include: Sanborn et al., *J. Am. Coll. Cardial.* 22: 1273–1279 (1993); Krause, P. B. and L. W. Klein, *JACC* 22: 1280–1282 (1993); and the references cited within each of these publications.

Two other devices and methods deserve special mention. These are:

(1) The Hemostatic Puncture Closure Device (HPCD) sold commercially by Quintor Instrument Co. [reviewed by de Swart et al., *Am. J. Cardiol.* 72: 445–449 (1993)]. This commercially manufactured and sold device utilizes a flat resorbable polymer anchor placed inside the vessel lumen, to which a collagen plug is then attached to the outer vessel wall by a resorbable suture. The device is a bioresorbable article used to seal the femoral arterial access puncture site and establish hemostasis after an arterial catheterization. The device consists of a small anchor, a collage sponge, and a suture. The anchor, an integral component of the seal, is deployed inside the anterior wall of the artery; and the collagen sponge is positioned securely on the outside of the anterior wall of the artery. The suture links the anchor and collagen together to seal the arteriotomy. Anchor components are said to be absorbed by the body in 60–90 days.

(2) The VasoSeal device sold commercially by Datascope Corp. [reviewed by Foran et al. *Br. Heart J.* 69: 424–429 (1993)]. This vascular hemostasis device was recently developed and delivers purified, absorable bovine collagen through an introducer sheath to promote hemostasis at the arterial puncture site. The VasoSeal device consisted of four parts: a blunt-tipped, 11 French dilator; one of seven differently sized 11.5 Fr sheaths selected by length using a preprocedure needle depth measurement technique; and two 90 mg collagen cartridges.

In use, a 11.5 French applicator sheath, selected by length, is advanced down to the arterial surface. Then while arterial compression is maintained, the first collagen cartridge is advanced out of the sheath; and the sheath is slowly pulled back to fill the track through the subcutaneous tissue. The second collage cartridge is then applied while the sheath is gradually pulled back to completely fill the track up to the skin surface. If one cartridge of collage completely filled the subcutaneous track (as in a thin person), a second collagen cartridge is not required. After the collagen cartridges are applied, the 11.5 French applicator sheath is removed completely and partial upstream compression, as well as light pressure directly over the puncture site of the vessel is applied for 2 to 5 minutes to obtain complete hemostasis.

To date accordingly, few acceptable alternatives have been available for arterial or venous closure after a cardiac or peripheral catheterization. Manual or mechanical compression techniques are uncomfortable for the patients and require significant monitoring in the current reduced staffing environment. Pressure dressings, if applied after hemostasis is achieved, are a source of discomfort for the patient due to continuing pressure and skin irritation from the elastic bandage used to hold the dressing in place.

Also, the presently available devices, systems, and techniques as described above and the commercially sold articles [such as the Vasoseal and the Hemostatic Puncture Closure Device] have many drawbacks, complications and limitations associated with their use. These include the problems also occurring with manual compression, such as local hematoma, arteriovenous fistula and pseudoaneurysm. These devices can also fail due to kinking, displacement, or accidental removal; and can result in large volume bleeding requiring a transfusion, and dislodgement into the lumen of the vessel causing vessel blockage.

There is thus a long standing and well recognized need for improvements in closure devices and methods which would be effective in preventing bleeding and major complications which result from a vascular perforation caused by percutaneous puncture of a blood vessel. Were such an improvement to be developed, the advantages, benefits, and medical value of such a unique apparatus and methodology would be apparent, immediate, and substantive to physicians and surgeons alike.

SUMMARY OF THE INVENTION

The present invention is definable in the alternative as a minimal form device; as an article having an increasing number and complexity of component parts; and as a system and methodology. Each aspect of the present invention will be delineated individually.

A first aspect of the invention provides an aiding apparatus for guiding and stabilizing a vascular closure in a vascular perforation after percutaneous puncture of a blood vessel in a living subject, said perforated blood vessel having an identifiable anterior vascular wall, a locally-sited puncture and aperture void space in the anterior vascular wall, a central blood flow channel, and an oppositely disposed posterior vascular wall, said aiding apparatus comprising:

a closure guiding stabilizer suitable for on-demand aligned deployment within a living subject adjacent an exterior surface of a posterior vascular wall of a blood vessel after percutaneous puncture and for on-demand extension and passage in part from the aligned deployment within a living subject through a posterior vascular wall, across a blood flow channel, and out an aperture void space of a puncture site in an anterior vascular wall into the ambient environment, said closure guiding stabilizer being comprised of a buttressing support member having predetermined dimensions and an elongated configuration suitable for on-demand placement adjacent to an exterior surface of a posterior vascular wall disposed opposite to the aperture void space of a puncture site in an anterior vascular wall of a blood vessel in a living subject; and at least one steering cable of predetermined length and composition rotably attached to said buttressing support member and suitable for aligned extension and passage on-demand from within a living subject through a posterior vascular wall, across a blood flow channel, and out an aperture void space of a puncture site in an anterior vascular wall into the ambient environment, whereby a vascular closure is guided into a controlled position at an aperture void space of a puncture site via said steering cable for an aligned closing and stabilized sealing of a vascular perforation after percutaneous puncture of a blood vessel.

A second aspect of the present invention is a closure apparatus for aligned closing and stabilized sealing of a vascular perforation after percutaneous puncture of a blood vessel in a living subject, said perforated blood vessel having an identifiable anterior vascular wall, a locally-sited puncture and aperture void space in the anterior vascular wall, a central blood flow channel, and an oppositely disposed posterior vascular wall, said closure apparatus comprising:

a closure guiding stabilizer suitable for on-demand aligned deployment within a living subject adjacent an exterior surface of a posterior vascular wall of a blood vessel after percutaneous puncture and for on-demand extension and passage in part from the aligned deployment within a living subject through a posterior vascular wall, across the blood flow channel, and out an aperture void space of a puncture site in an anterior vascular wall into the ambient environment, said closure guiding stabilizer being comprised of (i) a buttressing support member having predetermined dimensions and an elongated configuration suitable for on-demand placement via the vascular perforation adjacent an exterior surface of a posterior vascular wall disposed opposite to the aperture void space of a puncture site in an anterior vascular wall of a blood vessel in a living subject, and (ii) at least one steering cable of predetermined length and composition rotably attached to said buttressing support member and suitable for aligned extension and passage on-demand from within a living subject through a posterior vascular wall, across a blood flow channel, and out an aperture void space of a puncture site in an oppositely disposed anterior vascular wall into the ambient environment; and a vascular closure adapted for on-demand receiving of and juncture with said steering cable of said guiding stabilizer after placement of said buttressing support member in a living subject and extension of said steering cable from within a living subject into the ambient environment, said vascular closure being guided into a controlled position at an aperture void space via said steering cable for an aligned closing and stabilized sealing of a vascular perforation after percutaneous puncture of a blood vessel.

A third aspect of the present invention provides a kit apparatus for aligned closing and stabilized sealing of a vascular perforation after percutaneous puncture of a blood vessel in a living subject, said perforated blood vessel having an identifiable anterior vascular wall, a locally-sited puncture and aperture void space in the anterior vascular wall, a central blood flow channel, and an oppositely disposed posterior vascular wall, said kit apparatus comprising:

a multi-lumen needle suitable for percutaneous puncture of a blood vessel in a living subject, said needle being of fixed gauge and axial length, having discrete proximal and distal ends, and presenting at least first and second openings at the proximal end, at least first and second internal lumens of predetermined diameter which extend over most of the axial length of said needle, and at least first and second exit holes at divergent locations at the distal end of said needle, wherein said first exit hole at said distal end of said needle can be situated within a blood flow channel of a blood vessel when said needle is used for percutaneous puncture, and wherein said second exit hole at said distal end of said needle can be concurrently situated at an exterior surface of a posterior vascular wall of a blood vessel when said needle is used for percutaneous puncture;

a closure guiding stabilizer suitable for on-demand aligned deployment within a living subject adjacent an exterior surface of a posterior vascular wall of a blood vessel via said multi-lumen needle after percutaneous puncture and for on-demand extension and passage in part from the aligned deployment within a living subject through the posterior vascular wall, across the blood flow channel, and out the aperture void space of said puncture site in an anterior vascular wall into the ambient environment, said closure guiding stabilizer being comprised of (i) a buttressing support member having predetermined dimensions and an elongated configuration for on-demand placement via said multi-lumen needle adjacent an exterior surface of a posterior vascular wall disposed opposite to the aperture void space of a puncture site in the anterior vascular wall of a blood vessel in a living subject, and (ii) at least one steering cable of predetermined length and composition rotably attached to said buttressing support member and suitable for aligned extension and passage on-demand from within a living subject through a posterior vascular wall, across a blood flow channel, and out the aperture void space of said puncture site in an oppositely disposed anterior vascular wall into the ambient environment; and a vascular closure adapted for on-demand receiving of and juncture with said steering cable of said guiding stabilizer after aligned deployment in a living subject and extension of said steering cable into the ambient environment, said vascular closure being guided into a controlled position at an aperture void space via said steering cable for an aligned closing and stabilized sealing of a vascular perforation after percutaneous puncture of a blood vessel.

A fourth aspect of the present invention is a method for aligned closing and stabilized sealing of a vascular perforation after percutaneous puncture of a blood vessel in a living subject, said perforated blood vessel having an identifiable anterior vascular wall, a locally-sited puncture and aperture void space in the anterior vascular wall, a central blood flow channel, and an oppositely disposed posterior vascular wall, said method comprising the steps of:

obtaining a multi-lumen needle suitable for percutaneous puncture of a blood vessel in a living subject, said needle being of fixed gauge and axial length, having discrete proximal and distal ends, and presenting at least first and second openings at the proximal end, at least first and second internal lumens of predetermined diameter which extend over most of the axial length of said needle, and at least first and second exit holes at divergent locations at the distal end of said needle;

percutaneously puncturing a blood vessel in a living subject using said multi-lumen needle such that said first exit hole at the distal end of said needle becomes situated within the blood flow channel of the blood vessel and said second exit hole at the distal end of said needle becomes concurrently situated at an exterior surface of a posterior vascular wall of the blood vessel;

deploying a closure guiding stabilizer via said second exit hole of said multi-lumen needle in an aligned placement within a living subject adjacent to an exterior surface of the posterior vascular wall of the perforated blood vessel, said deployed closure guiding stabilizer being comprised of (i) a buttressing support member having predetermined dimensions and an elongated configuration for placement adjacent to the exterior surface of a portion of the posterior vascular wall disposed opposite to the aperture void space of the puncture site in the anterior vascular wall of a blood vessel in the living subject, and (ii) at least one steering cable rotably attached to said buttressing support member for aligned extension and passage on-demand through the posterior vascular wall, across the blood flow channel, and out the aperture void space of said puncture site in the oppositely disposed anterior vascular wall into the ambient environment;

extending said steering cable of said deployed closure guiding stabilizer via said multi-lumen needle through the posterior vascular wall, across the blood flow channel, and out the aperture void space of said puncture site in the oppositely disposed anterior vascular wall into the ambient environment;

procuring a vascular closure adapted for on-demand receiving of and juncture with said extended steering cable of said deployed closure guiding stabilizer; and joining said vascular closure to said extended steering cable as received in the ambient environment; and guiding said joined vascular closure into a controlled position within the aperture void space of the puncture site using said received steering cable for an aligned closing and stabilized sealing of the percutaneous perforation.

BRIEF DESCRIPTION OF FIGURES

The present invention can be more easily understood and fully appreciated when taken into conjunction with the accompanying drawing, in which:

FIGS. 1A–1F illustrate the essential steps of the modified Seldinger technique conventionally used in this art;

FIG. 4 is a perspective view of a preferred embodiment of a multi-lumen puncture needle;

FIG. 5 is an axial cross-section view of the multi-lumen puncture needle of FIG. 4;

FIGS. 6A, 6B, and 6C are transverse cross-sectional views of the multi-lumen puncture needle at the transverse axes XX', YY', and ZZ' respectively;

FIGS. 10–12 are preliminary manipulations wherein:

FIG. 10 is a cross-sectional view of the multi-lumen puncture needle and local anatomical site intended for percutaneous puncture using the present invention;

FIG. 11 is a cross-sectional view illustrating proper percutaneous puncture of a blood vessel using the apparatus and method of the present invention;

FIG. 12 is a cross-sectional view illustrating the placement of a guidewire via the multi-lumen puncture needle after the percutaneous puncture of a blood vessel shown by FIG. 11;

FIGS. 13–23 are a first series of interim manipulations wherein:

FIG. 13 is a cross-sectional view illustrating the introduction of a preferred closure guiding stabilizer through the multi-lumen puncture needle shown;

FIG. 14 is a cross-sectional view illustrating the advancement of a preferred closure guiding stabilizer within the multi-lumen puncture needle;

FIG. 15 is a cross-sectional view illustrating the deployment of a preferred closure guiding stabilizer outside the posterior vascular wall of the blood vessel shown;

FIG. 16 is a cross-sectional view illustrating the aligned placement of the deployed closure guiding stabilizer adjacent the penetration fracture in the posterior vascular wall after partial withdrawal of the puncture needle;

FIG. 17 is a cross-sectional view illustrating the aligned closure guiding stabilizer deployed adjacent the penetration fracture in the posterior vascular wall and the introduced guidewire after complete withdrawal of the puncture needle;

FIG. 18 is a cross-sectional view illustrating catheter and guidewire combination within the puncture site in the presence of the deployed and aligned closure guiding stabilizer;

FIG. 19 is a cross-sectional view illustrating the plug closure of FIG. 7 being guided by the deployed and aligned closure guiding stabilizer;

FIG. 20 is a cross-sectional view illustrating the plug closure of FIG. 7 being inserted into the puncture site while guided by the deployed and aligned closure guiding stabilizer;

FIG. 21 is a cross-sectional view illustrating the plug closure of FIG. 7 inserted in a controlled position for closing and sealing the vascular perforation after being guided by the deployed and aligned closure guiding stabilizer;

FIG. 22 is a cross-sectional view illustrating removal of the guidewire from the inserted closure shown by FIG. 21;

FIG. 23 is a cross-sectional view illustrating a completed aligned closing and stabilized sealing of the vascular perforation after percutaneous puncture of the blood vessel using the apparatus and method of the present invention;

FIGS. 24–28 are a second series of interim manipulations wherein:

FIG. 24 is a cross-sectional view illustrating the alternative anchor closure of FIG. 9 being guided into the puncture site using the deployed and aligned closure guiding stabilizer;

FIG. 25 is a cross-sectional view illustrating the anchor closure of FIG. 9 guided through the vascular perforation in the anterior vascular wall;

FIG. 26 is a cross-sectional view illustrating the placement of the anchor closure of FIG. 9 against the anterior vascular wall;

FIG. 27 is a cross-sectional view illustrating the removal of the guidewire from the percutaneous puncture after the anchor closure of FIG. 9 has been placed into a controlled position;

FIG. 28 is a cross-sectional view illustrating the aligned closing and stabilized sealing of the vascular perforation by the anchor closure of FIG. 9 after using the method and system of the present invention;

FIGS. 29–39 are a third series of interim manipulations wherein:

FIG. 29 is a cross-sectional view illustrating the introduction of the preferred closure guiding stabilizer of FIG. 3 into the multi-lumen puncture needle after percutaneous puncture of a chosen blood vessel;

FIG. 30 is a cross-sectional view illustrating the advancement of the closure guiding stabilizer of FIG. 3 within the multi-lumen needle towards the penetration fracture in the posterior vascular wall;

FIG. 31 is a cross-sectional view illustrating the deployment of the closure guiding stabilizer at the exterior surface of the posterior vascular wall;

FIG. 32 is a cross-sectional view illustrating the partial withdrawal of the puncture needle and the aligned placement of the deployed closure guiding stabilizer adjacent the penetration fracture in the posterior vascular wall;

FIG. 33 is a cross-sectional view illustrating the complete removal of the multi-lumen puncture needle from the puncture site after aligned placement of the deployed closure guiding stabilizer;

FIG. 34 is a cross-sectional view illustrating catheter and guidewire combination in the presence of an aligned and deployed closure guiding stabilizer;

FIG. 35 is a cross-sectional view illustrating the adapted plug closure of FIG. 8 being controllably guided through an introducer sheath using the aligned and deployed closure guiding stabilizer;

FIG. 36 is a cross-sectional view illustrating the adapted plug closure of FIG. 8 being controllably guided into the puncture site via the introducer sheath, using the aligned and deployed closure guiding stabilizer;

FIG. 37 is a cross-sectional view illustrating the controlled positioning of the adapted plug closure within the puncture site for closing and sealing the vascular perforation;

FIG. 38 is a cross-sectional view illustrating the properly positioned plug closure after removal of the introducer sheath while stabilized by the aligned and deployed closure guiding stabilizer; and FIG. 39 is a cross-sectional view illustrating the completed aligned closing and stabilizer sealing of the vascular perforation after percutaneous puncture.

DETAILED DESCRIPTION OF THE INVENTION

Figure 2A:
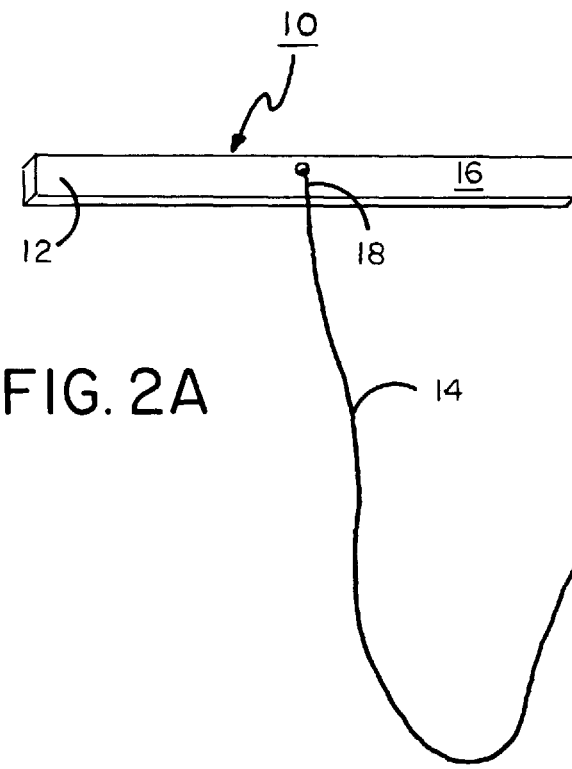
FIGS. 2A and 2B are overhead and side views of a first preferred embodiment of the closure guiding stabilizer comprising part of the present invention.

The present invention is an improvement in systems for closing and effectively sealing a vascular perforation and the aperture void space created by a percutaneous puncture of a blood vessel in a living subject. The chosen blood vessel, an artery or a vein, was intentionally punctured in order to perform either a diagnostic or an interventional catheterization procedure on a living patient; and after the catheterization procedure has been successfully completed, the vascular perforation and the aperture void space at the locally-sited puncture subsequently must be effectively closed and sealed to prevent serious bleeding and other medical complications. The present invention is thus a marked improvement in the means and manner of closing and sealing the aperture void space and the vascular perforation after percutaneous puncture of a blood vessel. The improvements provided by the present invention offer major benefits and unforeseen advantages to the physician or surgeon as well as to the patient. These advantages and benefits include the following:

1. The apparatus comprising the present invention is utilized in part during the percutaneous puncture technique, the modified Seldinger technique, which creates a vascular perforation in the chosen blood vessel. Thus, the means for effective closure and sealing of the puncture site are initiated and deployed as a part of the act of preparing and generating a vascular perforation suitable for the intended diagnostic or interventional catheterization procedure. The method of the present invention is thus singular and unique in that the means for achieving an aligned closing and stabilized sealing of the puncture site are in place before beginning or performing the desired catheterization procedure itself.

2. The present invention provides an aiding device, a closure apparatus, and a kit apparatus for guiding a vascular closure into a controlled position at an aperture void space of a puncture site for an aligned closing and stabilized sealing of a vascular perforation. The component parts of the present invention provide the means for alignment, stability, and effective control in the placement of a vascular closure in a degree which were not possible or foreseeable in the prior art.

3. The present invention, in the preferred embodiments, is comprised of bioabsorbible, biodegradable, or bioerodible materials which are resorbable by the body of the subject after deployment and use. Moreover, not only are all of the component parts of the invention biocompatible and predominantly biodegradable, the apparatus is most suitable for vascular usage using materials which have been previously approved for this purpose by the Food and Drug Administration.

4. The apparatus and method of the present invention can be employed with any artery or vein in the body of a living patient. The invention is particularly suitable for use with major arteries such as the femoral, the brachial, or axillary arteries. When used to close and seal a vascular perforation, the apparatus and methodology provides hemostasis after a controlled closure and sealing of the puncture site on the chosen blood vessel.

It will be noted that the apparatus comprising the present invention may be defined in the alternative as an aiding device, a closure apparatus, and a kit apparatus. The system and methodology preferably employs all of these articles for aligned closing and stabilized sealing of a vascular perforation. Accordingly, the detailed disclosure will present the invention as separate sections seriatim in which the articles and apparatus of the invention will be described; followed by the methodology using different embodiments of the apparatus to achieve effective closure of a percutaneous puncture site.

I. The Articles And Apparatus

In the present system for closure and sealing of a vascular perforation, three different types of articles are employed. These are a closure guiding stabilizer; a multi-lumen puncture needle; and a biocompatible vascular closure article. Each will be individually described below.

A. The closure guiding stabilizer:

The closure guiding stabilizer is an essential part of the invention and is an aiding apparatus or device for guiding and stabilizing a vascular closure into a vascular perforation after percutaneous puncture of a blood vessel in a living subject. The various embodiments of the closure guiding stabilizer, particularly as illustrated by FIGS. 2 and 3 respectively, are suitable for on-demand aligned deployment within a living subject at or adjacent to an exterior surface of the posterior vascular wall of a blood vessel after percutaneous puncture; and each is suitable for on-demand extension and passage in part from the aligned deployment within the living subject through the posterior vascular wall, across the blood flow channel, and out the aperture void space of the puncture site of the anterior vascular wall into the open ambient environment. One preferred embodiment of a closure guiding stabilizer is illustrated by FIG. 2.

As shown by FIG. 2, the closure guiding stabilizer 10 is comprised of a buttressing support member 12 having at least one steering cable 14. The buttressing support member 12 has predetermined dimensions and an elongated configuration suitable for on-demand placement adjacent an exterior surface of a posterior vascular wall (disposed oppositely to the aperture void space of a puncture site in a blood vessel of a living subject). Correspondingly, the steering cable 14 is also of predetermined thickness and length; has a proximal end 17 and a distal end 18; and is rotably attached to the buttressing support member 12. Each steering cable 14 is suitable for aligned extension and passage on-demand from within a living subject through a posterior vascular wall, across a blood flow channel, and out an aperture void space of a puncture site into the external ambient environment.

Figure 2B:
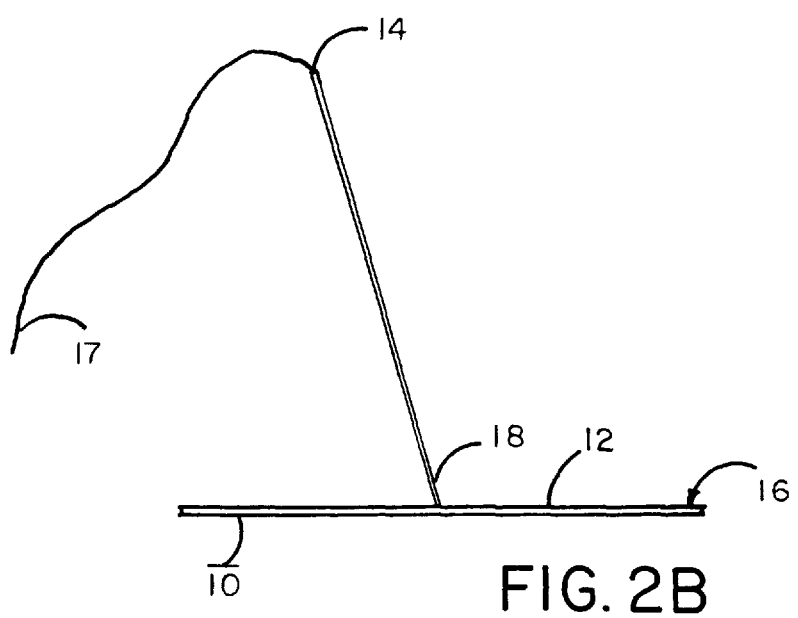

As seen in FIGS. 2A and 2B, a preferred embodiment of the buttressing support member 12 appears as a very narrow and thin, rectangularly shaped solid having planar external surfaces 16 and a minimal thickness. Typical dimensions for the buttressing support member would range from 1–10 millimeters in length, 0.3–1.0 millimeters in width, and 0.3–1.0 millimeters in thickness. Clearly however, it is expected that the exact dimensions will vary considerably with the lumen size for the puncturing needle described hereinafter and with the intended usage and positioning of the article. The composition of the buttressing support member 12 may vary considerably and includes biocompatible metals, metallic alloys and blends, polymers and polymeric mixtures, collagen, or any other type of material which is either intrinsically biocompatible or can be rendered biocompatible using conventional coatings or layerings to achieve biocompatibilty. In addition, the particular material constituting the buttressing support member may itself be biodegradable, bioresorbable, or non-erodible in accordance with the needs or wishes of the physician or surgeon. Thus, the buttressing support member may be composed of stainless steel, titanium, or a nickel-titanium alloy; of polymers such as polyethylene, polypropylene, polyvinyl pyrrolidine, polyvinyl acetate mixtures and the like; or of bioresorbable materials such as collagen and collagen containing mixtures.

In comparison, the single steering cable or multiple steering cables rotably attached to the buttressing support member are guiding lines and directional leaders by which a vascular closure is ultimately guided into a controlled position at an aperture void space of a puncture site. Note that the steering cable 14 shown in FIGS. 2A and 2B is of a predetermined length and thickness. Typical dimensions for the steering cable are a length of 10–20 inches and a thickness (or diameter) of 0.005–0.050 inches. The composition of the steering cable may vary from conventionally known suture materials (which are either resorbable or non-resorbable), and may alternatively comprise metals, metallic alloys, and metallic laminates which are biocompatible.

Figure 3A:
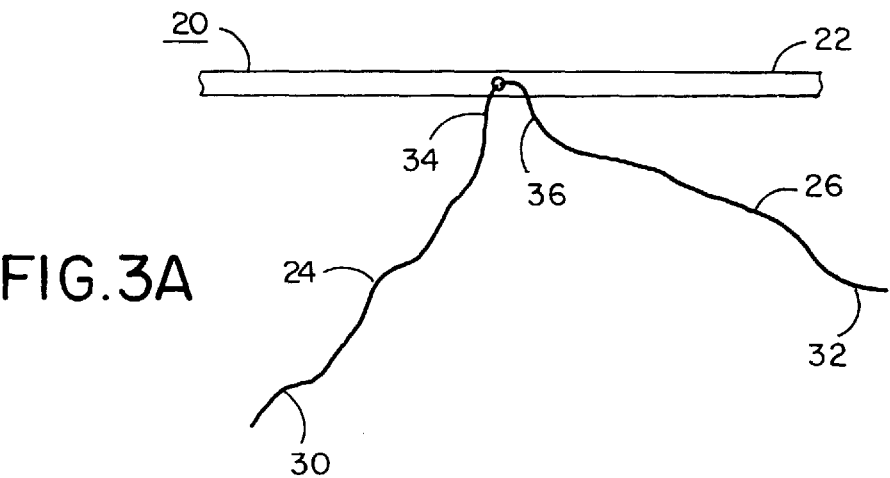
FIGS. 3A and 3B are overhead and side views of a second preferred embodiment of the closure guiding stabilizer comprising part of the present invention.
Figure 3B:
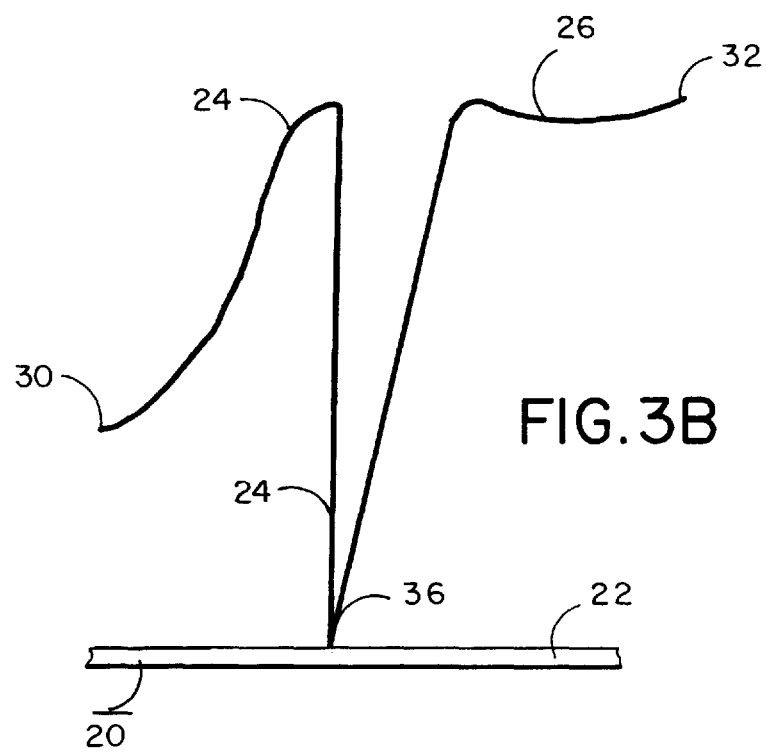

A second preferred embodiment of the closure guiding stabilizer is illustrated by FIGS. 3A and 3B respectively. As shown therein, the closure guiding stabilizer 20 comprises a rod-shaped and hollow buttressing support member 22 and two steering cables 24, 26 having proximal ends 30, 32 and distal ends 34, 36. The buttressing support member 22, being internally hollow and rod-shaped in overall configuration, is desirable as a lighter weight bar format; and the two steering cables 24, 26 each act as guiding lines and directional leaders to place a vascular closure into a controlled position at a puncture site for an aligned closing and stabilized sealing of the vascular perforation of the blood vessel. The manufacturer or intended user retains the choice of materials and compositions for the buttressing support member 22 and the steering cables 24, 26 as previously described herein.

The closure guiding stabilizer 20 is suitable for on-demand aligned deployment adjacent an exterior surface of the posterior vascular wall of a blood vessel after percutaneous puncture; and the steering cables 24 and 26 rotably attached to the buttressing support member 22 are suitable for aligned extension and passage on-demand through the posterior vascular wall, across the blood flow channel of the vessel, and out the aperture void space of a puncture site into the external ambient environment.

B. The multi-lumen puncture needle:

A requisite component of the kit apparatus comprising the present invention is a multi-lumen needle suitable for percutaneous puncture of a blood vessel in a living subject. This puncture needle is of fixed gauge and axial length; has discrete proximal and distal ends; and presents at least first and second openings at the proximal end, at least first and second internal lumens of predetermined diameter which extend over most of the axial length of the needle, and at least first and second exit holes at divergent locations at the distal end of the needle. It is a requirement of each embodiment for this multi-lumen needle that it function in a manner where the first exit hole at the distal end of the needle can be situated within the central blood flow channel of a blood vessel when the needle is used for percutaneous puncture; and also that the second exit hole located at the distal end of the needle can be concurrently situated at an exterior surface of the posterior vascular wall of the blood vessel when the needle is used for percutaneous puncture.

A preferred embodiment of the multi-lumen puncture needle is illustrated by FIGS. 4, 5, and 6 respectively. The cross-sectional longitudinal view of the needle illustrated by FIG. 5 is used repeatedly herein to demonstrate the methodology and system of the apparatus. The overhead axial view provided by FIG. 4 and the individual cross-sectional transverse views provided by FIGS. 6A, 6B, and 6C respectively provide additional information and prospective for the needle as a whole.

As illustrated by FIGS. 4–6 collectively, a dual-lumen puncture needle 40 is shown having a preferred length of 5–20 centimeters and a preferred gauge size ranging from 20–14 G. The dual-lumen puncture needle has a proximal end 42, a distal end 44, an overall axial external surface 46, and a puncturing distal tip 48. In addition, the puncturing needle 40 has two internal bores or lumens. The anterior bore 50 includes an anterior opening 52 at the proximal end; an anterior internal lumen 54 extending over most of the axial length of the needle; and an anterior exit hole 56 at the distal end 44 of the needle. Similarly, the posterior bore 60 provides an posterior opening 62 at the proximal end 42 of the needle; a posterior internal lumen 64 extending over most of the axial length of the needle 40; and a posterior exit hole 66 located at the distal end 44 of the needle.

It will be noted and appreciated that while the openings 52, 62 for the anterior and posterior bores 50, 60 are preferably positioned in parallel at the proximal end 42 of the puncture needle 40, and that the anterior bore 50 and the posterior bore 60 are similarly positioned in parallel over most of the axial length of the needle, the exit holes 56, 66 appear at divergent and opposite locations at the distal end 44 of the puncture needle 40. Such divergent and opposing locations for the anterior and posterior exit holes is a necessary feature of each embodiment of the puncture needle 40.

The overall structure for the dual-lumen puncture needle 40 intends that the anterior exit hole 56 be situated within the central blood flow channel of a blood vessel when the needle is properly used to achieve percutaneous puncture. Similarly, it is also intended that the posterior exit hole 66 of the needle be concurrently situated at an exterior surface of the posterior vascular wall of a blood vessel when the needle is properly used for percutaneous puncture. This functional outcome is achieved by the divergent and opposing location for the anterior exit hole 56 in comparison to the posterior exit hole 66, both of which are located at the distal end 44 of the puncture needle 40. Also, it is intended that the anterior bore 50 will serve primarily as an access for guidewire placement within the perforated blood vessel; and that the anterior internal lumen 54 terminate at the exit hole 56 located approximately 5–15 millimeters above the puncturing distal tip 48 of the needle 40. Thus, when the puncture needle 40 is used properly to achieve percutaneous puncture of a chosen blood vessel, the anterior exit hole 56 is positioned within the blood flow channel of the blood vessel—which allows the blood to flow through the anterior bore 50 and to spurt out the anterior opening 52. The guidewire placement and passage through the anterior bore 50 thus serves to direct and introduce the catheterization procedure as needed or desired.

In comparison, the primary function of the posterior bore 60 is to allow the intentional insertion and passage of a closure guiding stabilizer through the posterior internal lumen 64 for precise deployment and outside the posterior wall of the perforated blood vessel. The divergent and opposite location of the posterior exit hole 66 at the distal end of the needle, in relation to the anterior exit hole 56, provides for concurrent aligned placement of a closure guiding stabilizer into the soft tissue of the living subject adjacent to the posterior vascular wall of the perforated blood vessel.

The dual functions of the puncture needle 40 to be achieved by the anterior bore 50 and the posterior bore 60 concurrently are shown in transverse cross-sectional views by FIG. 6; in which FIG. 6A is a transverse view along the axis XX', FIG. 6B is a transverse view along the axis YY', and FIG. 6C is a transverse view along the axis ZZ' of FIG. 4. These transverse cross-sectional views provided by FIG. 6 reveal the parallel setting of the anterior bore 50 and the posterior bore 60 as well as the divergence of the anterior exit hole 56 from the posterior exit hole 66 at opposite sides of the puncturing needle 40. The structural requirements and features illustrated by FIGS. 4–6 thus collectively illustrate the dual function and capabilities of the puncture needle 40 for concurrent placement of the anterior exit hole 56 and the posterior exit hole 66 at different aligned positions within a blood vessel when the puncture needle 40 is properly used for percutaneous puncture.

C. The vascular closures:

The vascular closures comprise biocompatible articles intended to be inserted into the aperture void space of a puncture site; and function as stoppers or plugs at or adjacent to the perforation in the anterior vascular wall by filling or physically blocking the aperture void space of the puncture in the perforated blood vessel. These vascular closures are conventionally known in the art, but have been modified in structure and form and adapted for on-demand receiving of and juncture with the extended steering cables of the deployed closure guiding stabilizer then positioned outside the posterior vascular wall of the perforated blood vessel. The adapted vascular closure will be joined to at least one extended steering cable after it is received within the external ambient environment; and the received steering cable(s) is employed as a guiding line and directional leader to place the joined vascular closure into a controlled position within the aperture void space of the puncture site. The received and joined steering cable(s) thus controls the placement of the vascular closure and controls the insertion of the joined vascular closure to achieve a singular aligned closing and stabilized sealing of the percutaneous perforation in the body of the living subject.

Figure 8:
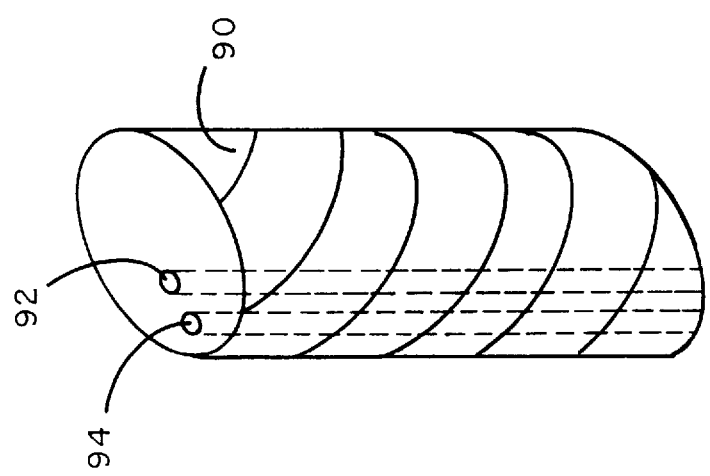
FIG. 8 is a perspective view of another adapted cylindrical-shaped plug closure suitable for use in the method and system of the present invention.
Figure 7:
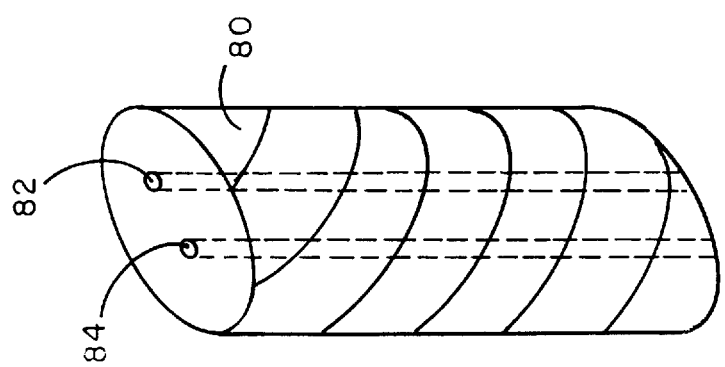
FIG. 7 is a perspective view of one adapted cylindrical-shaped plug closure suitable for use in the method and system of the present invention.
Figure 9A:
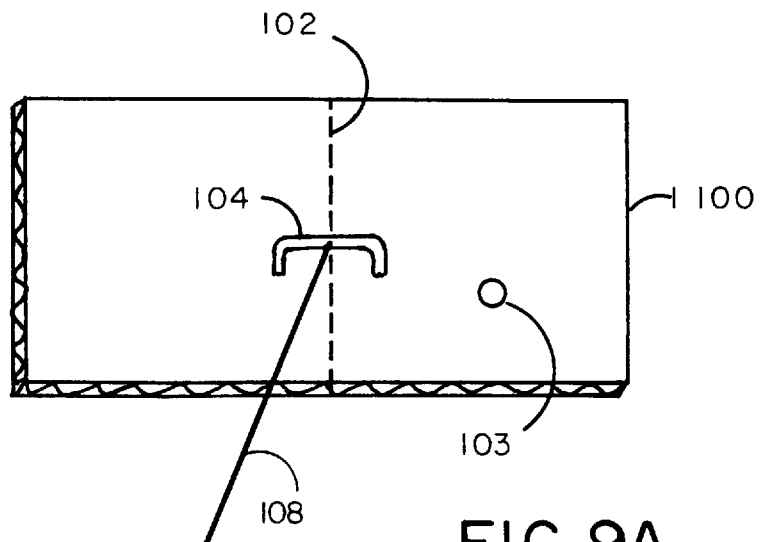
FIGS. 9A and 9B are overhead and side views of a conventionally known membrane/plate anchor closure suitable for use in the method and system of the present invention.
Figure 9B:
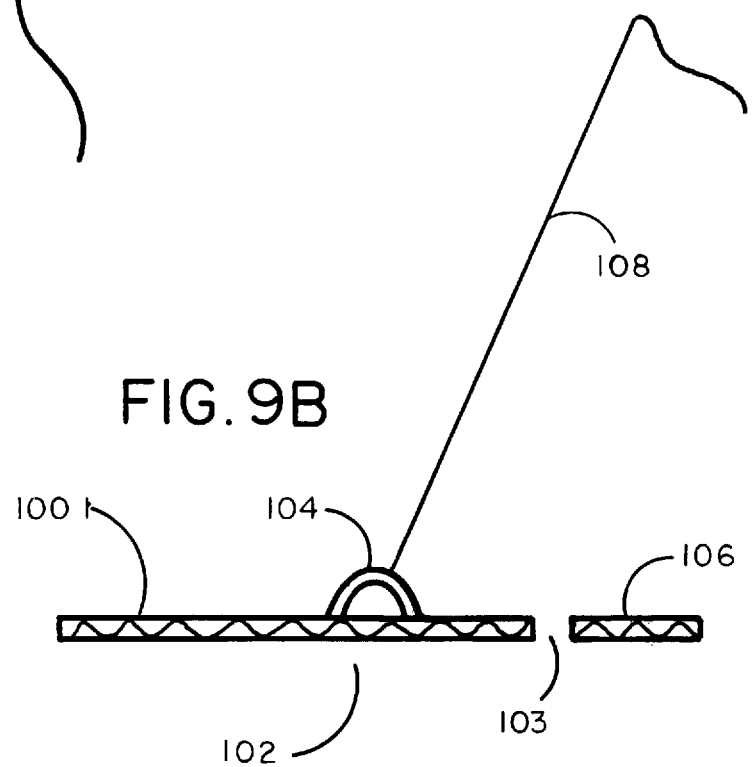

Examples of adapted vascular closures are illustrated by FIGS. 7 and 8 for a cylindrical plug closure and by FIGS. 9A and 9B for a membrane/plate type of anchoring closure device. Each type of closure device will be described individually.

As shown within FIGS. 7 and 8 respectively, the adapted closure device is a solid cylindrically-shaped plug of predetermined dimensions; and these embodiments are represented by a preferred diameter of 1.5–6.0 millimeters and a preferred length of 1–90 millimeters. The solid plug closure type is formed using a bioerodible or bioresorbable material; and is typically a material chosen from the group consisting of purified degradable human or bovine collagen, a bioresorbable polymer, a collagen polymer, and a gelatin sponge composition (such as Gelfoam).

Each embodiment of the solid plug closure has one or more passageways extending through the length of the closure suitable for receiving and joining with the steering cable of the deployed closure guiding stabilizer in-vivo. Positioning of these passageways will vary. Accordingly, as shown by FIG. 7 the cylindrical solid plug 80 has two passageways 82, 84 which are spaced apart from each other but extend through the axial length of the plug itself. In comparison, FIG. 8 shows a solid cylindrical plug 90 having multiple passageways 92, 94 which are situated at one side of the plug mass for on-demand receiving and juncture with the extended steering cable of the deployed closure guiding stabilizer. After the vascular closures have been guided into a controlled position within the aperture void space of the puncture site and achieved an aligned closing and stabilized sealing of the percutaneous perforation of the blood vessel, hemostasis will exist for the perforation. The collagen or other bioerodible or bioresorbable material will dry in position over time; and, in the preferred embodiments, will eventually be completely resorbed by the body of the patient in due course of natural processes.

An alternative form of vascular closure is that membrane/plate anchor type of vascular closure illustrated by FIGS. 9A and 9B respectively. The anchor type of closure is intended to be inserted through the puncture site and to be positioned against the internal surface of the anterior vascular wall adjacent the aperture void space of the puncture site. The anchor closure being positioned inside the blood flow channel of the blood vessel against the vascular puncture, thereby acts as a physical anchor barrier and blockage closure when properly situated. This conventional anchor type of vascular closure is also well known in the prior art; but has been modified and adapted to receive and to become joined with the steering cable(s) of the closure guiding stabilizer described previously herein.

The anchor closure 100 typically can be bent along a flexible line 102 for ease of insertion into the perforation has a thru hole 103 for passage of a steering cable from the closure guiding stabilizer; and has an attachment collar 104 joined to the external surface 106 of the anchor. Joined to the attachment collar 104 is an anchoring line 108 of predetermined length. The purpose of the anchoring line 108 is to hold the membrane/plate anchor 100 in place against the interior surface of the perforated blood vessel; and to be extended from the blood flow channel through the aperture void space of the puncture site into the external ambient environment.

The adaptation and modification of this conventionally known anchor construction allows this conventionally known type of anchoring closure to be used as an alternative closure means with the present invention. The modified closure can therefore be advantageously employed for an aligned closing and stabilized sealing of a vascular perforation in a controlled manner not previously available before in this art.

II. The System And Method Of Aligned Closing And Stabilized Sealing

The system and method of the present invention utilizes the apparatus and modified closures in a series of prescribed manipulative steps and which provide the surgeon or physician with safe and reliable means for closing and effectively sealing a vascular perforation of a blood vessel after percutaneous puncture and completion of the intended catheterization procedure. The system and method of the present invention are generally applicable and suitable for use with any blood vessel, particularly major arteries and veins commonly chosen for a specific catheterization procedure which is necessary or advantageous for that patient. Several unique features of the system and methodology, however, should be particularly noted and recognized for its uniqueness and singularity.

The apparatus of the present invention described previously herein is utilized as part of the modified Seldinger technique for achieving successful percutaneous puncture and vascular perforation of a chosen blood vessel. The methodology and system utilizes and employs the novel apparatus initially at the beginning of the percutaneous puncture technique; and in this manner, the apparatus for subsequent closing and sealing of the vascular perforation is deployed, positioned, and aligned at the onset and well before the insertion of the catheter itself into the blood vessel.

Also, for purposes of illustration, and ease of understanding, a single major blood vessel will be described and referred to repeatedly as an illustrative example in the detailed description herein. It will be expressly understood, however, that this repeated reference to a single blood vessel and local anatomical site is presented solely for purposes of clarity and illustration; and that the identified blood vessel is merely one example of the many other types, sizes, and locations of blood vessels generally to be found at different anatomical sites throughout the body of a living patient. For descriptive purposes, however, the femoral artery will serve as the exemplified blood vessel of choice. The anatomical description presented below will thus conform to the true features and location within the human body where the femoral artery is normally to be found.

In addition, the preliminary steps of the present system and method described hereinafter and illustrated by FIGS. 10, 11, and 12 respectively, represent the common and customary Seldinger technique as modified using the apparatus of the present invention. It is intended and expected that all normal universal precautions, proper medical and surgical technique, and other safeguards in the operating room will be maintained in accordance with good and standard medical practices to date. Similarly, all conventional diagnostic and interventional catheterization procedures are suitable and intended for use with the modified Seldinger technique described herein which employs the apparatus of the present invention to achieve an aligned closing and stabilized sealing of the vascular perforation upon successful completion of the catheterization procedure itself.

The preliminary steps of the system and method

Using sterile technique, 2% lidocaine is injected superficially to produce a wheal at the puncture site and more deeply lateral and medial to the arterial pulse. A small superficial skin incision is made directly over the artery with a #11 scalpel blade and this opening is then widened with a hemostat to provide a space wide enough to accept the designated catheter. The skin nick should be made directly over the point of maximal impulse to assure that the needle enters the artery centrally. Eccentric puncture increases the risk of guidewire induced dissection, misdirection of the guidewire, and arteriovenous fistula formation. In addition, it may be more difficult to control bleeding after the procedure if the entrance site is located on the medial or lateral walls of the artery. Furthermore, when the skin nick is not directly over the central position of the artery, the chances of successful puncture are reduced as the initiation point does not coincide with the course of the vessel at the puncture site.

The choice of puncture site should be based upon the vascular examination, aim of the study and operator experience. A general rule is that the access site should be as close as possible to the area of interest in order to allow for optimal manipulation. For most of catheterization procedures, the retrograde femoral approach is preferred whenever possible. In the patient with suspected infrainguinal disease in whom both femoral pulses are strong, the less diseased leg should be punctured. This will preserve the groin on the diseased side for subsequent percutaneous or surgical treatment. If one femoral pulse is absent, the other side should be used. If both are dampened but palpable, the stronger pulse should be punctured.

The common femoral artery is ideal for percutaneous puncture because it is large, superficial, easily accessible and lies anteriorly to the femoral head which provides excellent support during manual hemostasis. The common femoral artery extends between the origin of the deep circumflex iliac artery and the origins of the superficial femoral and deep femoral arteries. The origin of the deep circumflex iliac artery corresponds to the location of the inguinal ligament. Puncture above this point carries the risk of retroperitoneal hemorrhage. Puncture below the common femoral arterial bifurcation increases the risk of pseudoaneurysm and arteriovenous fistula formation. Therefore, the puncture site should be localized appropriately. The location of the inguinal ligament can be determined by an imaginary line drawn between the anterior superior iliac spine and the pubic eminence. Puncture several centimeters below this line will in most cases be accurate and safe. The inguinal crease lies at this level and is preferred by many angiographers as a landmark for puncture.

Once the puncture site is chosen, the femoral artery is stabilized by placing a finger above and below the puncture site. Alternately, two fingers may be placed above the pulse. The apparatus of the present invention is then utilized place of conventional instruments during the carrying-out of the modified Seldinger technique. This is illustrated by FIGS. 10, 11, and 12 respectively.

Figure 39:
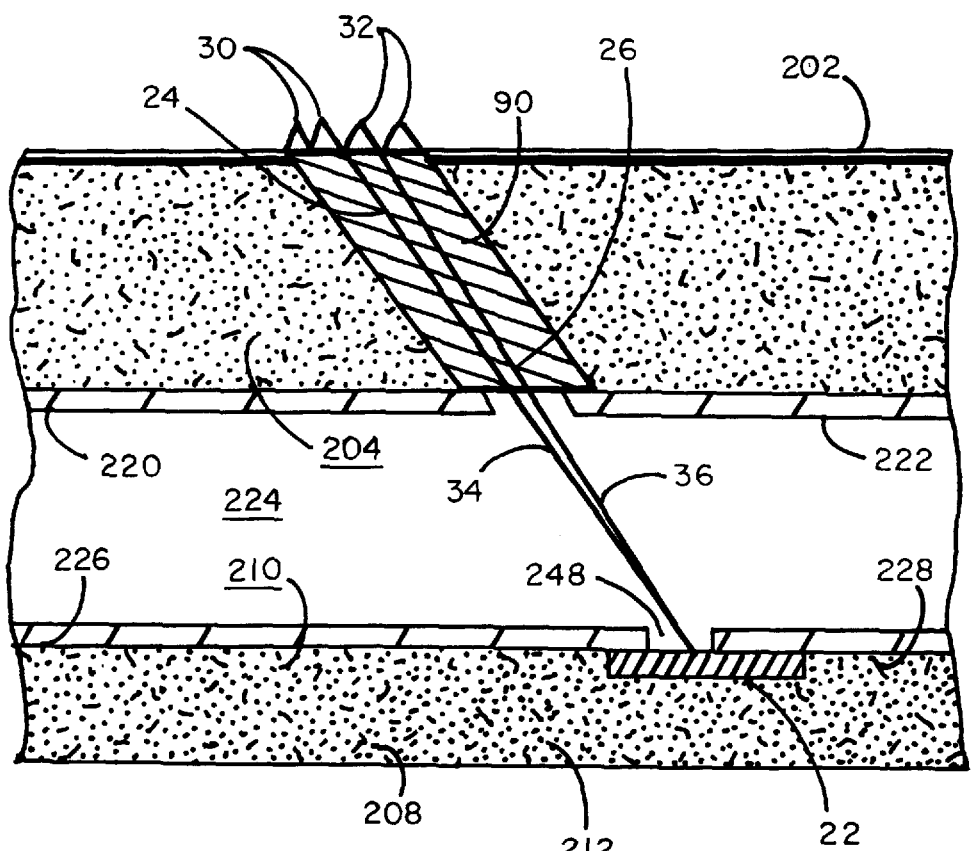

It will be appreciated that all of the figures beginning with FIG. 10 and ending with FIG. 39 present cross-sectional views of the local anatomical site of the living subject as well as cross-sectional views of the apparatus employed as part of the overall methodology and system. Such cross-sectional views present far clearer illustrations of the critical and essential events which occur during performance of the method as a whole; and offer a more complete perception of the apparatus and the manner in which it is employed during the manipulations themselves.

Figure 11:
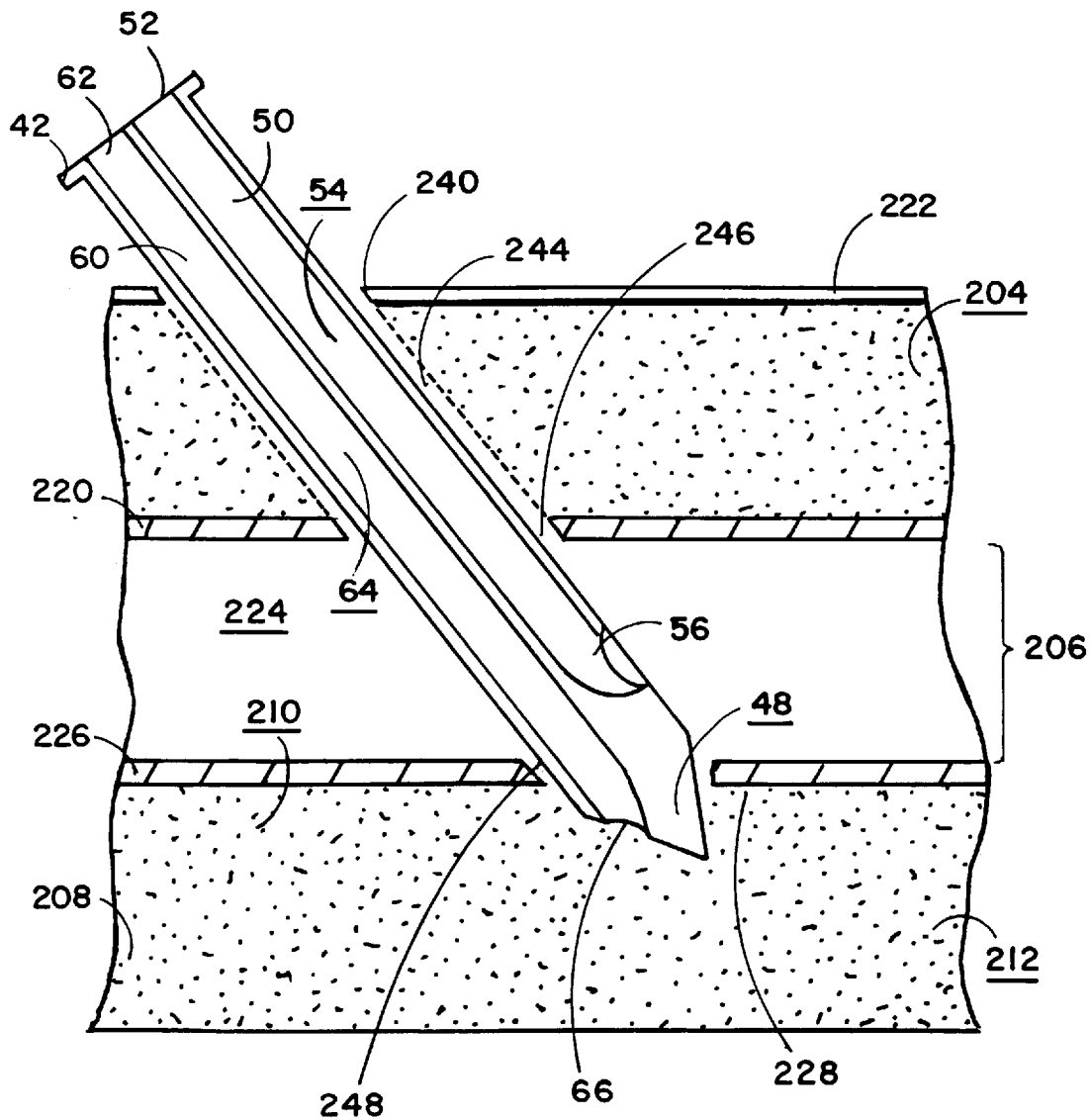
Figure 12:
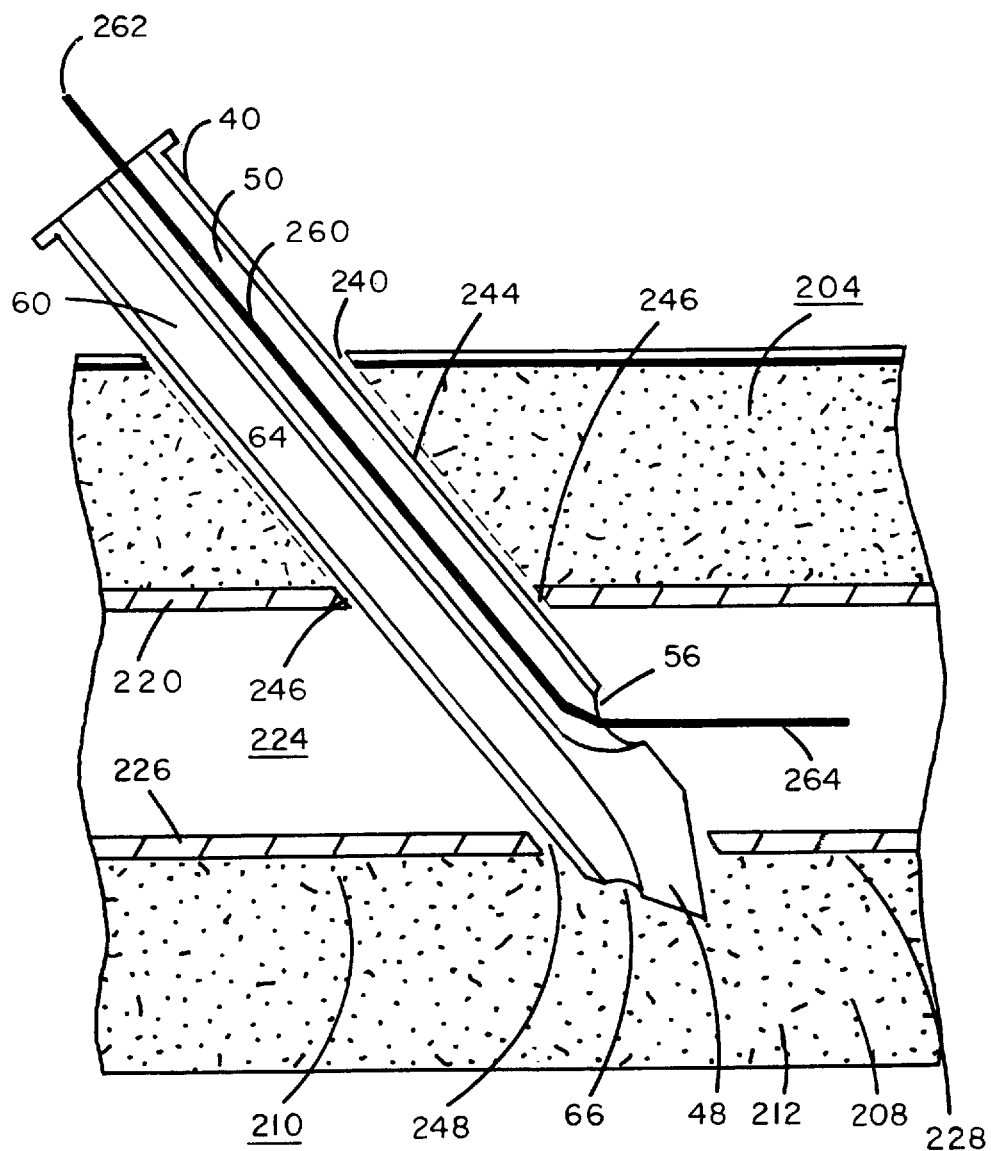

As shown by FIGS. 10, 11, and 12, individually and collectively, the local anatomical site 200 appears in cross-sectional view as the skin 202 including the epidermis and dermis; the superficial tissue layer 204 immediately beneath the skin and extending generally to the chosen blood vessel, the common femoral artery; the major blood vessel 206 itself; and the deeper tissue 208 including the local tissue 210 adjacent the blood vessel and the distant tissue 212. The major blood vessel 206, the femoral artery, is constituted of an anterior vascular wall 220, a central blood flow channel 224, and a posterior vascular wall 226. The interior surface 222 of the anterior vascular wall 220 is identified as is the external surface 228 of the posterior vascular wall 226.

At the local anatomical site 200, the dual-lumen puncture needle 40 is positioned. This multi-lumen needle has been described in detail previously herein and is illustrated by FIGS. 4–6 respectively in detail.

As shown by FIG. 11, the puncturing distal tip 48 of the dual-lumen needle 40 is passed through the skin nick forming a puncture site 240. As the needle is advanced slowly through the skin 222, it is passed through the superficial tissue layer 204 at about a 45–60 degree angle relative to the anticipated axis of the femoral artery 206. The puncturing distal tip 48 perforates the anterior vascular wall 220; is advanced across the central blood flow channel 224 of the artery 206; and continues forward until the puncturing distal tip fractures and penetrates the posterior vascular wall 226 to lie in intimate contact with the local tissue 210 of the deeper tissue layer 208. The overall effect and consequence of properly introducing the dual-lumen puncture needle 40 is to create: a puncture site 240 through the skin 222; an aperture void space 244 through the thickness of the superficial tissue layer 204; a perforation 246 in the anterior vascular wall 220; and a penetration fracture 248 through the posterior vascular wall 226. All of these events, consequences, and identifiable anatomical changes are the expected and intended result of properly inserting the dual-lumen puncture needle through the skin nick via the modified Seldinger technique for achieving percutaneous puncture of a chosen blood vessel.

In addition, the proper placement of the puncture needle 40 and the correct positioning of its structural elements is illustrated by FIGS. 11 and 12 respectively. As one direct outcome of proper insertion for the puncture needle 40, the anterior bore 50 is placed in fluid communication with the central blood flow channel 224 of the femoral artery 206. Thus, as the distal tip 48 passes into the blood channel 224, pulsatile arterial blood flows through the anterior exit hole 56, flows through the anterior internal lumen 54, and flows out the anterior opening 52 at the proximal end 42 of the needle 40. During performance of the medical procedure, it is expected that the puncture needle 40 will be advanced, then slightly withdrawn, and then advanced again to find the best and most suitable positioning such that the anterior exit hole 56 remains continuously in direct contact with the blood of the femoral artery. Radiographic imaging will aid and assist the physician or surgeon in finding the most optimal placement or access to and blood flow communication with the central flow channel of the blood vessel.

As a concomitant outcome and concurrent event with the proper positioning of the anterior bore 50 within the central blood flow channel 224, the posterior bore 60 of the needle 40 is placed in direct communication with the penetration fracture 248 of the posterior vascular wall 226; and is in intimate contact with the local tissue 210 adjacent the external surface 228 of the posterior vascular wall 226. Thus, by the act of advancing the puncture needle 40 properly during the percutaneous puncture of a chosen blood vessel, the posterior bore 60 is concomitantly and concurrently in direct communication with and has access to the deeper tissue layer 212 beneath the blood vessel 206, the exterior surface 228 of the posterior vascular wall, and the penetration fracture 248 extending through the thickness of the posterior vascular wall 226.

It is an essential feature and critical requirement of the system and methodology comprising the present invention that the proper positioning of the puncture needle (as shown by FIG. 11) is the desired, proper, and intended outcome of using the dual-lumen puncture needle for percutaneous puncture of a blood vessel. The adaptation of the Seldinger technique thus requires and demands not only the use of a multi-lumen puncture needle; but also that the puncture needle be employed properly and positioned correctly in the manner illustrated by FIGS. 11 and 12 respectively. All conventionally known imaging and radiographic aids should be employed to insure that the puncture needle 40 becomes placed in the desired position; and provides access for the anterior bore 50 to the central blood flow channel concurrent with the access of the posterior bore 60 to the exterior surface of the posterior vascular wall and the deeper tissue layer surrounding and supporting the posterior vascular wall of the blood vessel.

Once properly positioned, a radioopaque guidewire 260 (typically 0.010–0.035 inches in thickness) is inserted into and passed through the anterior bore 50 into the central blood flow channel 224 of the femoral artery 206. The distal end 262 of the guidewire 260 is inserted through the anterior opening 52, is passed through the internal lumen 54, and is pushed out the anterior exit hole 56 into the lumen of the blood vessel. The proximal end 264 remains in the external ambient environment. The guidewire 260 is the conventionally known and employed means by which the catheterization procedure is subsequently achieved.

A. A first preferred apparatus embodiment and method of closure

The first preferred apparatus embodiment and method of closure utilizes the closure guiding stabilizer illustrated by FIGS. 2A and 2B respectively and described in detail previously herein. The manner of apparatus deployment and manner of closure is illustrated by FIGS. 13–23 respectively. A first series of interim manipulations: deployment and placement of the closure guiding stabilizer This first interim sequence of manipulations begins after the puncturing needle 40 has been properly used for percutaneous perforation of a chosen blood vessel and the guidewire has been introduced through the anterior bore of the inserted puncture needle and has been introduced into the central blood flow channel of the chosen blood vessel. The act of deployment begins after the preliminary series of manipulations have been completed to the satisfaction of the physician or surgeon; and radiographic imaging has assured the physician or surgeon that a proper positioning of the needle has occurred.

Figure 13:
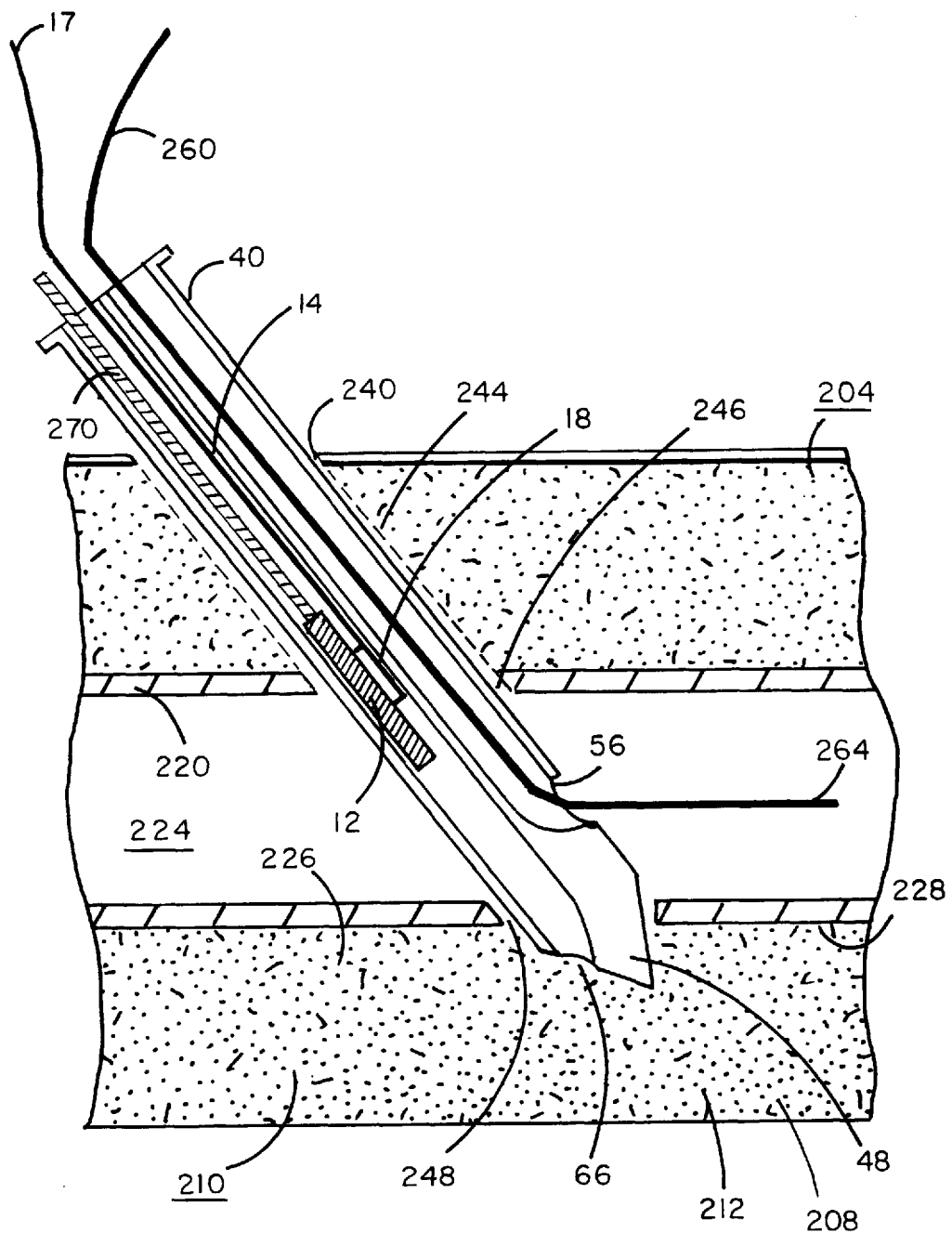
Figure 14:
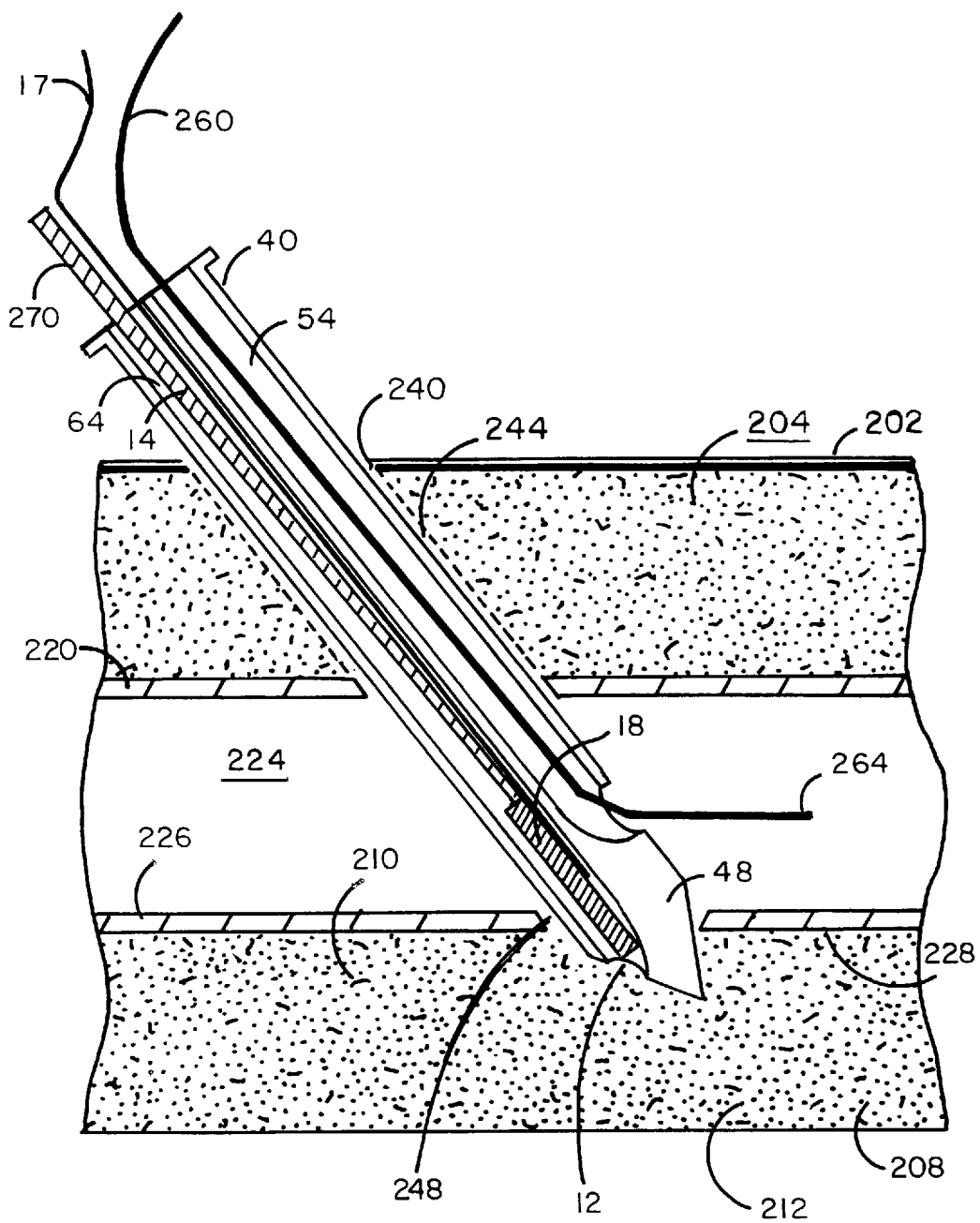

As shown by FIG. 13, the closure guiding stabilizer 10 (comprising a buttressing support member 12 and a single steering cable 14) is inserted into the posterior opening 62 of the posterior bore 60; and is advanced through the internal posterior lumen 64 towards the distal end 44 of the puncture needle 40. The closure guiding stabilizer 10 within the bore 60 is assisted in its advancement and migration by a thin, small diameter pusher rod 270 (typically 0.006–0.025 inches in thickness). The pusher rod 270 pushes and advances the closure guiding stabilizer 10 in a simple, rapid, and consistent manner towards the posterior exit hole 66, which is then situated at the external surface 228 of the posterior vascular wall 226. This is shown by FIG. 14.

Figure 15:
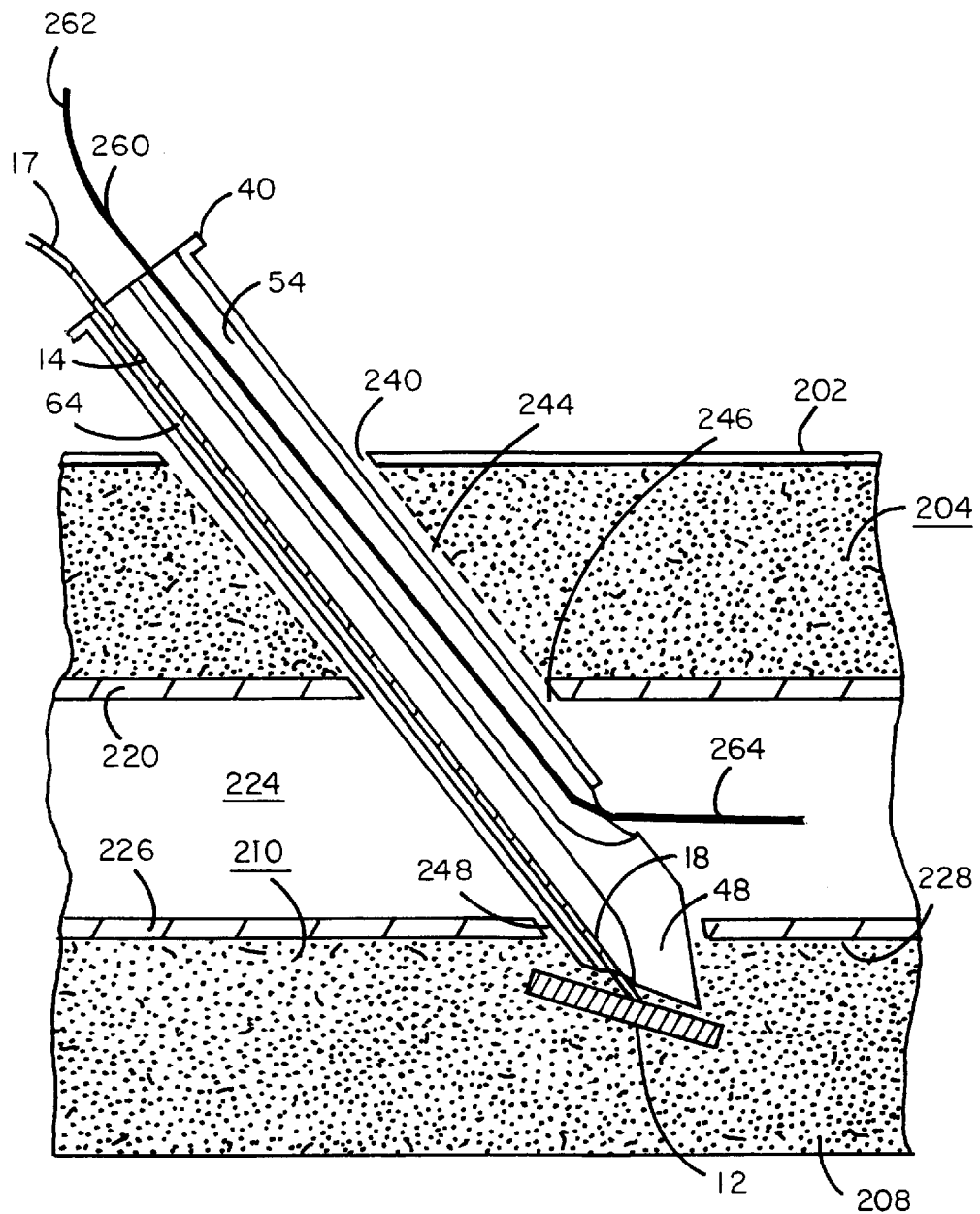

The closure guiding stabilizer 10 is then pushed out through the posterior exit hole 66 into the local tissue 210 adjacent the penetration fracture 248 in the posterior vascular wall 226. As shown by FIG. 15, the buttressing support member 12 is deployed outside the distal end 44 of the puncturing needle 40 such that the buttressing support member 12 lies adjacent the penetration fracture 248 of the posterior vascular wall and is held in this position by the local tissue 210 adjacent the penetration fracture itself. Equally important, it will be seen and recognized that the steering cable 14 (rotably attached to the buttressing support member 12) remains within the internal lumen 64 of the posterior bore 60 of the puncture needle 40; and that the steering cable lies along the axial length of the posterior bore 60 such that the proximal end 17 of the steering cable 14 extends into the external ambient environment—while the distal end 18 of the steering cable 14 remains securely linked and rotably attached to the deployed buttressing support member 12 at the exterior surface 248 of the posterior vascular wall 226.

Figure 16:
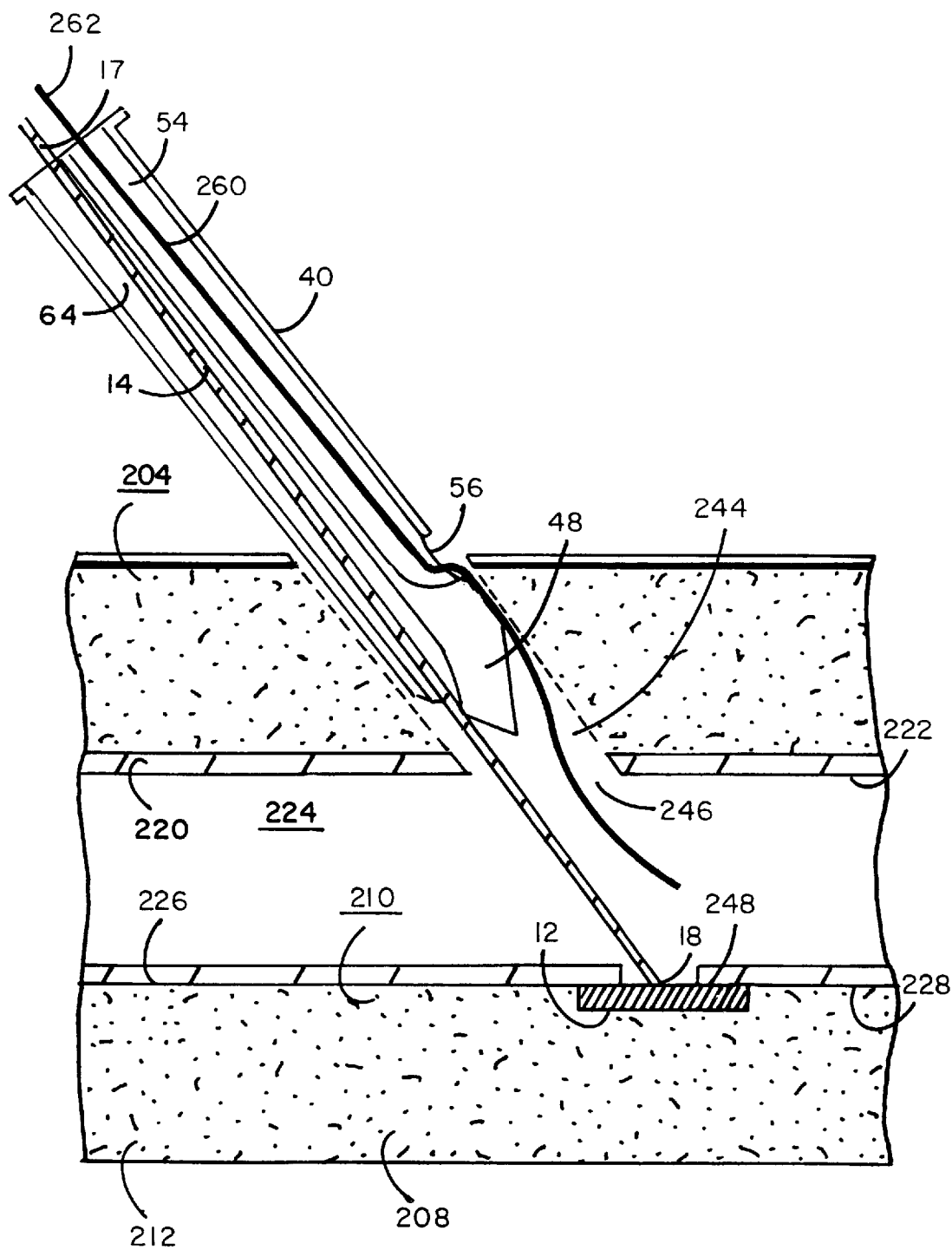

Desirably, the introduced puncture needle 40 is then partially withdrawn by the physician or surgeon towards the skin; preferably, the puncture needle is withdrawn in its original path, but in the reverse direction towards the skin surface until the distal cutting tip 48 has come to rest in the aperture void space 244 of the superficial tissue layer 204. This is shown by FIG. 16. This partial withdrawal of the puncture needle from its deepest point of insertion withdraws not only the posterior bore 60 but also the anterior bore 50 in which the guidewire 260 remains positioned.

Moreover, at the discretion of the physician or surgeon as the puncture needle 40 is partially withdrawn, the physician or surgeon then pulls on the exposed steering cable end, thereby placing the deployed buttressing support member 12 into an aligned position against the posterior vascular wall 226 adjacent the penetration fracture 248. This act of alignment places the deployed buttressing support member against the external surface 228 of the posterior vascular wall 226; and the aligned buttressing support member is held in this aligned deployment position by the tension on the steering cable 14 which is held under tension force by the physician or surgeon in the external ambient environment.

Figure 17:
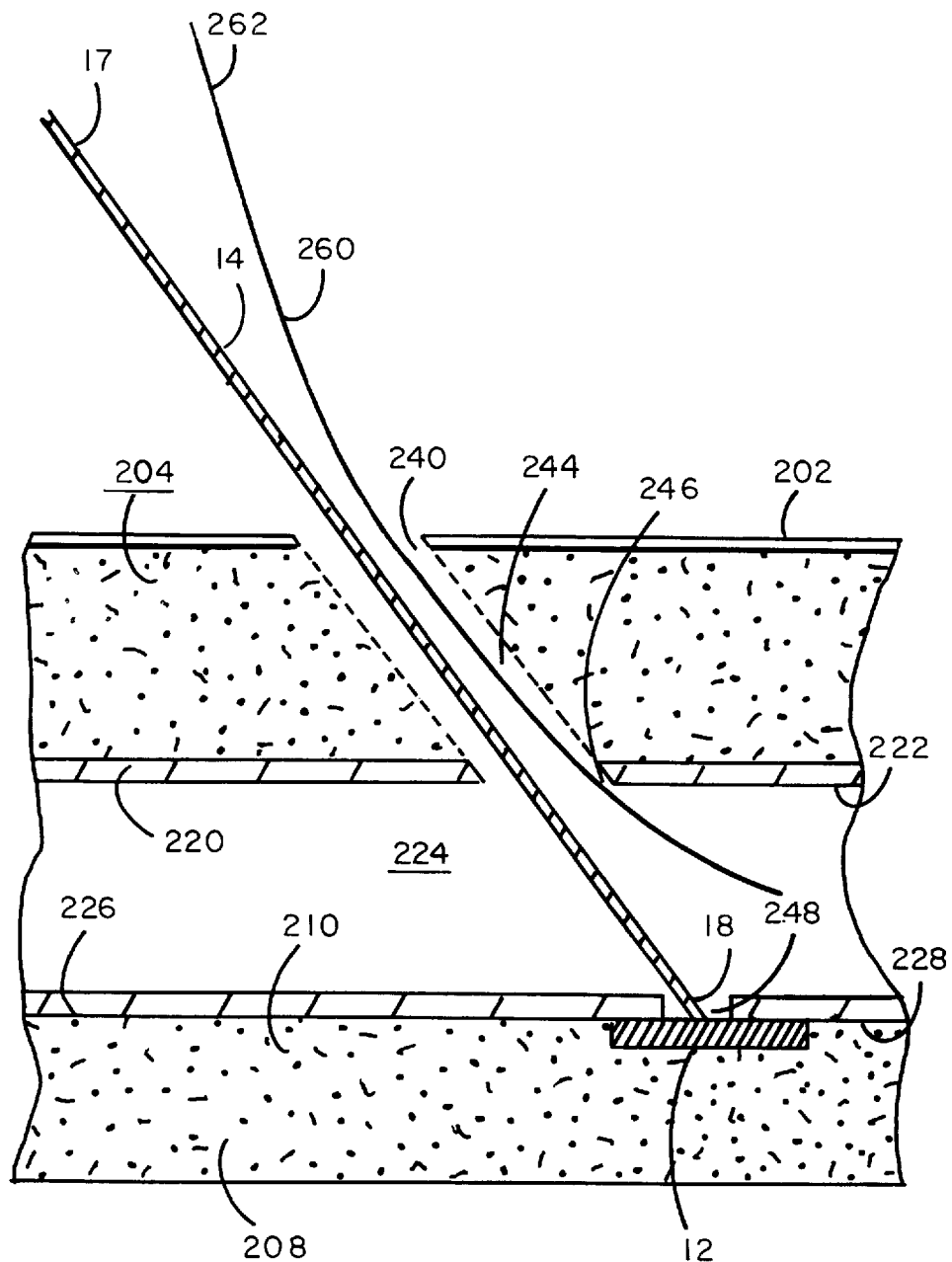

After the buttressing support member 12 has been deployed and aligned against the penetration fracture 248 to buttress and support the posterior vascular wall, the puncture needle 40 may then be completely withdrawn by the physician or surgeon from the puncture site and the body of the living subject. The complete withdrawal and removal of the puncture needle 40 after the aligned deployment of the closure guiding stabilizer 10 at the external surface of the posterior vascular wall and the extension of the steering cable 14 into the external ambient environment while remaining rotably attached to the buttressing support member 12 is illustrated by FIG. 17.

It is important to recognize and appreciate the outcome and consequence of this series of interim manipulative steps—as shown by FIGS. 13–17 collectively. A correct and successful percutaneous puncture has been achieved in which there is a discrete puncture site 240; an aperture void space 244 in the superficial tissue layer 204; a perforation 246 in the anterior vascular wall 220 of the chosen blood vessel; an access to the central blood flow channel 224; and a penetration fracture 248 in the posterior vascular wall 226 of the chosen blood vessel. In addition, a closure guiding stabilizer 10 has been inserted using an adaptation of the modified Seldinger technique such that a buttressing support member 12 has been deployed in aligned position adjacent the exterior surface 228 of the posterior vascular wall 226; and the buttressing support member 12 is disposed within the local tissue 210 and lies adjacent the penetration fracture 248 as a barricade and vascular block. In addition, the deployed closure guiding stabilizer 10 serves to support the posterior vascular wall 226 and acts as a vascular closure of the penetration fracture 248 in the posterior vascular wall. The steering cable 14 rotably attached to the deployed buttressing support member 12 is extended and passed through the penetration fracture 248 of the posterior vascular wall 226, migrates across the central blood flow channel 224 of the blood vessel, and passes out through the vascular perforation 246 in the anterior vascular wall 220 through the aperture void space 244 and out through the puncture site 240 into the external ambient environment outside the body of the living subject. Moreover, while the aligned and deployed closure guiding stabilizer 10 is in proper position, a guidewire 260 extends from the central blood flow channel 224, through the perforation 246 in the anterior vascular wall 220, through the aperture void space 244 in the superficial tissue layer 204, and out through the puncture site 240 into the external ambient environment.

These interim manipulative steps (as illustrated in successful outcome by FIG. 17) thus demonstrate and reveal that a percutaneous puncture obtained by modified Seldinger technique provides the means for aligned closing and stabilized sealing of the vascular perforation and puncture site in position before beginning the catheterization procedure for the patient. Using the guidewire passing into the central blood flow channel of the femoral artery, a diagnostic or interventional catheterization procedure may now b performed and successfully completed. Upon completion of the catheterization procedure to the reasonable satisfaction of the attending physician or surgeon, the means for positioning a closure into a controlled position for an aligned closing and stabilized sealing of the vascular perforation are already in place and available for use on-demand.

Figure 18:
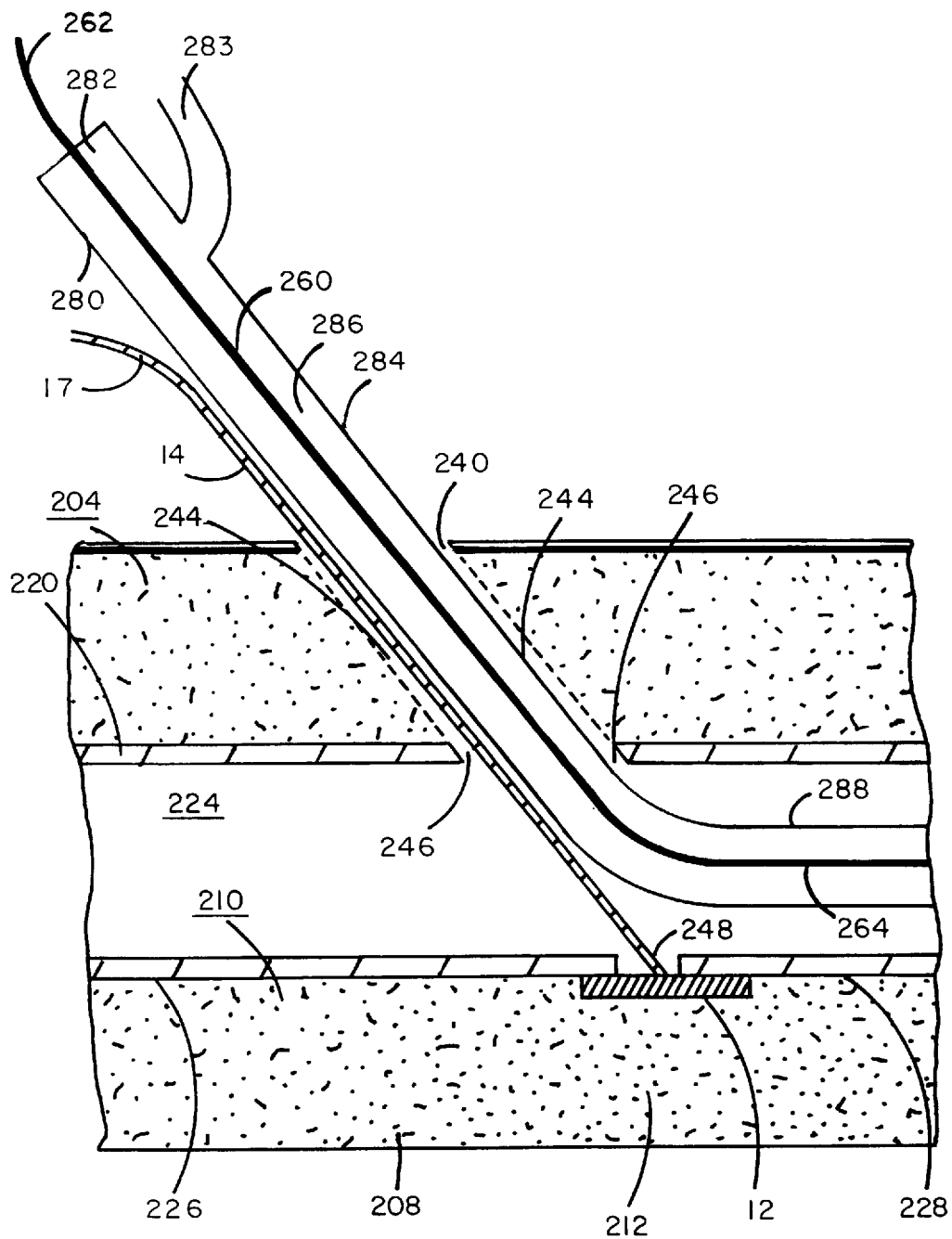

Thus, for catheterization purposes, an introducer sheath 286 typically is advanced over the guidewire 260 into the femoral artery. After placement of the sheath, the inner guidewire is removed. Then, via the sheath, an angiographic catheter is introduced into the artery for catheterization procedures. Upon completion of these procedures, the guidewire is reintroduced through the catheter. This is shown by FIG. 18. The catheter is then physically removed over the guidewire to recreate subsequently the previous conditions illustrated by FIG. 17.

It is important to note that throughout the entire catheterization initiation process and the catheterization procedures themselves, the proximal end 17 of the steering cable 14 remains extended in the external ambient environment while the distal end 18 lies rotably attached to the buttressing support member (then deployed in an aligned placement at the external surface of the posterior vascular wall and abutting the penetration fracture in the posterior vascular wall). The presence and existence of the extended steering cable does not hinder or meaningfully interfere with any part or process of the catheterization procedure or the successful completion of the catheterization procedure as intended for the patient.

Controlled positioning and placement of the closure

The closure of choice in this first preferred method is that solid plug illustrated by FIG. 7 and described in detail previously herein. The solid cylinderically-shaped plug 80 has passageways 82, 84 in parallel through the thickness and axial length of the plug. These are intended for receiving and juncture with the extended, proximal end of the steering cable found in the external ambient environment. In this first preferred method of closure, it is also desirable to employ the guidewire 260 also extended from the central blood flow channel into the external ambient environment. The process of controlled positioning for the solid plug closure is illustrated by FIGS. 19–23 respectively.

Figure 19:
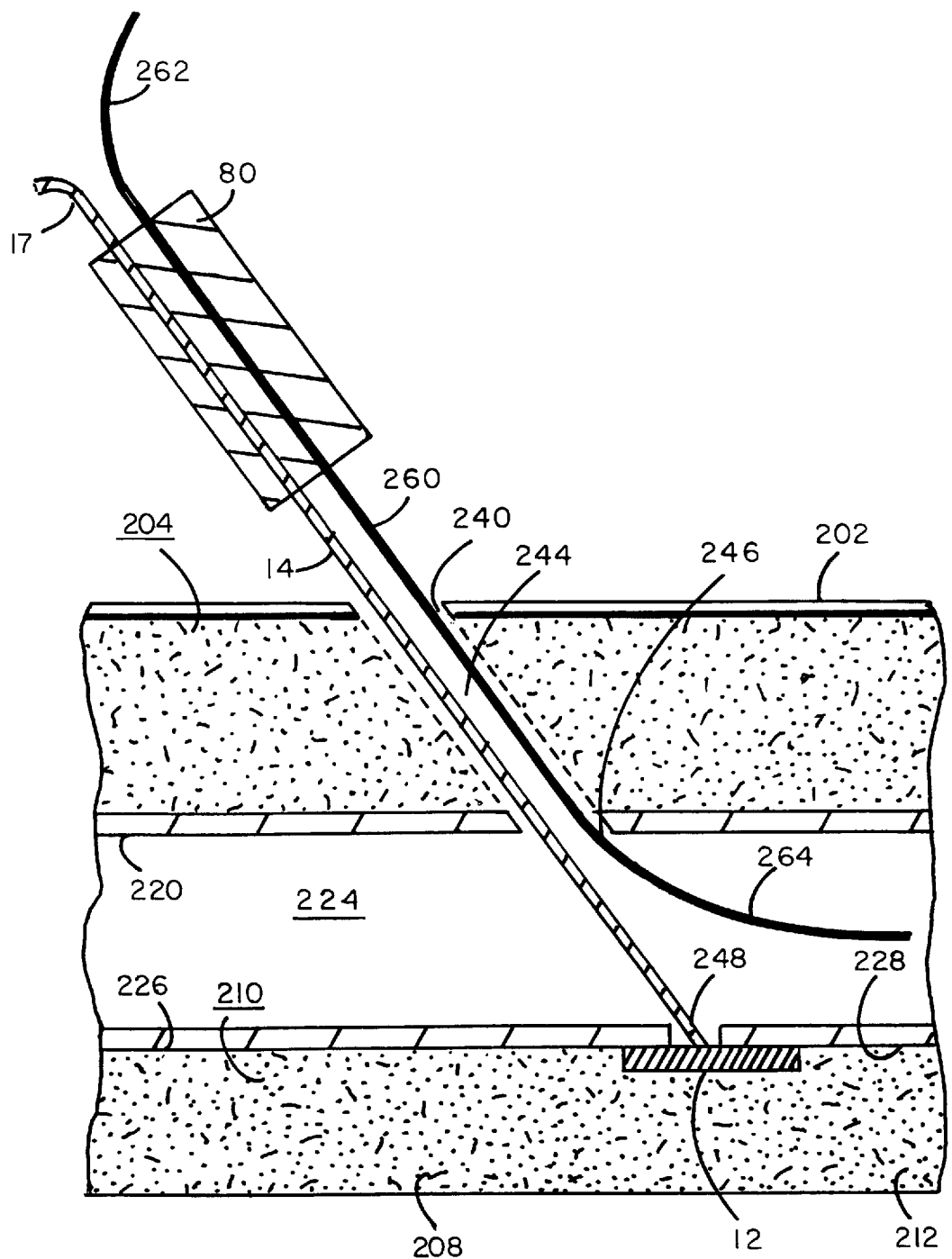

As shown by FIG. 19, the solid cylindrically-shaped plug 80 has received the proximal end 17 of the extended steering cable 14 through the passageway 84. Concurrently, the proximal end of the guidewire 260 is desirably received and passed through the passageway 82. In this manner, the guidewire serves as supplemental interim routing means for physical insertion of the solid plug closure 80; and the extended steering cable 14 (after being received and passed through the axial thickness of the solid plug closure 80) acts as a tension cable and guiding means for controlled positioning into the puncture site 240 and the aperture void space 244 as well as for placement adjacent the perforation 246 in the anterior vascular wall 220 of the femoral artery.

Figure 20:
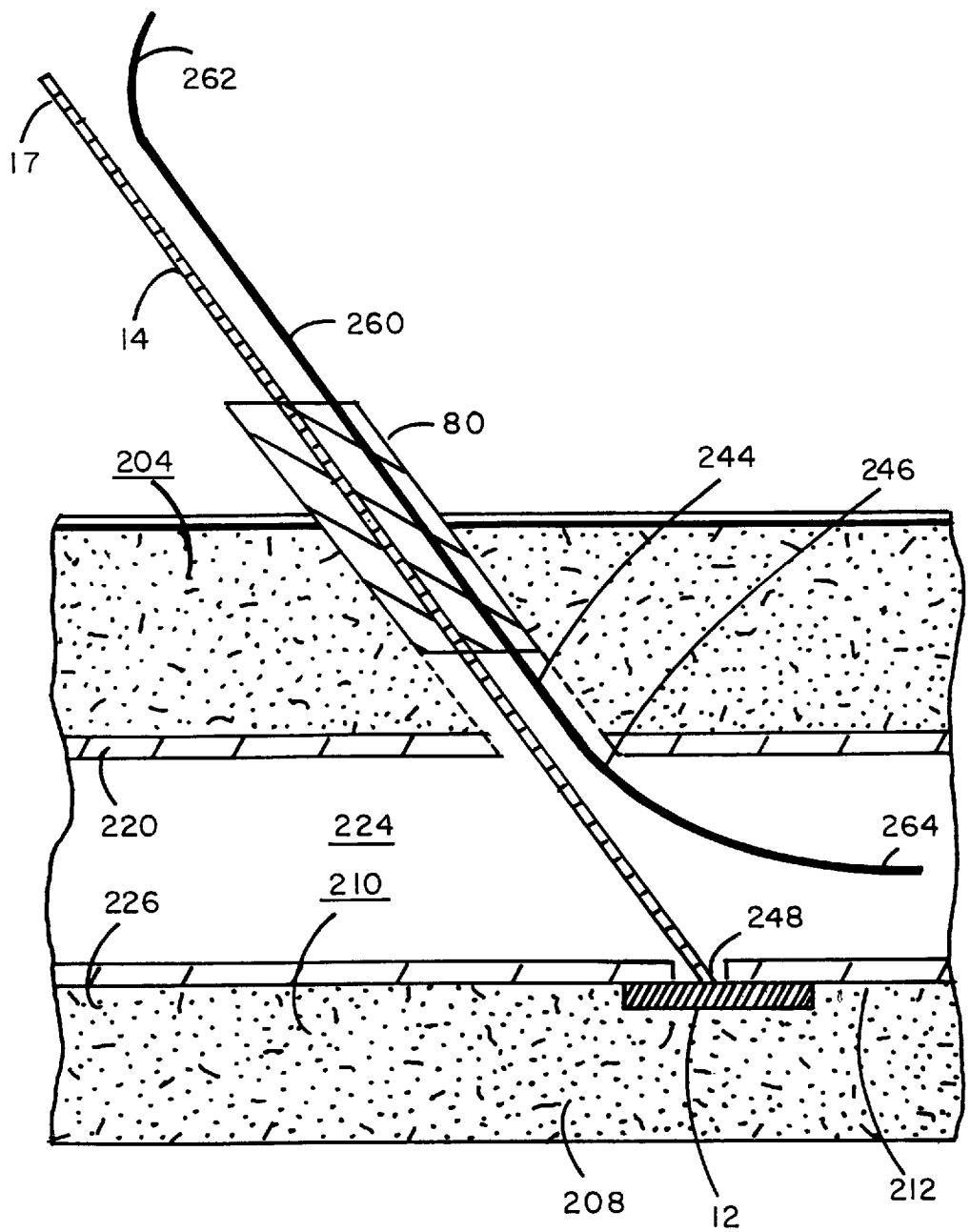
Figure 21:
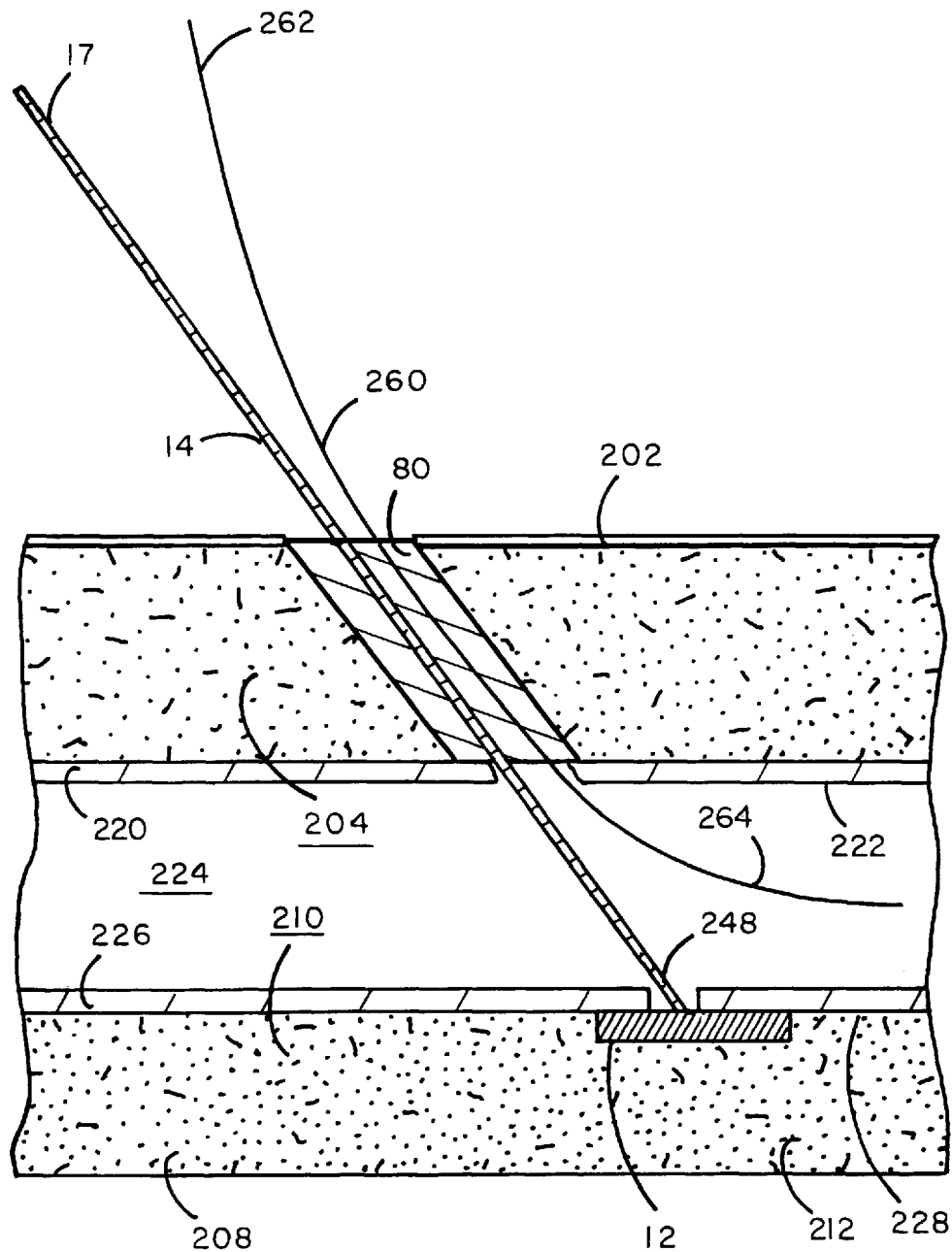

Rceipt of and initiation of closure using the steering cable 14 as a directional leader and guide is shown by FIGS. 19, 20, and 21 respectively. It will be appreciated that the preferred location of the closure plug 80 is adjacent to and abutting the vascular perforation 246 in the anterior vascular wall 220. This preferred location places the closure plug 80 at the anterior vascular wall adjacent to the vascular perforation 246 for controlled and effective closing of the perforation to achieve hemostasis. The body and bulk of the cylindrically-shaped solid plug 80, when placed in the controlled position, also concurrently fills the aperture void space 244 existing within the superficial tissue layer 204, and can optionally also fill the puncture site 240 at the surface of the skin. In this manner, an aligned closing and filling of not only the vascular perforation but also of the aperture void space in the superficial tissues under the skin is achieved in a controlled and reliable manner—via the extended steering cable 14 and the deployed buttressing support member 12 then disposed in aligned placement against the exterior surface of the posterior vascular wall. The tension force and directional guidance for the solid plug closure 80 is provided by the extended steering cable continuously and reliably during the entire insertion of the plug into the puncture site.

Figure 22:
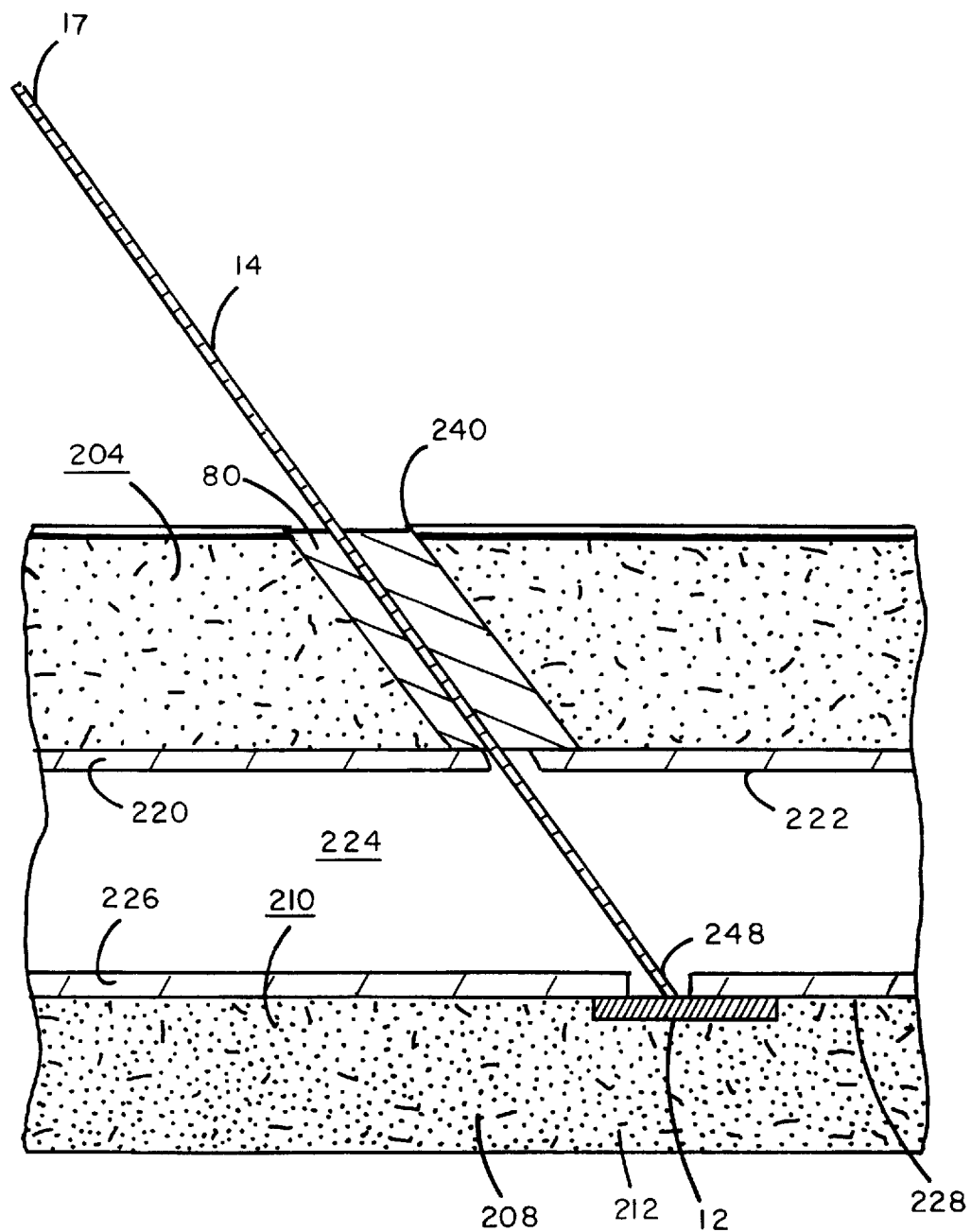
Figure 23:
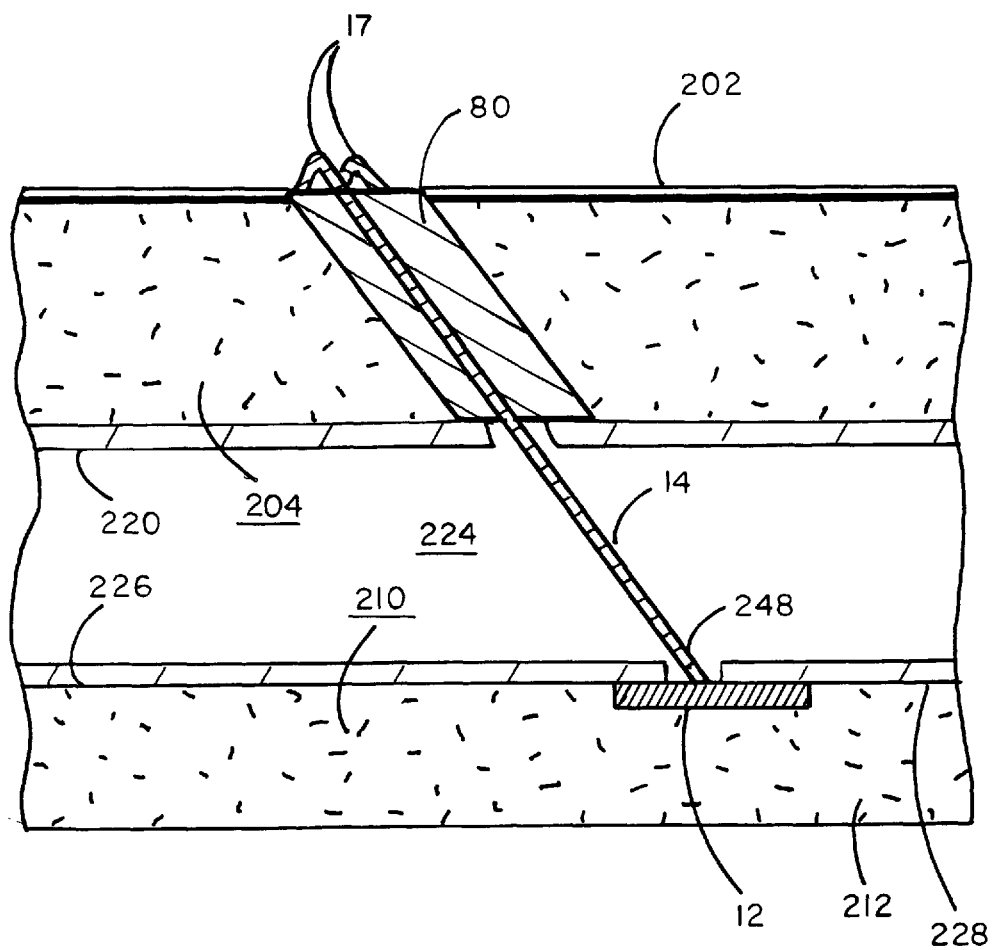

Subsequent to controlled placement of the solid plug closure 80 within the aperture void space 244 and at or adjacent to the vascular perforation 246 in the anterior vascular wall 220, the guidewire 260 is withdrawn and removed completely. This outcome is illustrated by FIG. 22, in which the plug closure 80 remains in controlled position via the received steering cable 14 extending from the deployed buttressing support member 12. Finally, the proximal end 17 of the steering cable 14 in the external ambient environment is then permanently joined to the positioned solid plug closure 80 and/or to the surrounding skin. In the preferred embodiment, the steering cable 14 is composed of resorbable suture material; and thus the steering cable in this preferred embodiment may be sutured directly to both the positioned plug and the surrounding skin in order to effect a stabilized sealing of the percutaneous puncture and puncture site.

It will be appreciated that, unlike hemostasis devices conventionally known in this art, the present apparatus and method of use for closure is simple and does not require exchange with any other components, introducers or articles at the end of the catheterization procedure in order to close and seal the puncture site effectively and completely. The methodology does not compromise the lumen of the artery or vein since the closure guiding stabilizer is deployed in aligned position outside the posterior vascular wall and does not encounter the central blood flow of the artery or vein. Equally important, because the solid cylindrical-shaped plug closure is advanced using the extended steering cable attached to the closure guiding stabilizer then deployed outside the blood vessel itself, the positioning of the solid plug closure is controlled; it provides for an aligned closing of the puncture site, the aperture void space, and the vascular perforation; it prevents any accidental delivery of the solid plug closure into the central blood flow channel of the artery or vein; and it avoids any sliding or slippage of the solid plug closure laterally or transversely as an consequence of being guided over the extended steering cable. In this manner, the solid plug closure is utilized and inserted into the puncture site and aperture void space in a controlled manner for an aligned closing and stabilized sealing of the vascular perforation.

Figure 24:
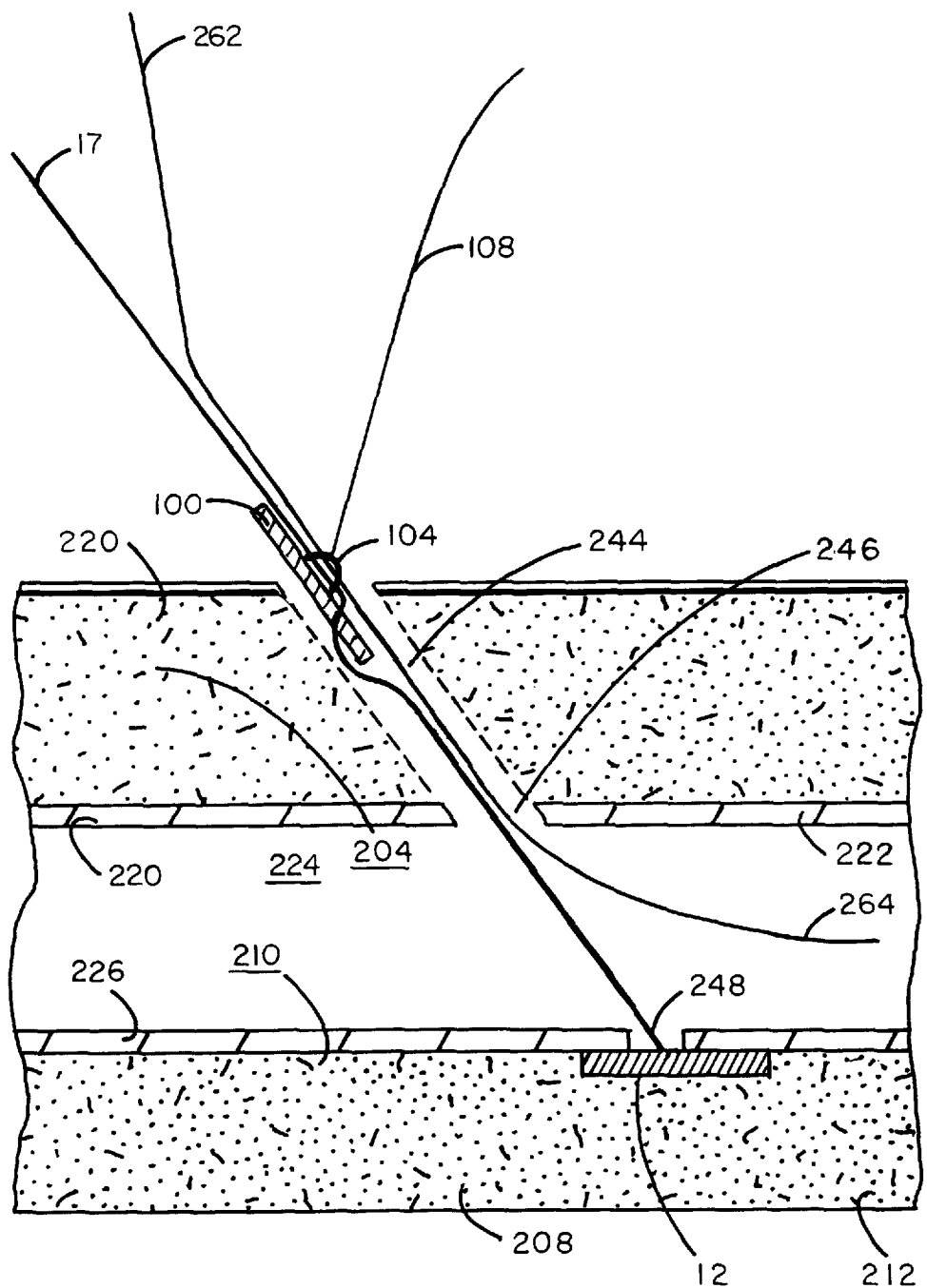
Figure 25:
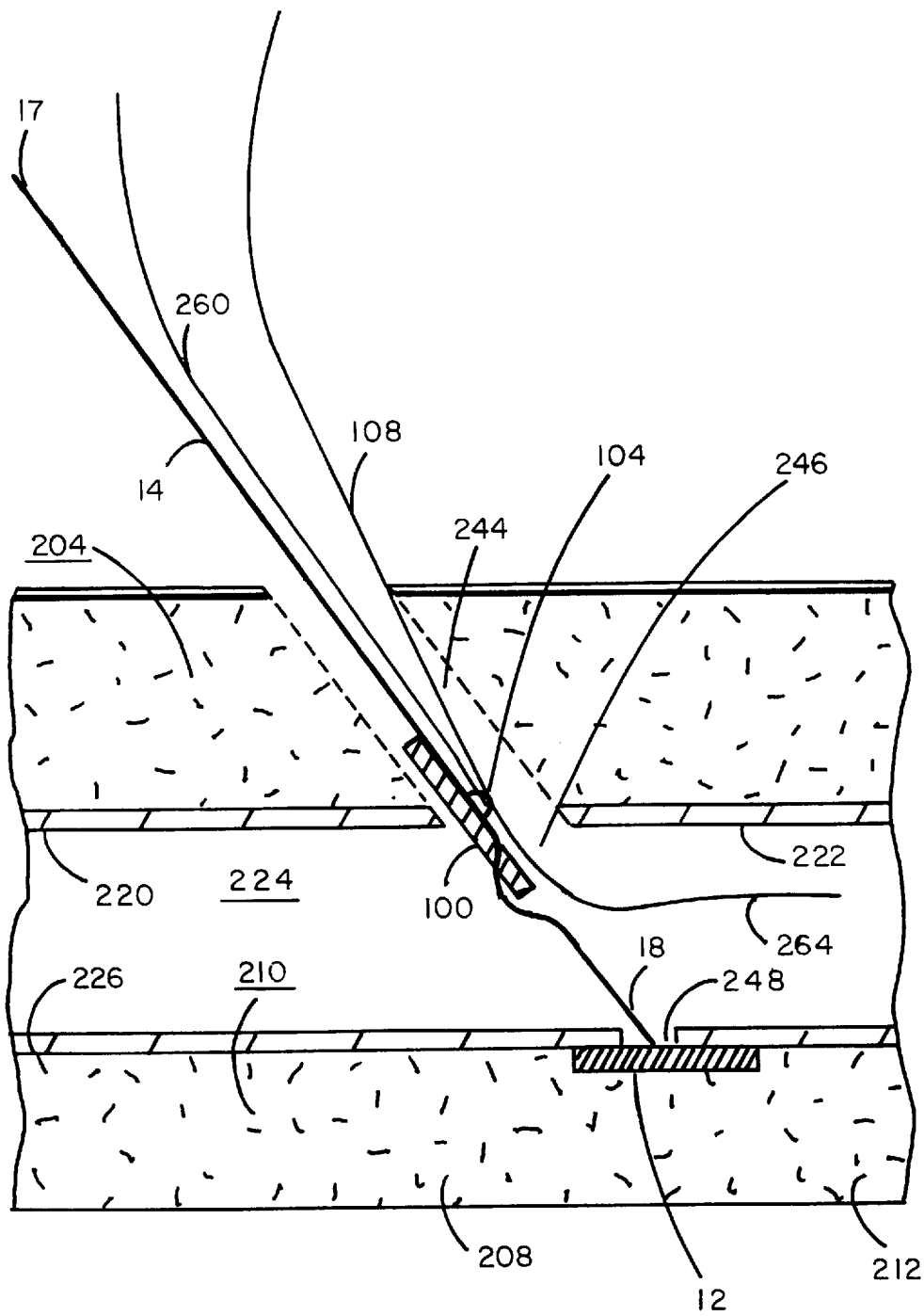
Figure 26:
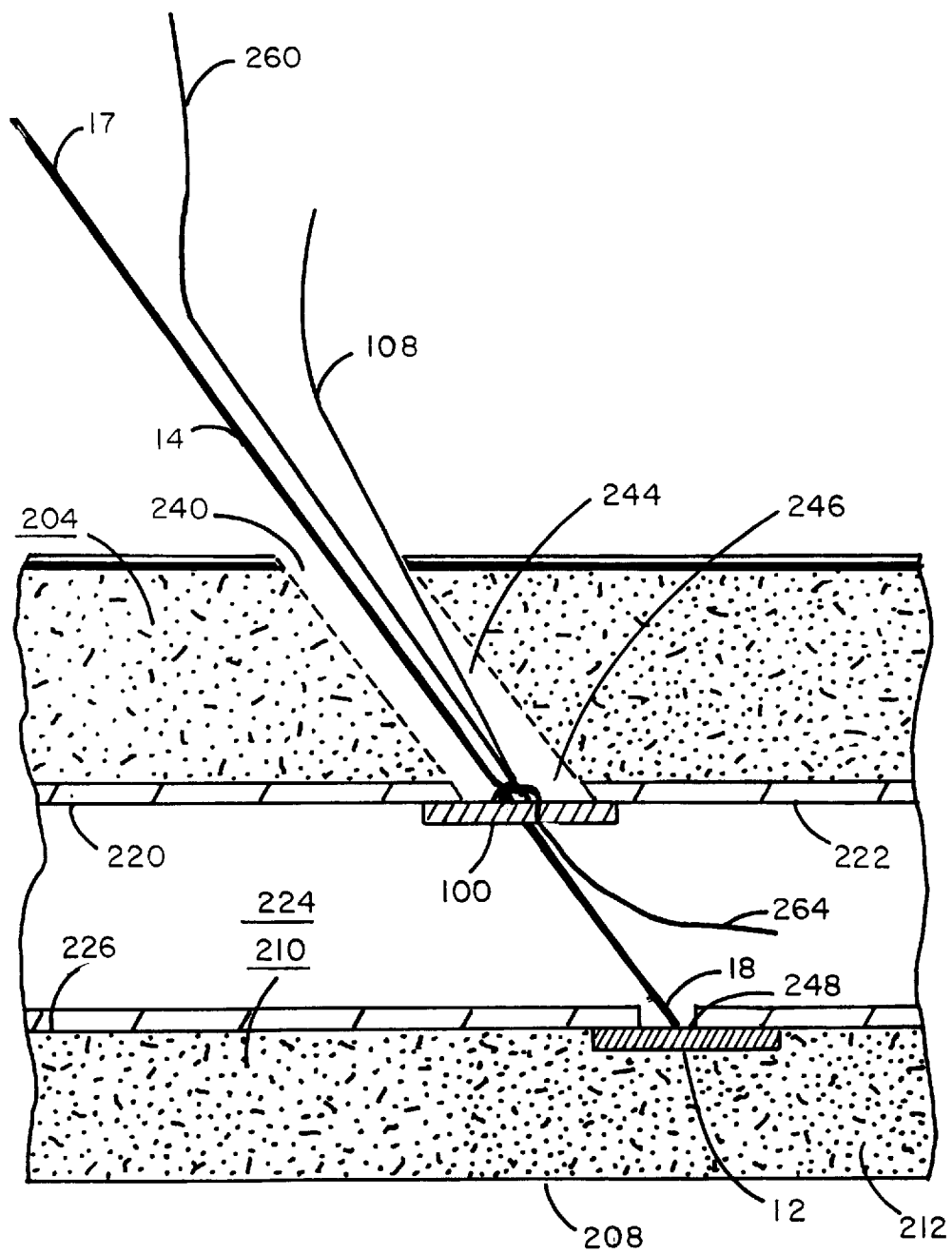

A second series of interim manipulative steps using an alternative type of closure means An alternative manner of controlled closure and effective sealing is achieved using the closure illustrated by FIGS. 9A and 9B respectively and which has been described in detail previously herein. This type of solid closure is the membrane/plate anchor, a generally rectangularly-shaped anchor having an attachment collar and an anchoring line. The manner of using this type of anchor closure is illustrated by FIGS. 24–28 respectively. As seen in FIG. 24, the anchor closure 100 has been threaded via the thru hole 103 and the attachment collar 104 onto the length of the extended steering cable 14; and also has engaged the guidewire 260 for additional control and stabilization during the process of transfer from the external ambient environment into the puncture site for closure of the vascular perforation in the anterior vascular wall. The anchor line 108 is extended from the attachment collar 104 throughout the migration process and remains in the hands of the attending physician or surgeon for additional control of the anchor 100 throughout the entire placement process. The migration of the anchor 100 proceeds through the puncture site 240, into the aperture void space 244 and to the vascular perforation 246 at the anterior vascular wall 220. This is illustrated by FIG. 25.

Subsequently, the anchor 100 is placed into the central blood flow channel 224 of the chosen blood vessel, the femoral artery. As seen via FIG. 26 the top surface 106 of the anchor 100 has been placed against the internal surface 222 of the anterior vascular wall 220 in a manner which blocks and covers the vascular perforation 246 completely from within the blood channel. It will be noted that the anchoring line extends from the attachment collar 104, through the aperture void space 244; and passes out the puncture site 240 into the external ambient environment. The tension force applied by the physician or surgeon holding the anchor line 108 maintains the anchor plate in the desired location within the blood channel against the vascular perforation 246. However, the controlled positioning for the anchor closure 100 is provided by the extended steering cable 14, which is held by the physician at one end and remains rotably attached to the deployed and aligned buttressing support member 12 (previously positioned against the external surface 228 of the posterior vascular wall 226 and which acts to block and support the penetration fracture 248 in the posterior vascular wall). The guidewire 260 serves as an axillary and optional means by which additional control is desirably exerted on the anchor 100 as it is introduced into the percutaneous puncture and becomes positioned within the central blood flow channel against the vascular perforation in the anterior vascular wall.

Figure 27:
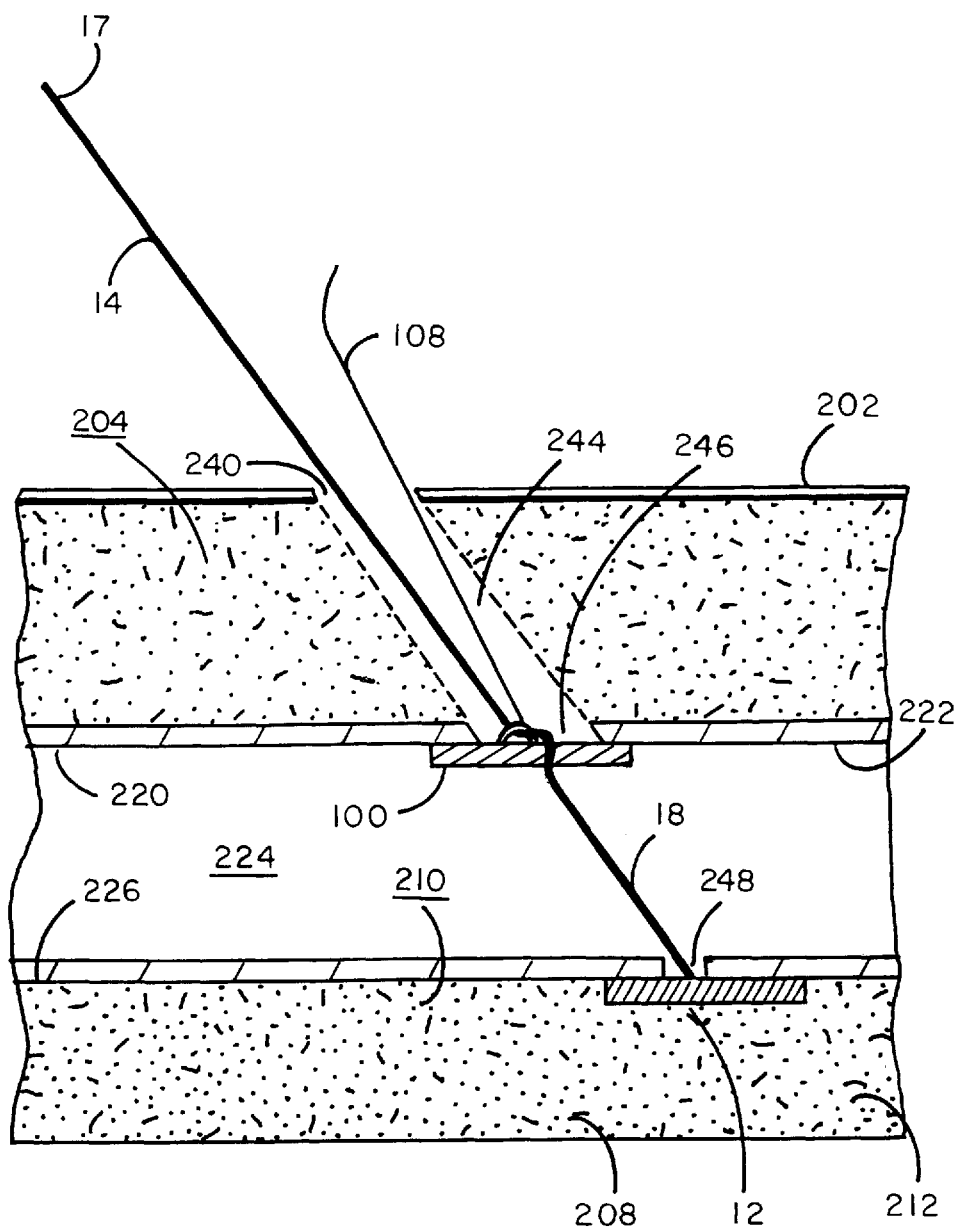
Figure 28:
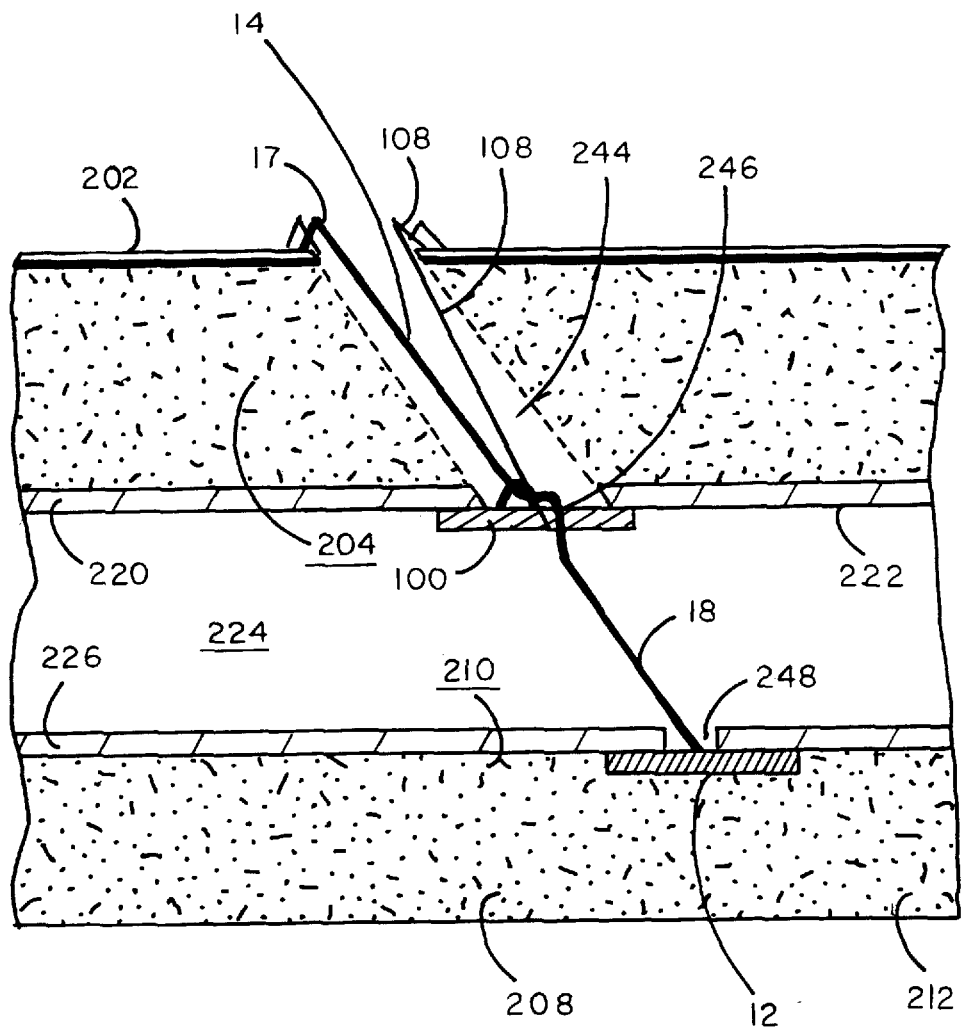

The securing of the properly positioned anchor closure 100 is shown by FIGS. 27 and 28 respectively. As seen in FIG. 27, the guidewire 260 has been withdrawn and removed completely. This allows the attending physician or surgeon to maintain stability and control via the extending steering cable 14 and to maintain the blockage of the vascular perforation 246 by retaining control of the anchoring line 108 within the ambient environment. Accordingly, the attending physician and surgeon may then utilize the distal end of the steering cable 14 and the distal end of the anchoring line 108 as they extend within the ambient environment for suturing directly to the skin in the manner illustrated by FIG. 28. This alternative type of closure means, the anchor closure thus provides for a controlled aligned closing and stabilized sealing on-demand of the vascular perforation in the anterior vascular wall after percutaneous puncture.

In some patient instances, it may be advantageous and highly desirable to utilize and combine two different types of closures together in order to achieve hemostasis and avoid major complications after performance of a catheterization procedure. In such instances both the solid cylindrically-shaped plug closure 80 (described as the first preferred closure means herein) and the anchor type of closure (described here as an alternative closure means) may be employed in unison and inserted into the puncture site concurrently. In these instances, it is recommended that the controlled positioning of the anchor closure via the steering cable be performed first, followed by insertion of the solid cylindrical-shaped plug closure using the same steering cable. It will be recognized that the proper positioning of the anchor closure merely blocks the vascular perforation in the anterior vascular wall from inside of the blood vessel; and that the vascular blockage is limited to the area of the vascular perforation at the internal surface of the blood vessel. The subsequent introduction of the solid cylindrically-shaped plug closure via the steering cable will then place a solid plug mass into a controlled filling position within the aperture void space of the superficial tissue layer. Via this combination use of two different types of closures, each of which is carefully guided into a controlled position via the steering cable of the previously deployed closure guiding stabilizer, both a blockage of the vascular perforation and a solid mass filling of the aperture void volume can be achieved concurrently. This type of combined procedure allows the empty volume caused by percutaneous puncture to be completely filled by solid closure material; and this combination of two closure means in a single system of closure is expected to provide enhance reliability and effectiveness to prevent bleeding while achieving an aligned closing and stabilized sealing in a permanent fashion.

II. A Second Preferred Aperture Embodiment And Method Of Closure

The second preferred apparatus embodiment employs the closure guiding stabilizer illustrated by FIGS. 3A and 3B and which is described in detail previously herein. This embodiment of the apparatus comprises a closure guiding stabilizer 20 having a buttressing support member 22, and two individual and distinct steering cables 24, 26. This embodiment of the closure guiding stabilizer is employed after percutaneous puncture of a chosen blood vessel as described previously herein and illustrated by FIGS. 10, 11, and 12 respectively. The preliminary manipulative steps are thus identical in this second preferred embodiment of the apparatus and method for closure. The use of the alternate apparatus embodiment for the closure guiding stabilizer and the use of an alternative embodiment of the solid cylindrically-shaped plug closure illustrated by FIG. 8, provide a second preferred method for aligned closing and stabilized sealing of a vascular perforation after percutaneous puncture of a chosen blood vessel.

After percutaneous puncture using the dual-lumen puncture needle and the preliminary manipulative steps shown by FIGS. 10–12 collectively has been achieved, a third series of interim manipulations is performed during which the second preferred embodiment of the closure guiding stabilizer is deployed and placed in aligned position. This third series of interim manipulations is illustrated by FIGS. 29–33 respectively.

Figure 29:
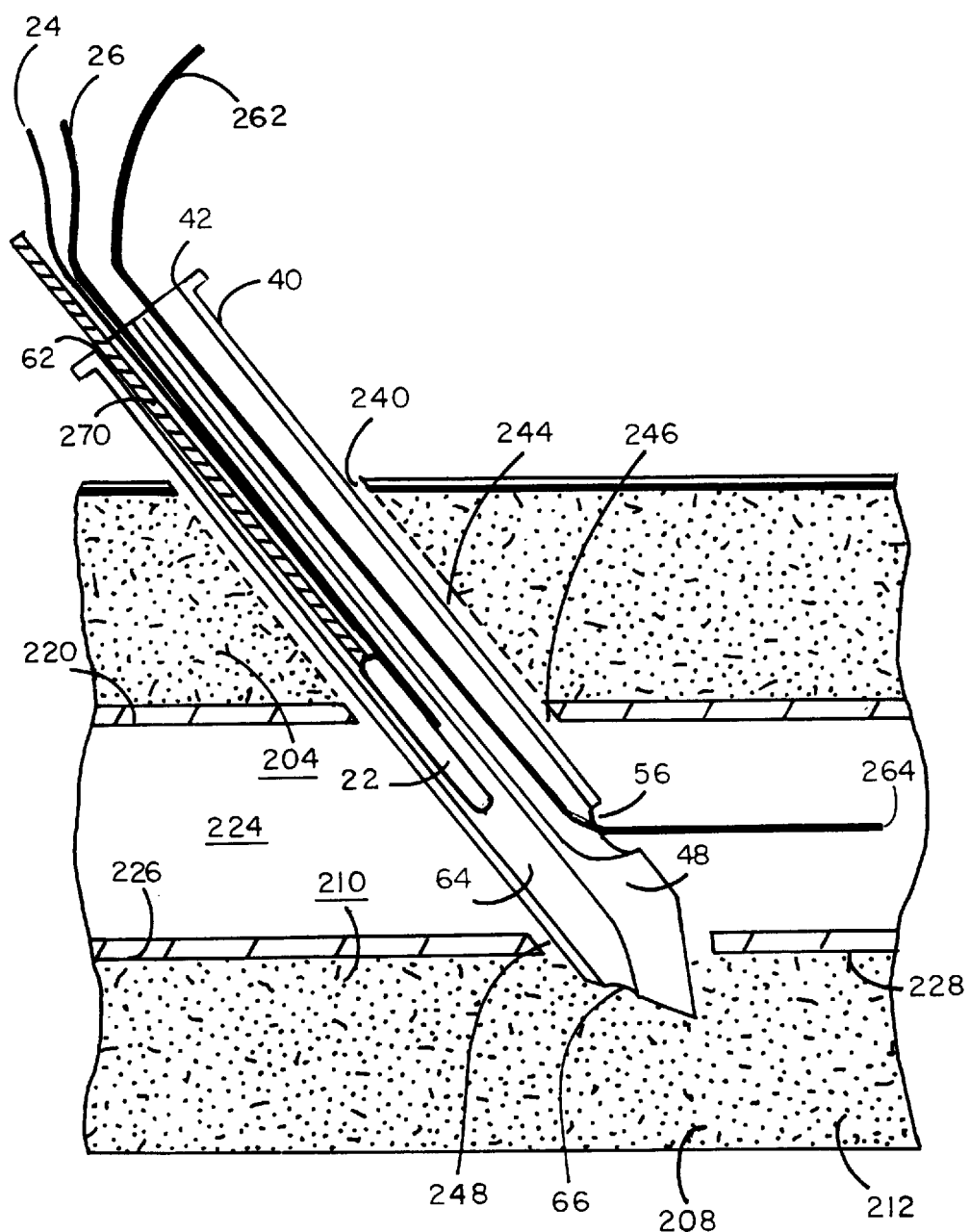

As seen in FIG. 29, the puncturing needle 40 has achieved percutaneous puncture of the blood vessel such that the anterior bore 50 is in fluid communication with the central blood channel 224 of the blood vessel, the femoral artery; and the posterior bore 60 is in communication with the local tissue 210 of the deeper tissue layer 208 adjacent to the penetration fracture 248 the posterior vascular wall 226. A guidewire 260 has been inserted into the anterior opening 52, extended through the internal anterior lumen 54, and passed through the anterior exit hole 56 into the central blood flow channel 224 of the artery. The act of percutaneous puncture at the chosen anatomical site has also created a puncture site 240, an aperture void space 244 in the superficial tissue layer 204, a perforation 246 in the anterior vascular wall 220 of the blood vessel; and a penetration fracture 248 within the posterior vascular wall 226.

Figure 30:
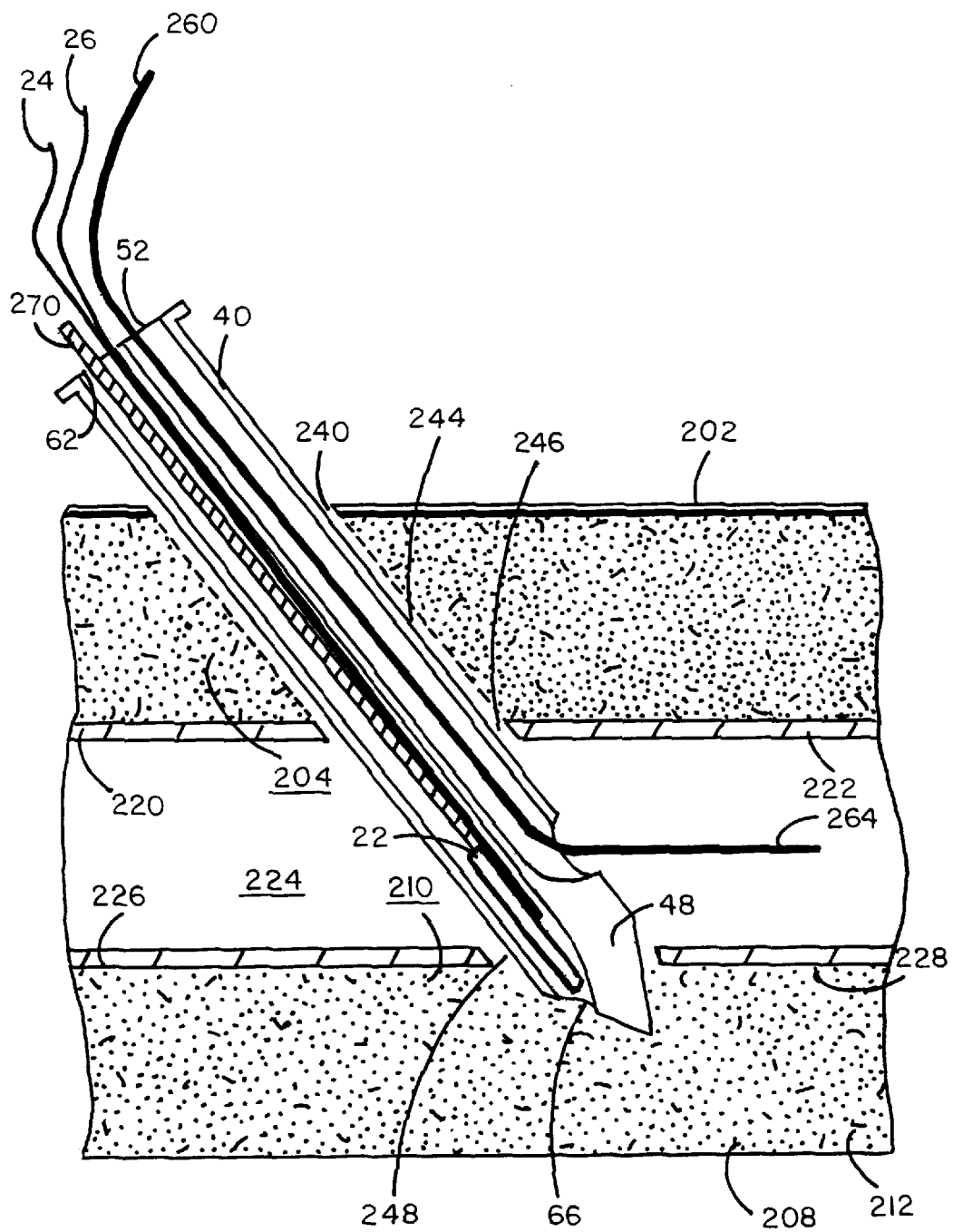

The second preferred apparatus embodiment of the closure guiding stabilizer is introduced by insertion through the posterior opening 62 and introduction into the posterior internal lumen 64 of the posterior bore 60 in the puncture needle 40. This is illustrated by FIG. 29. A pusher rod 270 aids in advancing the closure guiding stabilizer 20 along the axial length of the posterior bore 60 for egress through the posterior exit hole 66. This is illustrated by FIG. 30.

Figure 31:
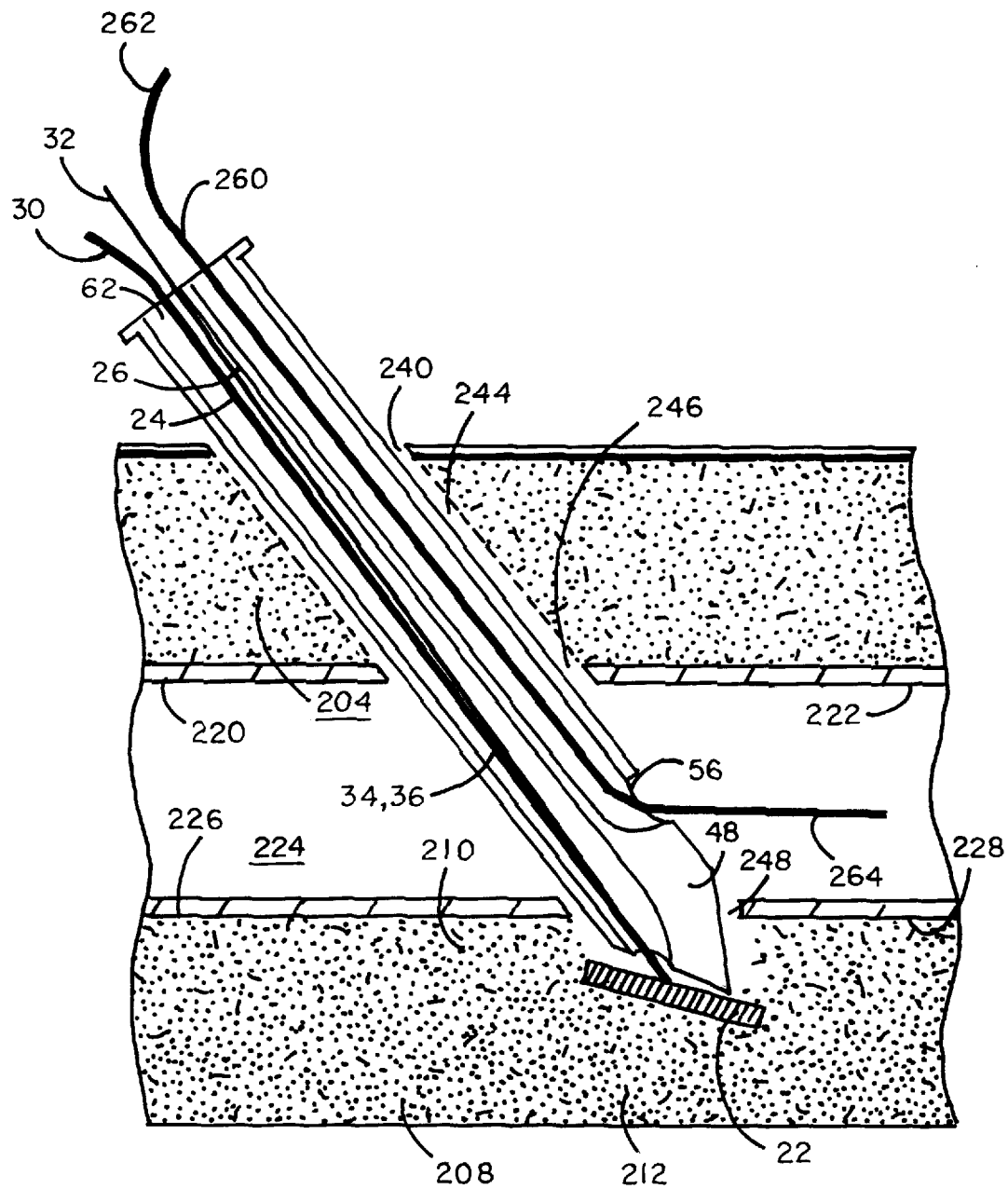

Subsequently, the closure guiding stabilizer 20 is advanced out of the posterior bore 60 into the local tissue 210 of the deeper tissue layer 208 adjacent to the penetration fracture 248 in the posterior vascular wall 226. This event is illustrated by FIG. 31, in which the buttressing support member 22 is advanced into the local tissue 210 while the two steering cables 24, 26 extend rearward through the entirety of the posterior bore 60 into the external ambient environment. In this manner, the proximal ends 30, 32 of the two steering cables 24, 26 may be grasped, held and controlled by the attending physician and surgeon while the distal ends 34, 36 of the steering cables remain rotably attached to the buttressing support member 22.

Figure 32:
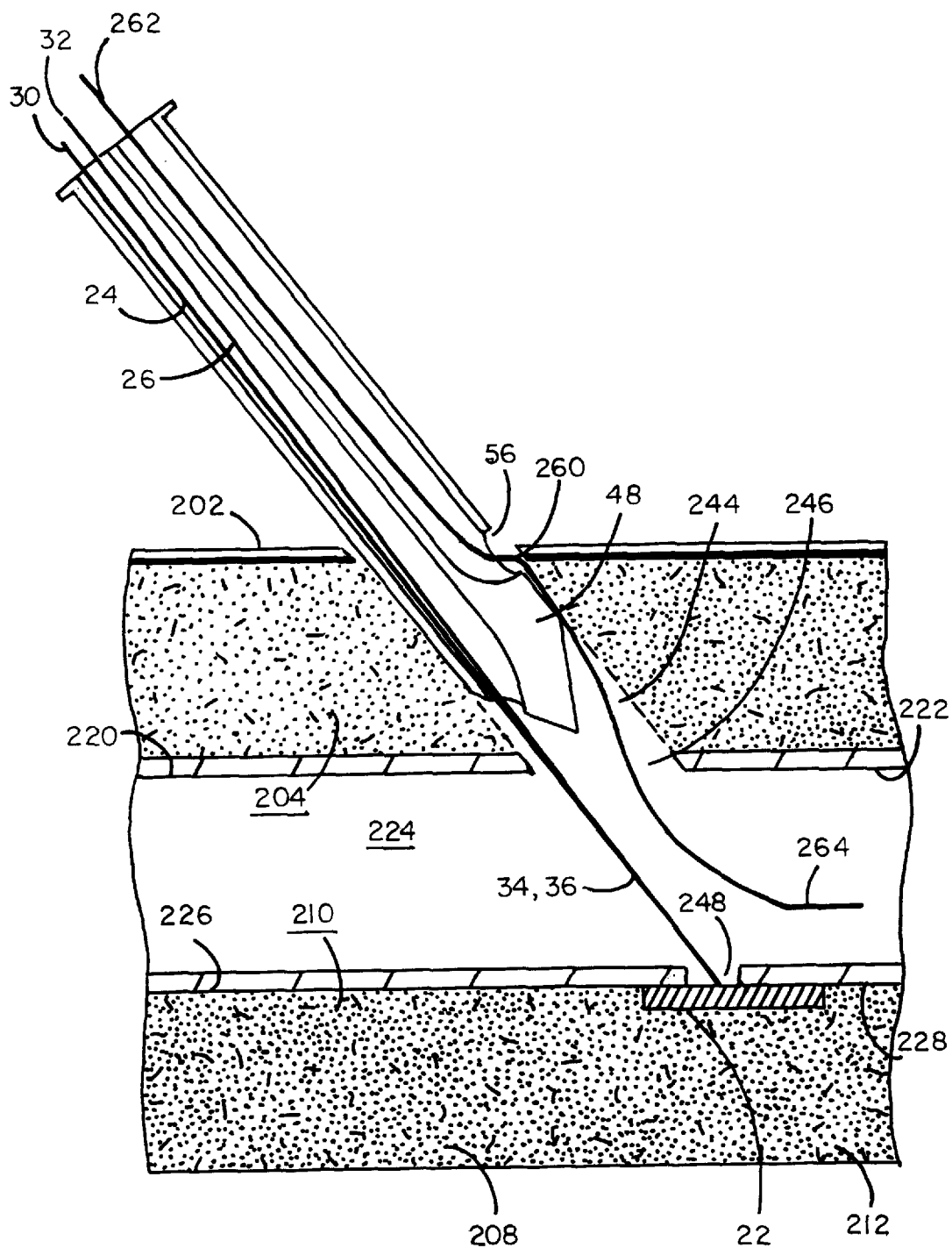

It is desirable that the inserted puncture needle 40 then be partially withdrawn by the attending physician or surgeon such that the distal tip 48 of the puncture needle 40 is removed from direct or intimate contact with the blood vessel itself. This act of partial withdrawal of the puncture needle 40 is shown by FIG. 32. Simultaneously or concurrently with the partial withdrawal of the puncture needle 40, the attending physician or surgeon will pull on the two steering cables 24, 26; and apply a tension force upon the deployed buttressing support member 22 then lying adjacent to the penetration fracture 248 in the posterior vascular wall 226. The act of applying tension force will concomitantly pull the buttressing support member 22 into aligned position against the exterior surface 228 of the posterior vascular wall 226; and by this aligned placement cause the deployed buttressing support member 22 to act as a barrier and vascular stopper for the penetration fracture 248. In addition, the aligned placement of the deployed buttressing support member 22 of the closure guiding stabilizer 20 will provide support for the posterior vascular wall 226 and stability for the tissues surrounding the penetration fracture 248.

Figure 33:
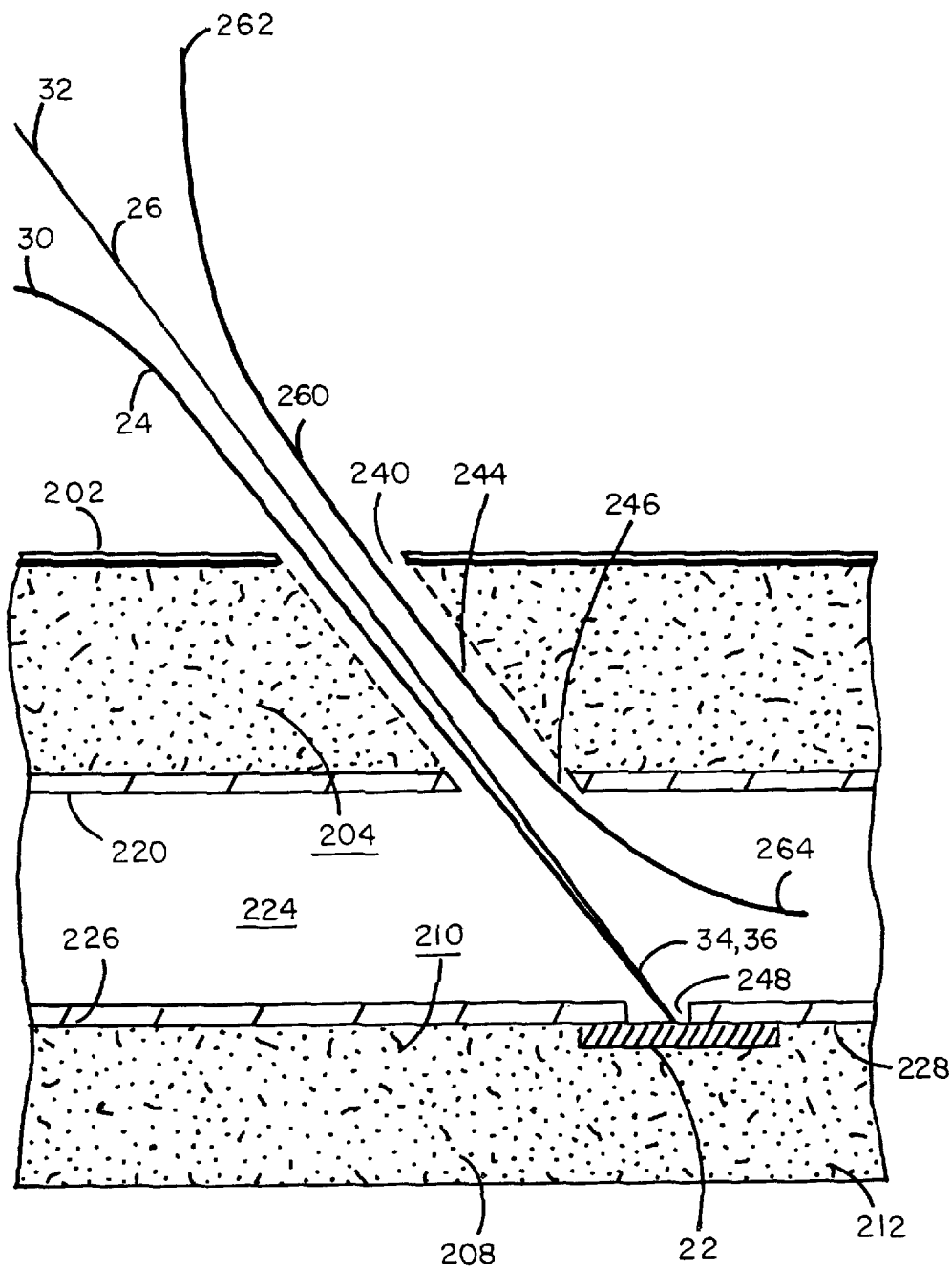

After the deployed closure guiding stabilizer 20 has been placed in aligned position against the penetration fracture 248 of the posterior vascular wall 226, the puncture needle may then be removed and withdrawn completely by the attending physician or surgeon. This act and consequence is shown by FIG. 33. The result of withdrawing the puncture needle completely results in the deployed closure guiding stabilizer 20 being in aligned position on the external surface of the posterior vascular wall and functioning as a vascular stopper closing and sealing the penetration fracture in the posterior vascular wall. In addition, the two steering cables 24, 26 remain rotably attached to the buttressing support member 22; and are seen to extend and pass through the posterior vascular wall 226 via the penetration fracture 248, across the central blood flow channel 224 of the blood vessel, through the vascular perforation 246 in the anterior vascular wall 220, and out through the aperture void space 244 and the puncture site 240 into the external ambient environment. Similarly, the guidewire 260 remains in place such that its distal end lies within the central blood channel 224 while its proximal end is in the external ambient environment.

The means for aligned closing and stabilized sealing of the vascular perforation and the blood vessel is now in proper place; is available for on-demand usage; and will remain in deployed and aligned position to aid as a guide in inserting the chosen closure into a controlled position for an aligned closing and stabilized sealing of the vascular perforation.

Figure 34:
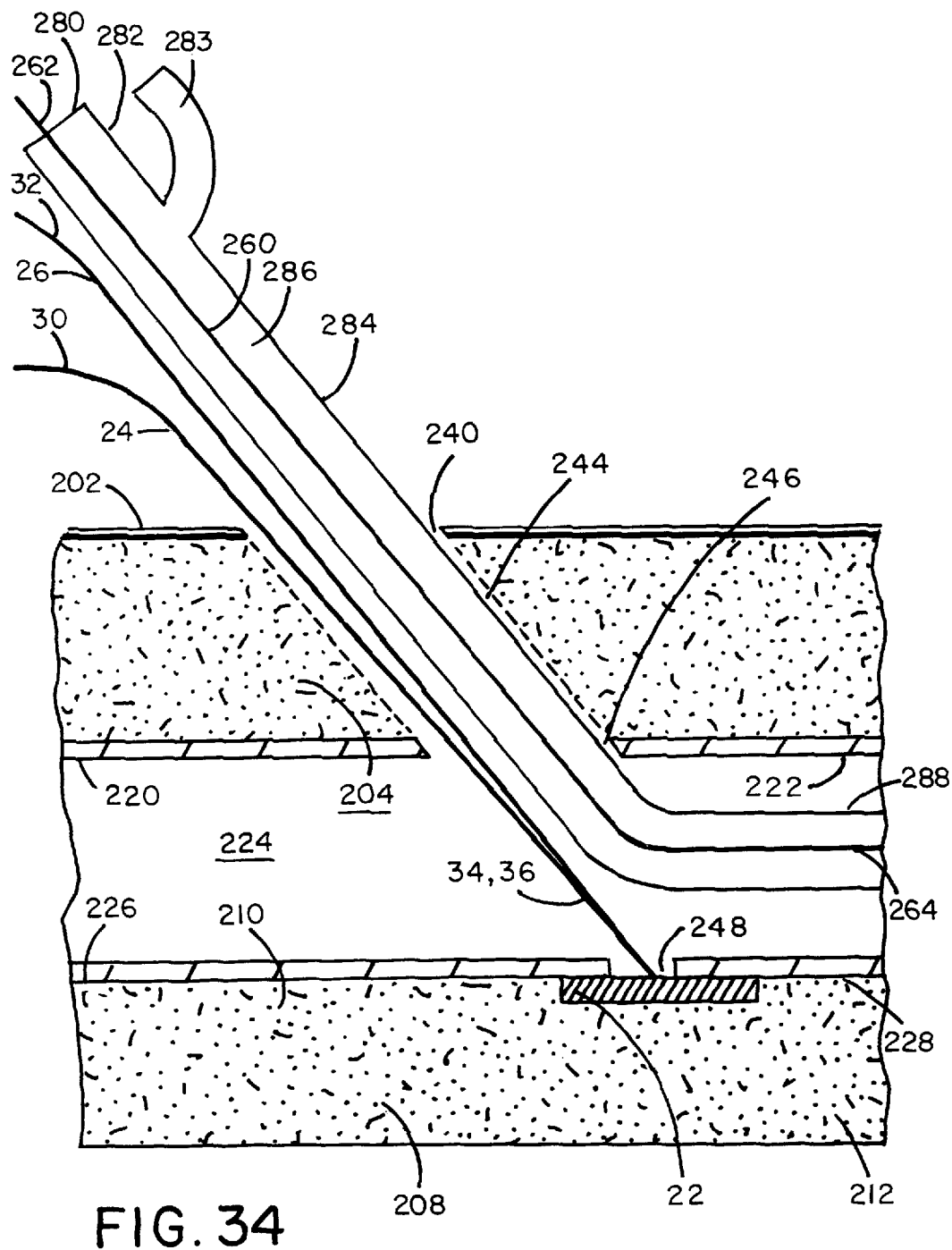

The attending physician or surgeon then proceeds to introduce a sheath and catheter through the percutaneous puncture in order to perform the desired diagnostic or interventional procedure for the patient. This is illustrated by FIG. 34 which shows the catheter 284 introduced into the central blood flow channel 244 of the femoral artery via the vascular perforation 246 in the anterior vascular wall 220. It will be recognized and appreciated also that during the entirety of the catheterization procedure, the two steering cables 24, 26 remain extended from the buttressing support member 22 through the percutaneous puncture into the ambient environment. The presence of the two steering cables 24, 26 does not obstruct, hinder, or meaningfully interfere with the intended catheterization procedure at any time.

The closure sequence of manipulative steps

The act of aligned closing and stabilized sealing for the vascular perforation after completion of the catheterization procedure is shown by FIGS. 35–39 respectively. In this second preferred system and method of closure, it is desirably to employ an introducer sheath 290 over the guidewire 260 into the femoral artery. Such an introducer sheath is conventionally known and used as part of the modified Seldinger technique; and is routinely employed as an aid in the insertion and subsequent withdrawal of a catheter into the chosen blood vessel.

Figure 35:
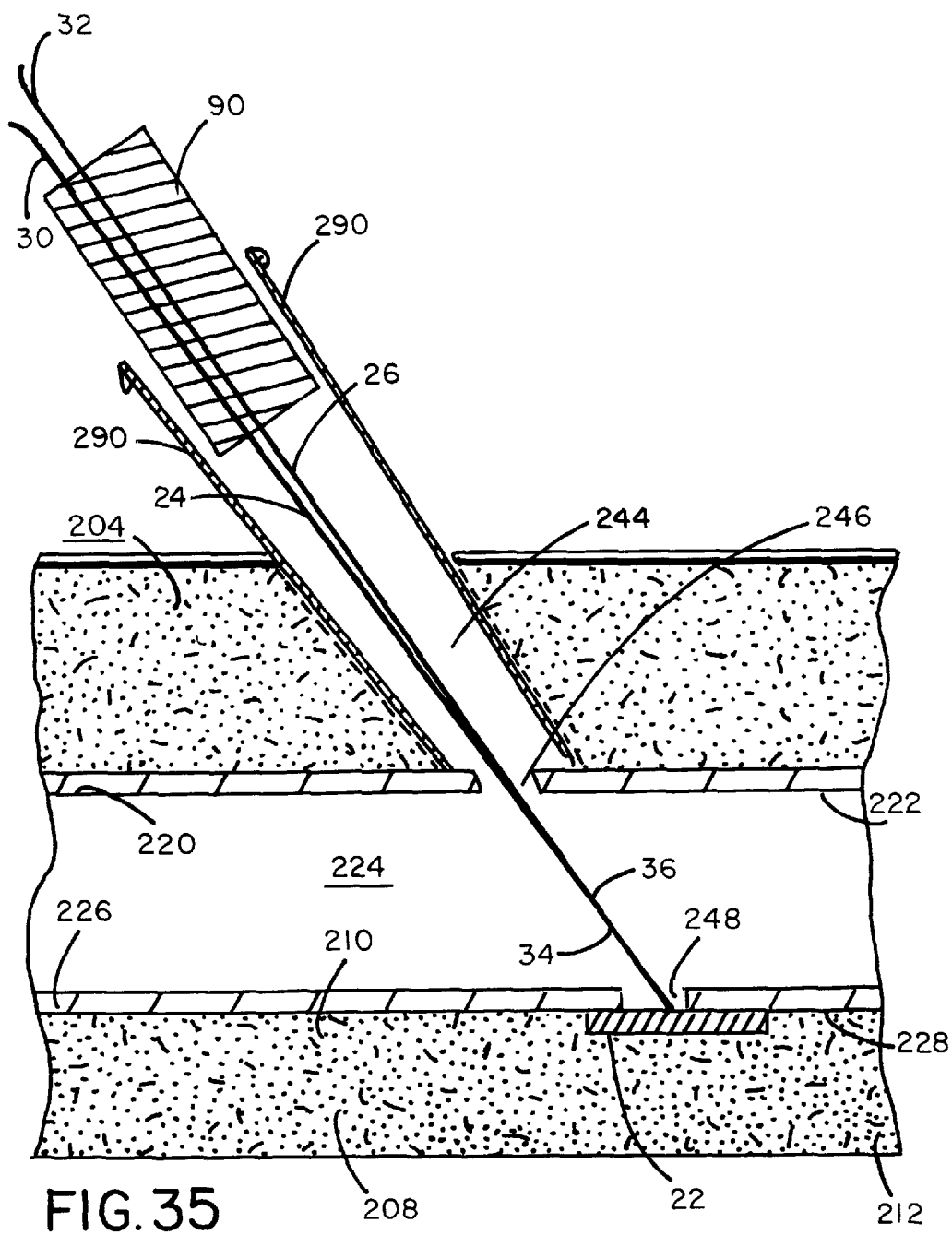

As shown by FIG. 35, an introducer sheath 290 has been advanced over the guidewire into the blood vessel; and the guidewire removed entirely from the anatomical site. The sheath is typically a peel-away carrier and conduit which provides an interior passageway into the central blood flow channel of the blood vessel. The alternative solid, cylindrically-shaped plug closure 90 (illustrated by FIG. 8) has two passageways, 92, 94 for receiving and juncture with the two extended steering cables 24, 26 of the deployed closure guiding stabilizer 20, then in aligned position at the exterior surface of the posterior vascular wall 226 adjacent the penetration fracture 248. The distal ends 34, 36 of the steering cables 24, 26 are received and passed through the passageways 92, 94 as shown by FIG. 35. The migration of the received plug closure 90 then proceeds through the interior of the introducer sheath 290 using the two received steering cables 24, 26 as guidelines.

Figure 36:
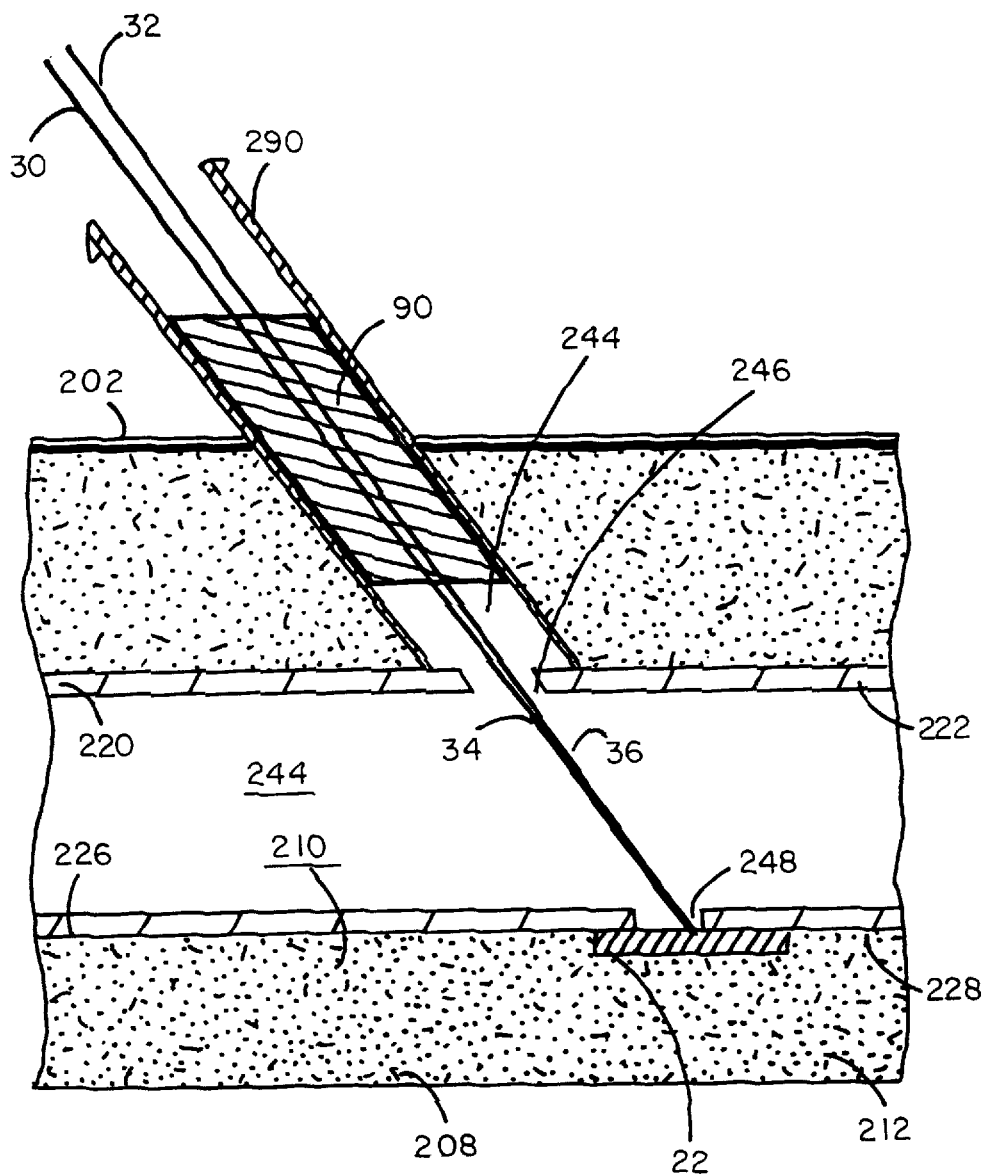

The plug closure 90 then is advanced through the axial length of the introducer sheath 290 using the steering cables 24, 26 for a controlled descent and entry into the anterior void space 244 in the superficial tissue layer 204. This is shown by FIG. 36 which shows the plug closure 90 partially introduced into the aperture void space 244 using the steering cables 24, 26 as controlling lines for guidance.

Figure 37:
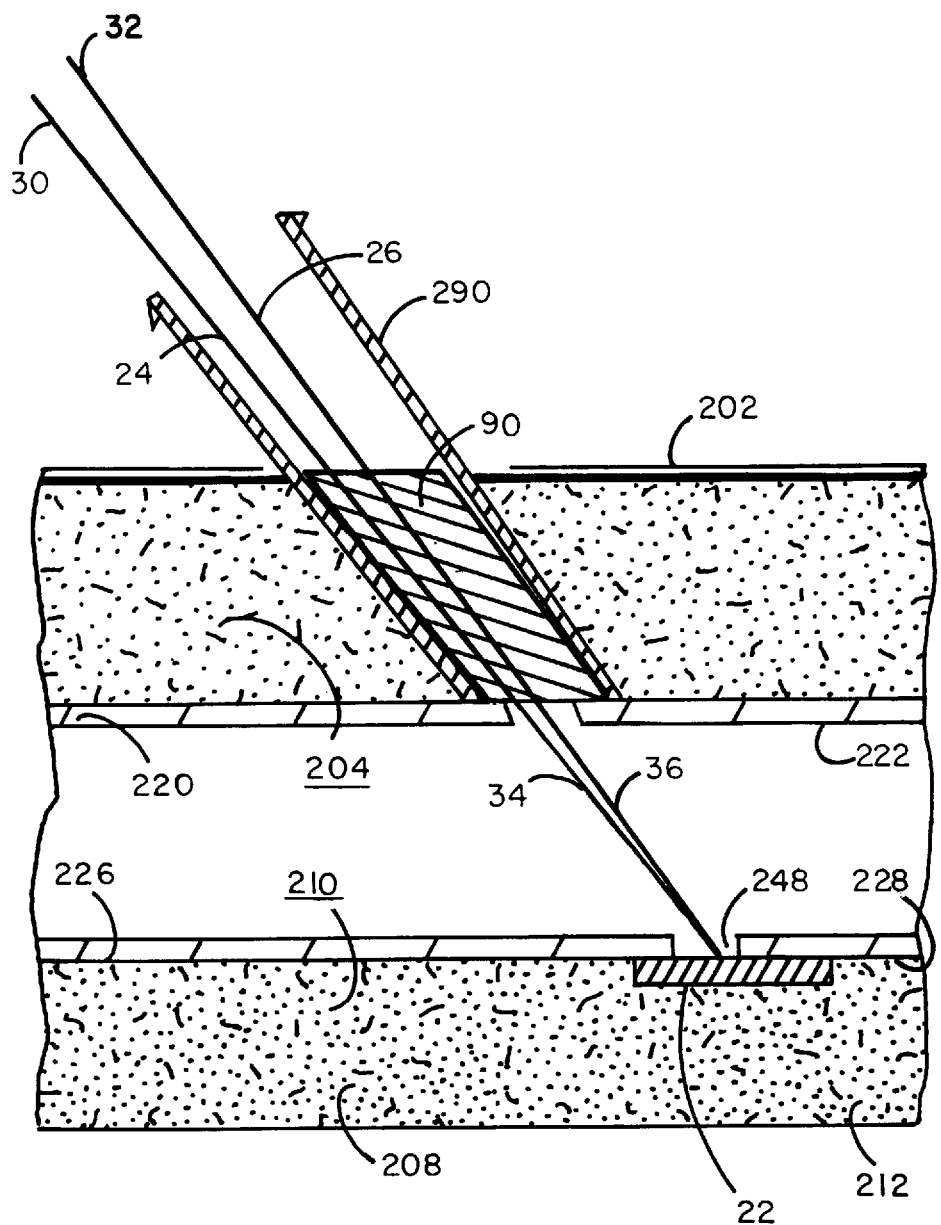
Figure 38:
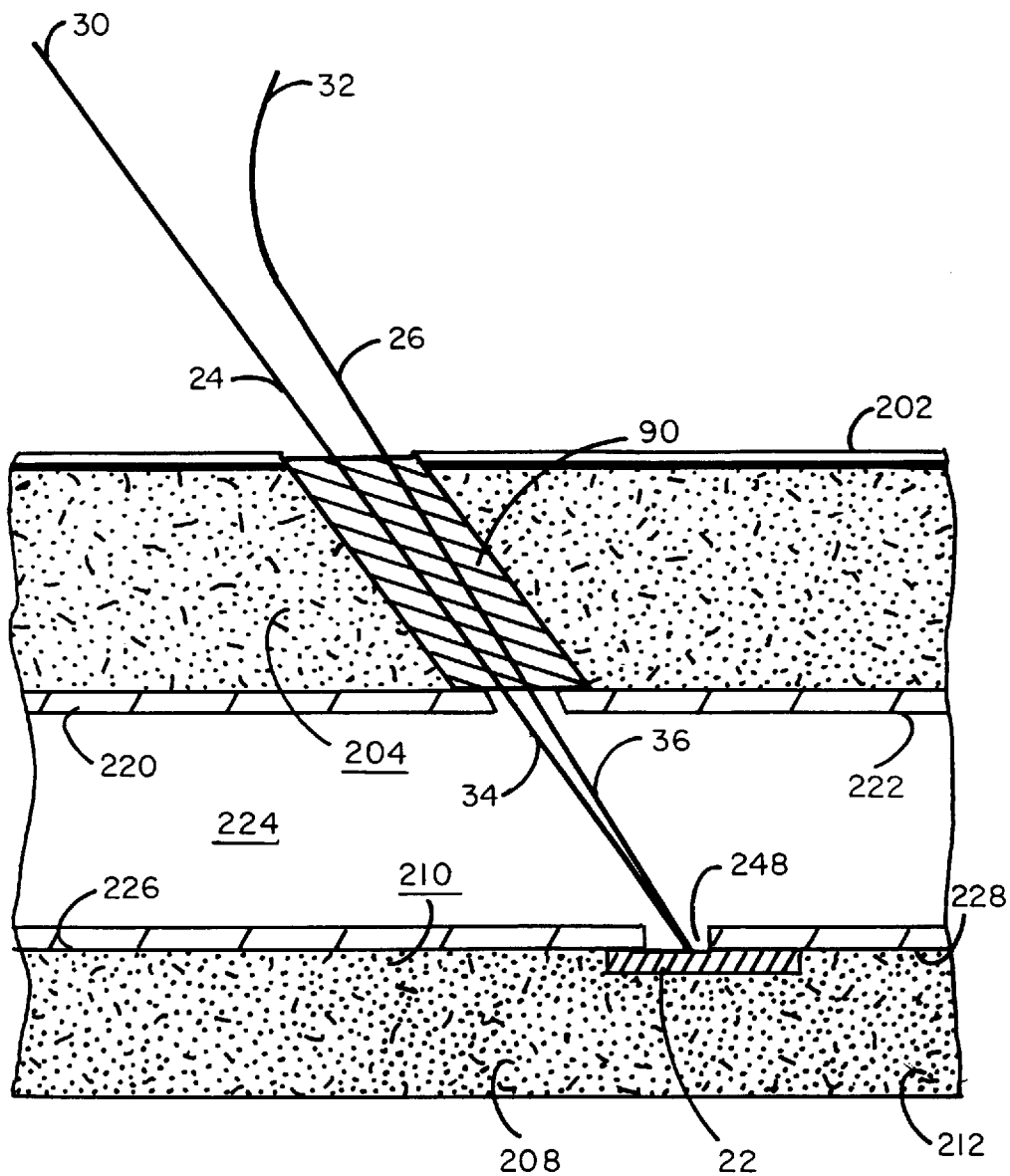

Subsequently, the solid plug closure 90 is advanced into the aperture void space completely and placed adjacent to the vascular perforation 246 in the anterior vascular wall 220. The preferred location of the solid plug closure 90 is immediately abutting the vascular perforation itself such that the plug closes and seals off the vascular perforation to achieve a stopping of blood flow and hemostasis. Preferably, the solid plug closure 90 extends from the vascular perforation 246 in the anterior vascular wall 220 to the skin puncture 242; in this manner, the aperture void space 244 in the superficial tissue layer 204 is substantially filled. The two steering cables 24, 26 continue to pass through the passageways 92, 94 of the plug closure 90 while the plug closure 90 is placed into a controlled position. This outcome and result is illustrated by FIG. 37. Upon confirmation of stable placement of the solid plug closure 90 at the vascular perforation 246 and within the aperture void space 244 of the superficial tissue layer 204 and with confirmation of satisfactory hemostasis, the sheath 290 is then removed by the attending physician or surgeon by peeling off the sheath housing and removing the sheath completely from the percutaneous puncture site. This manipulation and result is illustrated by FIG. 38.

It will be recognized and appreciated that the extended steering cables 24, 26 passing through the thickness of the solid plug closure 90 remain exposed to the external ambient environment at their proximal ends 30–32 while the distal ends 34, 36 remain rotably attached to the deployed buttressing support member 22 (then disposed in aligned placement at the exterior surface of the posterior vascular wall 226 adjacent the penetration fracture 248). In this manner, the extended steering cables 24, 26 provide guidance and control for the placement and final positioning of the solid plug closure 90 at the vascular perforation 246 in the anterior vascular wall 220. Accordingly, the closure guiding stabilizer 20 provides for an aligned closing of the vascular perforation on-demand using the steering cables 24, 26 and the solid plug closure 90.

After the attending physician or surgeon is satisfied with the placement of the solid plug closure 90 adjacent the vascular perforation 246 in the anterior vascular wall 220 and with its controlled position in filling the aperture void space in the superficial tissue layer, the proximal ends 30, 32 are desirably joined to the skin as sutures for permanent and effective sealing of the puncture site in a stabilized manner.

It will be recalled that the two steering cables 24, 26 are desirably composed of resorbable suture material; and that such suture material can be employed as tangible sutures to close and seal a puncture site, knowing that the material itself will be resorbed by the body within several weeks. The result and consequence of using the steering cables as sutures to reliably seal the percutaneous puncture and the positioned solid plug closure in place is illustrated by FIG. 39. The act of suturing using the steering cables as suture lines and material completes the second preferred method; and achieves the desired goal and result of an aligned closing and stabilized sealing of a vascular perforation after percutaneous puncture.

The invention is not to be restricted in form nor limited in scope except by the claims appended hereto.

What I claim is:

1. An aiding apparatus for guiding and stabilizing a vascular closure in a vascular perforation after percutaneous puncture of a blood vessel in a living subject, said perforated blood vessel having an identifiable anterior vascular wall, a locally-sited puncture and aperture void space in the anterior vascular wall, a central blood flow channel, and an oppositely disposed posterior vascular wall, said aiding apparatus comprising:

a closure guiding stabilizer suitable for on-demand aligned deployment within a living subject adjacent an exterior surface of a posterior vascular wall of a blood vessel after percutaneous puncture and for on-demand extension and passage in part from the aligned deployment within a living subject through a posterior vascular wall, across a blood flow channel, and out an aperture void space of a puncture site in an anterior vascular wall into the ambient environment, said closure guiding stabilizer being comprised of a buttressing support member having predetermined dimensions and an elongated configuration suitable for on-demand placement adjacent to an exterior surface of a posterior vascular wall disposed opposite to the aperture void space of a puncture site in an anterior vascular wall of a blood vessel in a living subject; and at least one steering cable of predetermined length and composition rotably attached to said buttressing support member and suitable for aligned extension and passage on-demand from within a living subject through a posterior vascular wall, across a blood flow channel, and out an aperture void space of a puncture site in an anterior vascular wall into the ambient environment, whereby a vascular closure is guided into a controlled position at an aperture void space of a puncture site via said steering cable for an aligned closing and stabilized sealing of a vascular perforation after percutaneous puncture of a blood vessel.

2. A closure apparatus for aligned closing and stabilized sealing of a vascular perforation after percutaneous puncture of a blood vessel in a living subject, said perforated blood vessel having an identifiable anterior vascular wall, a locally-sited puncture and aperture void space in the anterior vascular wall, a central blood flow channel, and an oppositely disposed posterior vascular wall, said closure apparatus comprising:

a closure guiding stabilizer suitable for on-demand aligned deployment within a living subject adjacent an exterior surface of a posterior vascular wall of a blood vessel after percutaneous puncture and for on-demand extension and passage in part from the aligned deployment within a living subject through a posterior vascular wall, across the blood flow channel, and out an aperture void space of a puncture site in an anterior vascular wall into the ambient environment, said closure guiding stabilizer being comprised of (i) a buttressing support member having predetermined dimensions and an elongated configuration suitable for on-demand placement via the vascular perforation adjacent an exterior surface of a posterior vascular wall disposed opposite to the aperture void space of a puncture site in an anterior vascular wall of a blood vessel in a living subject, and (ii) at least one steering cable of predetermined length and composition rotably attached to said buttressing support member and suitable for aligned extension and passage on-demand from within a living subject through a posterior vascular wall, across a blood flow channel, and out an aperture void space of a puncture site in an oppositely disposed anterior vascular wall into the ambient environment; and a vascular closure adapted for on-demand receiving of and juncture with said steering cable of said guiding stabilizer after placement of said buttressing support member in a living subject and extension of said steering cable from within a living subject into the ambient environment, said vascular closure being guided into a controlled position at an aperture void space via said steering cable for an aligned closing and stabilized sealing of a vascular perforation after percutaneous puncture of a blood vessel.

3. A kit apparatus for aligned closing and stabilized sealing of a vascular perforation after percutaneous puncture of a blood vessel in a living subject, said perforated blood vessel having an identifiable anterior vascular wall, a locally-sited puncture and aperture void space in the anterior vascular wall, a central blood flow channel, and an oppositely disposed posterior vascular wall, said kit apparatus comprising:

a multi-lumen needle suitable for percutaneous puncture of a blood vessel in a living subject, said needle being of fixed gauge and axial length, having discrete proximal and distal ends, and presenting at least first and second openings at the proximal end, at least first and second internal lumens of predetermined diameter which extend over most of the axial length of said needle, and at least first and second exit holes at divergent locations at the distal end of said needle, wherein said first exit hole at said distal end of said needle can be situated within a blood flow channel of a blood vessel when said needle is used for percutaneous puncture, and wherein said second exit hole at said distal end of said needle can be concurrently situated at an exterior surface of a posterior vascular wall of a blood vessel when said needle is used for percutaneous puncture;

a closure guiding stabilizer suitable for on-demand aligned deployment within a living subject adjacent an exterior surface of a posterior vascular wall of a blood vessel via said multi-lumen needle after percutaneous puncture and for on-demand extension and passage in part from the aligned deployment within a living subject through the posterior vascular wall, across the blood flow channel, and out the aperture void space of said puncture site in an anterior vascular wall into the ambient environment, said closure guiding stabilizer being comprised of (i) a buttressing support member having predetermined dimensions and an elongated configuration for on-demand placement via said multi-lumen needle adjacent an exterior surface of a posterior vascular wall disposed opposite to the aperture void space of a puncture site in the anterior vascular wall of a blood vessel in a living subject, and (ii) at least one steering cable of predetermined length and composition rotably attached to said buttressing support member and suitable for aligned extension and passage on-demand from within a living subject through a posterior vascular wall, across a blood flow channel, and out the aperture void space of said puncture site in an oppositely disposed anterior vascular wall into the ambient environment; and a vascular closure adapted for on-demand receiving of and juncture with said steering cable of said guiding stabilizer after aligned deployment in a living subject and extension of said steering cable into the ambient environment, said vascular closure being guided into a controlled position at an aperture void space via said steering cable for an aligned closing and stabilized sealing of a vascular perforation after percutaneous puncture of a blood vessel.

4. A method for aligned closing and stabilized sealing of a vascular perforation after percutaneous puncture of a blood vessel in a living subject, said perforated blood vessel having an identifiable anterior vascular wall, a locally-sited puncture and aperture void space in the anterior vascular wall, a central blood flow channel, and an oppositely disposed posterior vascular wall, said method comprising the steps of:

obtaining a multi-lumen needle suitable for percutaneous puncture of a blood vessel in a living subject, said needle being of fixed gauge and axial length, having discrete proximal and distal ends, and presenting at least first and second openings at the proximal end, at least first and second internal lumens of predetermined diameter which extend over most of the axial length of said needle, and at least first and second exit holes at divergent locations at the distal end of said needle;

percutaneously puncturing a blood vessel in a living subject using said multi-lumen needle such that said first exit hole at the distal end of said needle becomes situated within the blood flow channel of the blood vessel and said second exit hole at the distal end of said needle becomes concurrently situated at an exterior surface of a posterior vascular wall of the blood vessel;

deploying a closure guiding stabilizer via said second exit hole of said multi-lumen needle in an aligned placement within a living subject adjacent to an exterior surface of the posterior vascular wall of the perforated blood vessel, said deployed closure guiding stabilizer being comprised of (i) a buttressing support member having predetermined dimensions and an elongated configuration for placement adjacent to the exterior surface of a portion of the posterior vascular wall disposed opposite to the aperture void space of the puncture site in the anterior vascular wall of a blood vessel in the living subject, and (ii) at least one steering cable rotably attached to said buttressing support member for aligned extension and passage on-demand through the posterior vascular wall, across the blood flow channel, and out the aperture void space of said puncture site in the oppositely disposed anterior vascular wall into the ambient environment;

extending said steering cable of said deployed closure guiding stabilizer via said multi-lumen needle through the posterior vascular wall, across the blood flow channel, and out the aperture void space of said puncture site in the oppositely disposed anterior vascular wall into the ambient environment;

procuring a vascular closure adapted for on-demand receiving of and juncture with said extended steering cable of said deployed closure guiding stabilizer; and joining said vascular closure to said extended steering cable as received in the ambient environment; and guiding said joined vascular closure into a controlled position within the aperture void space of the puncture site using said received steering cable for an aligned closing and stabilized sealing of the percutaneous perforation.

* * * * *